(12) United States Patent
Liljegren et al.

(10) Patent No.: US 7,169,964 B2
(45) Date of Patent: Jan. 30, 2007

(54) GENETIC CONTROL OF ORGAN ABSCISSION

(75) Inventors: Sarah J. Liljegren, Carrboro, NC (US); Joseph R. Ecker, Carlsbad, CA (US); Martin F. Yanofsky, San Diego, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 274 days.

(21) Appl. No.: 10/630,518

(22) Filed: Jul. 29, 2003

(65) Prior Publication Data

US 2004/0143872 A1 Jul. 22, 2004

Related U.S. Application Data

(63) Continuation of application No. PCT/US02/01938, filed on Jan. 22, 2002.

(60) Provisional application No. 60/264,974, filed on Jan. 29, 2001.

(51) Int. Cl.
*C12N 15/82* (2006.01)
(52) U.S. Cl. ............ 800/276; 435/440; 435/441
(58) Field of Classification Search ............ 800/276, 800/290, 278; 435/440, 441
See application file for complete search history.

(56) References Cited

OTHER PUBLICATIONS

Zhuang et al (2005, Plant, Cell and Environment 28(2):147-156).*
Jensen et al (2000, Plant Molecular Biology 44:799-814).*
Antonny, et al., *Activation of ADP-ribosylation Factor 1 GTPase-Activating Protein by Phosphatidylcholine-derived Diacylglycerols*, J Biol Chem 272:30848-30851 (1997).
Boguski, et al., *Proteins regulating Ras and its relatives*, Nature 366:643-654 (1993).
Campisi, et al., *Generation of enhancer grap lines in Arabidopsis and characterization of expression patterns in the inflorescence*, Plant J 17:699-707 (1999).
Cosson, et al., *Coatomer (COPI)-coated vesicles: role in intracellular transport and protein sorting*, Curr. Opin. Cell Biol. 9:484-487 (1997).
Kahn, et al., *ARF Signaling: A Potential Role for Phospholipase D in Membrane Traffic*, Cell 75:1045-1048 (1993).
Kardolus, et al., *The floral abscission zone in series Acaulia and related taxa of Solanum section Petota*, Can. J. Bot. 76:1424-1432 (1998).
Konieczny, et al, *A procedure for mapping Arabidopsis mutations using co-dominant ecotype-specific PCR-based markers*, The Plant Journal 4:403-410 (1993).
Lightner, et al., *Seed Mutagenesis of Arabidopsis*, Methods in Molecular Biology 82:91-103 (1998).
Liljegren, et al., *Shatterproof mads-box genes control seed dispersal in Arabidopsis*, Nature 404:766-770 (2000).
Makler, et al., *ADP-ribosylation Factor-directed GTPase-activating Protein*, The Journal of Biol. Chemistry 270:5232-5237 (1995).
Moss, et al., *Molecules in the ARF Orbit*, The Journal of Biol. Chemistry 273:21431-21434 (1998).
Parmentier, et al. (1994) GenBank Accession #Z37245 (gi:587021) (http://www.ncbi.nlm.nih.gov).
Roberts, et al., *Abscission, Dehiscence, and Other Cell Separation Processes*, Annu. Rev. Plant Biol. 53:131-158 (2002).
Yanagisawa, et al., *Activity of Specific Lipid-regulated ADP Ribosylation Factor-GTPase-activating Proteins is Required for Sec14p-dependent Golgi Secretory Function in Yeast*, Molecular Biology of the Cell, 13:2193-2206 (2002).

* cited by examiner

*Primary Examiner*—Stuart F. Baum
(74) *Attorney, Agent, or Firm*—Morrison & Foerster LLP

(57) ABSTRACT

A method for decreasing the rate of organ or floral abscission is described. The method includes modifying the ARF GAP domain of a gene. In one instance the gene is the NEVER-SHED gene.

10 Claims, 2 Drawing Sheets

NEVERSHED contains a predicted ARFGAP domain

|  |  |  |  |  |  |  |
|---|---|---|---|---|---|---|
| plant | NEV | HRKILEGLLKHPENRE | AD | KTKGPRWASVNLGIFI | MQ | SGIHRSLGVHISKVRSATLD |
| rat | ARFGAP1 | TRKVLKEVRAQDENNV | FE | GAPNPQWVSVTYGIWI | LE | SGRHRGLGVHLSFVRSVTMD |
| yeast | GCS1 | TRRRLLQLQKIGANKK | MD | GAPNPQWATPKFGAFI | LE | AGIHRGLGVHISFVRSITMD |
| fly | CG8243 | CQTLTQMLRDEDNKY | VD | DAKGPRWASWNLGMFL | IR | AGIHRNLGVHISRVKSVNLD |
| worm | W09D10.1 | LQGFLLDMLKEEENKY | AD | QAKTPRWAAWNLGIFI | IR | AGIHRNLGVHISRVNSVNLD |
|  |  | C C | | C PW | G C C | HR | nev-1
C to Y ↓

|  |  |  |
|---|---|---|
| NEV | TWLPEQVAFIQSMGNDKANSYWEAELPPNY.....DRVGIENFIRAKYEEKRWV |  |
| ARFGAP1 | KWKDIELEKMKAGGNAKFREFLEA..........QDDYEPSWSLQDKYSSRAAA |  |
| GCS1 | QFKPELLRMEKGGNEPLTEWFK............SHNIDLSPQKVKYDNPVAE |  |
| CG8243 | TWTPEQVISLQQMGNSRARAVYEAQLPDGFRRPQTDTALENFIRAKYDHKKYL |  |
| W09D10.1 | SWTPEQVOIMRVMGNEKARQVYEHDLPAQFRRPTNDQQMEQPIRSKYEQKRYI |  |
|  | KY |  |

FIG. 2

SEQUENCE LISTING

```
<160> NUMBER OF SEQ ID NOS: 21

<210> SEQ ID NO 1
<211> LENGTH: 1452
<212> TYPE: DNA
<213> ORGANISM: Arabidopsis thaliana
<220> FEATURE:
<221> NAME/KEY: CDS
<222> LOCATION: (1)...(1452)

<400> SEQUENCE: 1 atg aac gag aaa gcc aac gtc tct aag gag ctt aat gcc cgc cat aga      48
Met Asn Glu Lys Ala Asn Val Ser Lys Glu Leu Asn Ala Arg His Arg
 1               5                  10                  15 aag att ctt gaa ggg ctt ctt aaa cat cca gag aac aga gaa tgt gct      96
Lys Ile Leu Glu Gly Leu Leu Lys His Pro Glu Asn Arg Glu Cys Ala
             20                  25                  30 gac tgc aaa aca aaa ggt cca aga tgg gct agt gtt aat tta ggt atc     144
Asp Cys Lys Thr Lys Gly Pro Arg Trp Ala Ser Val Asn Leu Gly Ile
         35                  40                  45
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| ttt | atc | tgc | atg | caa | tgt | tct | ggg | att | cac | agg | agt | ctc | ggg | gta | cac | 192  |
| Phe | Ile | Cys | Met | Gln | Cys | Ser | Gly | Ile | His | Arg | Ser | Leu | Gly | Val | His |      |
|     | 50  |     |     |     |     | 55  |     |     |     |     | 60  |     |     |     |     |      |
| ata | tcg | aag | gtt | cga | tct | gcc | act | ctg | gac | aca | tgg | ctc | ccc | gag | cag | 240  |
| Ile | Ser | Lys | Val | Arg | Ser | Ala | Thr | Leu | Asp | Thr | Trp | Leu | Pro | Glu | Gln |      |
| 65  |     |     |     |     | 70  |     |     |     |     | 75  |     |     |     |     | 80  |      |
| gtt | gca | ttt | ata | cag | tca | atg | gga | aat | gat | aaa | gca | aat | agt | tac | tgg | 288  |
| Val | Ala | Phe | Ile | Gln | Ser | Met | Gly | Asn | Asp | Lys | Ala | Asn | Ser | Tyr | Trp |      |
|     |     |     |     | 85  |     |     |     |     | 90  |     |     |     |     | 95  |     |      |
| gaa | gca | gag | cta | ccc | cca | aac | tat | gat | aga | gtt | gga | att | gag | aat | ttt | 336  |
| Glu | Ala | Glu | Leu | Pro | Pro | Asn | Tyr | Asp | Arg | Val | Gly | Ile | Glu | Asn | Phe |      |
|     |     |     | 100 |     |     |     |     | 105 |     |     |     |     | 110 |     |     |      |
| ata | cgt | gca | aag | tat | gaa | gag | aag | aga | tgg | gtt | tct | aga | ggg | gaa | aag | 384  |
| Ile | Arg | Ala | Lys | Tyr | Glu | Glu | Lys | Arg | Trp | Val | Ser | Arg | Gly | Glu | Lys |      |
|     |     | 115 |     |     |     |     | 120 |     |     |     |     | 125 |     |     |     |      |
| gct | aga | tca | cct | cct | aga | gtc | gag | cag | gaa | cgg | cgg | aaa | tct | gtg | gag | 432  |
| Ala | Arg | Ser | Pro | Pro | Arg | Val | Glu | Gln | Glu | Arg | Arg | Lys | Ser | Val | Glu |      |
|     | 130 |     |     |     |     | 135 |     |     |     |     | 140 |     |     |     |     |      |
| aga | agt | ggg | ccg | gga | tat | gag | cat | gga | cat | agt | agt | agt | cct | gta | aat | 480  |
| Arg | Ser | Gly | Pro | Gly | Tyr | Glu | His | Gly | His | Ser | Ser | Ser | Pro | Val | Asn |      |
| 145 |     |     |     |     | 150 |     |     |     |     | 155 |     |     |     |     | 160 |      |
| ttg | ttt | gag | gag | agg | aaa | act | att | cca | gca | tct | aga | aca | aga | aat | aat | 528  |
| Leu | Phe | Glu | Glu | Arg | Lys | Thr | Ile | Pro | Ala | Ser | Arg | Thr | Arg | Asn | Asn |      |
|     |     |     |     | 165 |     |     |     |     | 170 |     |     |     |     | 175 |     |      |
| gtt | gct | gca | acg | aga | ata | aat | ctt | ccc | gtg | cct | ccc | caa | gga | ccc | agt | 576  |
| Val | Ala | Ala | Thr | Arg | Ile | Asn | Leu | Pro | Val | Pro | Pro | Gln | Gly | Pro | Ser |      |
|     |     |     | 180 |     |     |     |     | 185 |     |     |     |     | 190 |     |     |      |
| cag | gtt | ata | aag | cca | cag | cag | aaa | atg | gag | tct | gca | gct | act | cca | gta | 624  |
| Gln | Val | Ile | Lys | Pro | Gln | Gln | Lys | Met | Glu | Ser | Ala | Ala | Thr | Pro | Val |      |
|     |     | 195 |     |     |     |     | 200 |     |     |     |     | 205 |     |     |     |      |
| gag | agg | gag | aaa | caa | gca | gta | aat | gtt | gca | cca | gca | tca | gat | cct | cca | 672  |
| Glu | Arg | Glu | Lys | Gln | Ala | Val | Asn | Val | Ala | Pro | Ala | Ser | Asp | Pro | Pro |      |
|     | 210 |     |     |     |     | 215 |     |     |     |     | 220 |     |     |     |     |      |
| aag | gtg | gat | ttt | gct | act | gat | ctg | ttt | aac | atg | cta | tca | atg | gat | gat | 720  |
| Lys | Val | Asp | Phe | Ala | Thr | Asp | Leu | Phe | Asn | Met | Leu | Ser | Met | Asp | Asp |      |
| 225 |     |     |     |     | 230 |     |     |     |     | 235 |     |     |     |     | 240 |      |
| tcg | act | aca | aat | acc | tca | gag | gca | act | cct | ggc | gat | act | cct | gcc | gat | 768  |
| Ser | Thr | Thr | Asn | Thr | Ser | Glu | Ala | Thr | Pro | Gly | Asp | Thr | Pro | Ala | Asp |      |
|     |     |     |     | 245 |     |     |     |     | 250 |     |     |     |     | 255 |     |      |
| gat | aac | tca | tgg | gct | ggc | ttt | cag | tct | gct | gga | agt | ggt | caa | acg | gca | 816  |
| Asp | Asn | Ser | Trp | Ala | Gly | Phe | Gln | Ser | Ala | Gly | Ser | Gly | Gln | Thr | Ala |      |
|     |     |     | 260 |     |     |     |     | 265 |     |     |     |     | 270 |     |     |      |
| gag | aaa | att | gtc | aca | gcc | aag | cct | gct | gag | agc | agt | tct | cct | cca | gct | 864  |
| Glu | Lys | Ile | Val | Thr | Ala | Lys | Pro | Ala | Glu | Ser | Ser | Ser | Pro | Pro | Ala |      |
|     |     | 275 |     |     |     |     | 280 |     |     |     |     | 285 |     |     |     |      |
| tca | tct | tct | gac | ttt | gag | gat | ttg | ttt | aag | gac | aca | cct | aat | tta | aca | 912  |
| Ser | Ser | Ser | Asp | Phe | Glu | Asp | Leu | Phe | Lys | Asp | Thr | Pro | Asn | Leu | Thr |      |
|     | 290 |     |     |     |     | 295 |     |     |     |     | 300 |     |     |     |     |      |
| act | caa | caa | gca | cca | aaa | gat | gtg | aaa | ggc | gat | atc | atg | agc | ctg | ttt | 960  |
| Thr | Gln | Gln | Ala | Pro | Lys | Asp | Val | Lys | Gly | Asp | Ile | Met | Ser | Leu | Phe |      |
| 305 |     |     |     |     | 310 |     |     |     |     | 315 |     |     |     |     | 320 |      |
| gag | aag | acg | aat | ata | gta | tcg | cct | ttt | gcc | atg | cat | cag | caa | cag | gtt | 1008 |
| Glu | Lys | Thr | Asn | Ile | Val | Ser | Pro | Phe | Ala | Met | His | Gln | Gln | Gln | Val |      |
|     |     |     |     | 325 |     |     |     |     | 330 |     |     |     |     | 335 |     |      |
| gct | atg | ctc | gct | cag | cag | caa | gcc | ctt | tac | atg | gct | gca | gcg | aaa | gct | 1056 |
| Ala | Met | Leu | Ala | Gln | Gln | Gln | Ala | Leu | Tyr | Met | Ala | Ala | Ala | Lys | Ala |      |
|     |     |     | 340 |     |     |     |     | 345 |     |     |     |     | 350 |     |     |      |
| gct | gga | ggc | act | cca | aac | ggc | gtg | aat | caa | caa | gct | att | gct | aat | gct | 1104 |
| Ala | Gly | Gly | Thr | Pro | Asn | Gly | Val | Asn | Gln | Gln | Ala | Ile | Ala | Asn | Ala |      |

```
                355                 360                 365
ctt aac gta gct tct gca aat tgg tca aac ccc ggc ggc tac cag atc    1152
Leu Asn Val Ala Ser Ala Asn Trp Ser Asn Pro Gly Gly Tyr Gln Ile
    370                 375                 380 ccc gga atg act aac ccc gta ggt ggt caa gct gat ctc cag aaa ctt    1200
Pro Gly Met Thr Asn Pro Val Gly Gly Gln Ala Asp Leu Gln Lys Leu
385                 390                 395                 400 atg caa aac atg aat atg aac gca aac atg aac acg aga ccc gca caa    1248
Met Gln Asn Met Asn Met Asn Ala Asn Met Asn Thr Arg Pro Ala Gln
                405                 410                 415 ccg caa gag aac act cta caa tac cca tca tcc agt ttc tac aca atg    1296
Pro Gln Glu Asn Thr Leu Gln Tyr Pro Ser Ser Ser Phe Tyr Thr Met
            420                 425                 430 ggt caa gct aat caa gtg aac ggt atg acc cca aac tca acc ggt aaa    1344
Gly Gln Ala Asn Gln Val Asn Gly Met Thr Pro Asn Ser Thr Gly Lys
        435                 440                 445 cct cag tca tca tcc gca acc caa cca aca agc acc aca cca tct tca    1392
Pro Gln Ser Ser Ser Ala Thr Gln Pro Thr Ser Thr Thr Pro Ser Ser
    450                 455                 460 caa tca ggc aaa gac ttt gat ttc tct tcc ttg atg gat gga atg ttc    1440
Gln Ser Gly Lys Asp Phe Asp Phe Ser Ser Leu Met Asp Gly Met Phe
465                 470                 475                 480 aca aaa cat tga                                                    1452
Thr Lys His *

<210> SEQ ID NO 2
<211> LENGTH: 483
<212> TYPE: PRT
<213> ORGANISM: Arabidopsis thaliana

<400> SEQUENCE: 2

Met Asn Glu Lys Ala Asn Val Ser Lys Glu Leu Asn Ala Arg His Arg
 1               5                  10                  15

Lys Ile Leu Glu Gly Leu Leu Lys His Pro Glu Asn Arg Glu Cys Ala
            20                  25                  30

Asp Cys Lys Thr Lys Gly Pro Arg Trp Ala Ser Val Asn Leu Gly Ile
        35                  40                  45

Phe Ile Cys Met Gln Cys Ser Gly Ile His Arg Ser Leu Gly Val His
    50                  55                  60

Ile Ser Lys Val Arg Ser Ala Thr Leu Asp Thr Trp Leu Pro Glu Gln
65                  70                  75                  80

Val Ala Phe Ile Gln Ser Met Gly Asn Asp Lys Ala Asn Ser Tyr Trp
                85                  90                  95

Glu Ala Glu Leu Pro Pro Asn Tyr Asp Arg Val Gly Ile Glu Asn Phe
            100                 105                 110

Ile Arg Ala Lys Tyr Glu Glu Lys Arg Trp Val Ser Arg Gly Glu Lys
        115                 120                 125

Ala Arg Ser Pro Pro Arg Val Glu Gln Glu Arg Lys Ser Val Glu
    130                 135                 140

Arg Ser Gly Pro Gly Tyr Glu His Gly His Ser Ser Ser Pro Val Asn
145                 150                 155                 160

Leu Phe Glu Glu Arg Lys Thr Ile Pro Ala Ser Arg Thr Arg Asn Asn
                165                 170                 175

Val Ala Ala Thr Arg Ile Asn Leu Pro Val Pro Pro Gln Gly Pro Ser
            180                 185                 190

Gln Val Ile Lys Pro Gln Gln Lys Met Glu Ser Ala Ala Thr Pro Val
        195                 200                 205
```

-continued

```
Glu Arg Glu Lys Gln Ala Val Asn Val Ala Pro Ala Ser Asp Pro Pro
    210                 215                 220
Lys Val Asp Phe Ala Thr Asp Leu Phe Asn Met Leu Ser Met Asp Asp
225                 230                 235                 240
Ser Thr Thr Asn Thr Ser Glu Ala Thr Pro Gly Asp Thr Pro Ala Asp
                245                 250                 255
Asp Asn Ser Trp Ala Gly Phe Gln Ser Ala Gly Ser Gly Gln Thr Ala
            260                 265                 270
Glu Lys Ile Val Thr Ala Lys Pro Ala Glu Ser Ser Pro Pro Ala
        275                 280                 285
Ser Ser Ser Asp Phe Glu Asp Leu Phe Lys Asp Thr Pro Asn Leu Thr
    290                 295                 300
Thr Gln Gln Ala Pro Lys Asp Val Lys Gly Asp Ile Met Ser Leu Phe
305                 310                 315                 320
Glu Lys Thr Asn Ile Val Ser Pro Phe Ala Met His Gln Gln Val
                325                 330                 335
Ala Met Leu Ala Gln Gln Gln Ala Leu Tyr Met Ala Ala Lys Ala
            340                 345                 350
Ala Gly Gly Thr Pro Asn Gly Val Asn Gln Gln Ala Ile Ala Asn Ala
        355                 360                 365
Leu Asn Val Ala Ser Ala Asn Trp Ser Asn Pro Gly Gly Tyr Gln Ile
    370                 375                 380
Pro Gly Met Thr Asn Pro Val Gly Gly Gln Ala Asp Leu Gln Lys Leu
385                 390                 395                 400
Met Gln Asn Met Asn Met Asn Ala Asn Met Asn Thr Arg Pro Ala Gln
                405                 410                 415
Pro Gln Glu Asn Thr Leu Gln Tyr Pro Ser Ser Ser Phe Tyr Thr Met
            420                 425                 430
Gly Gln Ala Asn Gln Val Asn Gly Met Thr Pro Asn Ser Thr Gly Lys
        435                 440                 445
Pro Gln Ser Ser Ser Ala Thr Gln Pro Thr Ser Thr Thr Pro Ser Ser
    450                 455                 460
Gln Ser Gly Lys Asp Phe Asp Phe Ser Ser Leu Met Asp Gly Met Phe
465                 470                 475                 480
Thr Lys His
```

<210> SEQ ID NO 3
<211> LENGTH: 1452
<212> TYPE: DNA
<213> ORGANISM: Arabidopsis thaliana
<220> FEATURE:
<221> NAME/KEY: CDS
<222> LOCATION: (1)...(1452)

<400> SEQUENCE: 3

```
atg aac gag aaa gcc aac gtc tct aag gag ctt aat gcc cgc cat aga     48
Met Asn Glu Lys Ala Asn Val Ser Lys Glu Leu Asn Ala Arg His Arg
  1               5                  10                  15 aag att ctt gaa ggg ctt ctt aaa cat cca gag aac aga gaa tgt gct     96
Lys Ile Leu Glu Gly Leu Leu Lys His Pro Glu Asn Arg Glu Cys Ala
                 20                  25                  30 gac tgc aaa aca aaa ggt cca aga tgg gct agt gtt aat tta ggt atc    144
Asp Cys Lys Thr Lys Gly Pro Arg Trp Ala Ser Val Asn Leu Gly Ile
             35                  40                  45 ttt atc tac atg caa tgt tct ggg att cac agg agt ctc ggg gta cac    192
Phe Ile Tyr Met Gln Cys Ser Gly Ile His Arg Ser Leu Gly Val His
         50                  55                  60
```

```
                50                  55                  60
ata tcg aag gtt cga tct gcc act ctg gac aca tgg ctc ccc gag cag      240
Ile Ser Lys Val Arg Ser Ala Thr Leu Asp Thr Trp Leu Pro Glu Gln
 65                  70                  75                  80 gtt gca ttt ata cag tca atg gga aat gat aaa gca aat agt tac tgg      288
Val Ala Phe Ile Gln Ser Met Gly Asn Asp Lys Ala Asn Ser Tyr Trp
                 85                  90                  95 gaa gca gag cta ccc cca aac tat gat aga gtt gga att gag aat ttt      336
Glu Ala Glu Leu Pro Pro Asn Tyr Asp Arg Val Gly Ile Glu Asn Phe
            100                 105                 110 ata cgt gca aag tat gaa gag aag aga tgg gtt tct aga ggg gaa aag      384
Ile Arg Ala Lys Tyr Glu Glu Lys Arg Trp Val Ser Arg Gly Glu Lys
        115                 120                 125 gct aga tca cct cct aga gtc gag cag gaa cgg cgg aaa tct gtg gag      432
Ala Arg Ser Pro Pro Arg Val Glu Gln Glu Arg Arg Lys Ser Val Glu
    130                 135                 140 aga agt ggg ccg gga tat gag cat gga cat agt agt agt cct gta aat      480
Arg Ser Gly Pro Gly Tyr Glu His Gly His Ser Ser Ser Pro Val Asn
145                 150                 155                 160 ttg ttt gag gag agg aaa act att cca gca tct aga aca aga aat aat      528
Leu Phe Glu Glu Arg Lys Thr Ile Pro Ala Ser Arg Thr Arg Asn Asn
                165                 170                 175 gtt gct gca acg aga ata aat ctt ccc gtg cct ccc caa gga ccc agt      576
Val Ala Ala Thr Arg Ile Asn Leu Pro Val Pro Pro Gln Gly Pro Ser
            180                 185                 190 cag gtt ata aag cca cag cag aaa atg gag tct gca gct act cca gta      624
Gln Val Ile Lys Pro Gln Gln Lys Met Glu Ser Ala Ala Thr Pro Val
        195                 200                 205 gag agg gag aaa caa gca gta aat gtt gca cca gca tca gat cct cca      672
Glu Arg Glu Lys Gln Ala Val Asn Val Ala Pro Ala Ser Asp Pro Pro
    210                 215                 220 aag gtg gat ttt gct act gat ctg ttt aac atg cta tca atg gat gat      720
Lys Val Asp Phe Ala Thr Asp Leu Phe Asn Met Leu Ser Met Asp Asp
225                 230                 235                 240 tcg act aca aat acc tca gag gca act cct ggc gat act cct gcc gat      768
Ser Thr Thr Asn Thr Ser Glu Ala Thr Pro Gly Asp Thr Pro Ala Asp
                245                 250                 255 gat aac tca tgg gct ggc ttt cag tct gct gga agt ggt caa acg gca      816
Asp Asn Ser Trp Ala Gly Phe Gln Ser Ala Gly Ser Gly Gln Thr Ala
            260                 265                 270 gag aaa att gtc aca gcc aag cct gct gag agc agt tct cct cca gct      864
Glu Lys Ile Val Thr Ala Lys Pro Ala Glu Ser Ser Ser Pro Pro Ala
        275                 280                 285 tca tct tct gac ttt gag gat ttg ttt aag gac aca cct aat tta aca      912
Ser Ser Ser Asp Phe Glu Asp Leu Phe Lys Asp Thr Pro Asn Leu Thr
    290                 295                 300 act caa caa gca cca aaa gat gtg aaa ggc gat atc atg agc ctg ttt      960
Thr Gln Gln Ala Pro Lys Asp Val Lys Gly Asp Ile Met Ser Leu Phe
305                 310                 315                 320 gag aag acg aat ata gta tcg cct ttt gcc atg cat cag caa cag gtt     1008
Glu Lys Thr Asn Ile Val Ser Pro Phe Ala Met His Gln Gln Gln Val
                325                 330                 335 gct atg ctc gct cag cag caa gcc ctt tac atg gct gca gcg aaa gct     1056
Ala Met Leu Ala Gln Gln Gln Ala Leu Tyr Met Ala Ala Ala Lys Ala
            340                 345                 350 gct gga ggc act cca aac ggc gtg aat caa caa gct att gct aat gct     1104
Ala Gly Gly Thr Pro Asn Gly Val Asn Gln Gln Ala Ile Ala Asn Ala
        355                 360                 365 ctt aac gta gct tct gca aat tgg tca aac ccc ggc ggc tac cag atc     1152
```

```
                                                             -continued

Leu Asn Val Ala Ser Ala Asn Trp Ser Asn Pro Gly Gly Tyr Gln Ile
    370                 375                 380 ccc gga atg act aac ccc gta ggt ggt caa gct gat ctc cag aaa ctt      1200
Pro Gly Met Thr Asn Pro Val Gly Gly Gln Ala Asp Leu Gln Lys Leu
385                 390                 395                 400 atg caa aac atg aat atg aac gca aac atg aac acg aga ccc gca caa      1248
Met Gln Asn Met Asn Met Asn Ala Asn Met Asn Thr Arg Pro Ala Gln
                405                 410                 415 ccg caa gag aac act cta caa tac cca tca tcc agt ttc tac aca atg      1296
Pro Gln Glu Asn Thr Leu Gln Tyr Pro Ser Ser Ser Phe Tyr Thr Met
            420                 425                 430 ggt caa gct aat caa gtg aac ggt atg acc cca aac tca acc ggt aaa      1344
Gly Gln Ala Asn Gln Val Asn Gly Met Thr Pro Asn Ser Thr Gly Lys
        435                 440                 445 cct cag tca tca tcc gca acc caa cca aca agc acc aca cca tct tca      1392
Pro Gln Ser Ser Ser Ala Thr Gln Pro Thr Ser Thr Thr Pro Ser Ser
    450                 455                 460 caa tca ggc aaa gac ttt gat ttc tct tcc ttg atg gat gga atg ttc      1440
Gln Ser Gly Lys Asp Phe Asp Phe Ser Ser Leu Met Asp Gly Met Phe
465                 470                 475                 480 aca aaa cat tga                                                     1452
Thr Lys His *

<210> SEQ ID NO 4
<211> LENGTH: 483
<212> TYPE: PRT
<213> ORGANISM: Arabidopsis thaliana

<400> SEQUENCE: 4

Met Asn Glu Lys Ala Asn Val Ser Lys Glu Leu Asn Ala Arg His Arg
1               5                   10                  15

Lys Ile Leu Glu Gly Leu Leu Lys His Pro Glu Asn Arg Glu Cys Ala
            20                  25                  30

Asp Cys Lys Thr Lys Gly Pro Arg Trp Ala Ser Val Asn Leu Gly Ile
        35                  40                  45

Phe Ile Tyr Met Gln Cys Ser Gly Ile His Arg Ser Leu Gly Val His
    50                  55                  60

Ile Ser Lys Val Arg Ser Ala Thr Leu Asp Thr Trp Leu Pro Glu Gln
65                  70                  75                  80

Val Ala Phe Ile Gln Ser Met Gly Asn Asp Lys Ala Asn Ser Tyr Trp
                85                  90                  95

Glu Ala Glu Leu Pro Pro Asn Tyr Asp Arg Val Gly Ile Glu Asn Phe
            100                 105                 110

Ile Arg Ala Lys Tyr Glu Glu Lys Arg Trp Val Ser Arg Gly Glu Lys
        115                 120                 125

Ala Arg Ser Pro Pro Arg Val Glu Gln Glu Arg Arg Lys Ser Val Glu
    130                 135                 140

Arg Ser Gly Pro Gly Tyr Glu His Gly His Ser Ser Pro Val Asn
145                 150                 155                 160

Leu Phe Glu Glu Arg Lys Thr Ile Pro Ala Ser Arg Thr Arg Asn Asn
                165                 170                 175

Val Ala Ala Thr Arg Ile Asn Leu Pro Val Pro Pro Gln Gly Pro Ser
            180                 185                 190

Gln Val Ile Lys Pro Gln Gln Lys Met Glu Ser Ala Ala Thr Pro Val
        195                 200                 205

Glu Arg Glu Lys Gln Ala Val Asn Val Ala Pro Ala Ser Asp Pro Pro
    210                 215                 220
```

-continued

```
Lys Val Asp Phe Ala Thr Asp Leu Phe Asn Met Leu Ser Met Asp Asp
225                 230                 235                 240

Ser Thr Thr Asn Thr Ser Glu Ala Thr Pro Gly Asp Thr Pro Ala Asp
            245                 250                 255

Asp Asn Ser Trp Ala Gly Phe Gln Ser Ala Gly Ser Gly Gln Thr Ala
                260                 265                 270

Glu Lys Ile Val Thr Ala Lys Pro Ala Glu Ser Ser Ser Pro Pro Ala
            275                 280                 285

Ser Ser Ser Asp Phe Glu Asp Leu Phe Lys Asp Thr Pro Asn Leu Thr
290                 295                 300

Thr Gln Gln Ala Pro Lys Asp Val Lys Gly Asp Ile Met Ser Leu Phe
305                 310                 315                 320

Glu Lys Thr Asn Ile Val Ser Pro Phe Ala Met His Gln Gln Gln Val
                325                 330                 335

Ala Met Leu Ala Gln Gln Gln Ala Leu Tyr Met Ala Ala Ala Lys Ala
            340                 345                 350

Ala Gly Gly Thr Pro Asn Gly Val Asn Gln Gln Ala Ile Ala Asn Ala
            355                 360                 365

Leu Asn Val Ala Ser Ala Asn Trp Ser Asn Pro Gly Gly Tyr Gln Ile
370                 375                 380

Pro Gly Met Thr Asn Pro Val Gly Gly Gln Ala Asp Leu Gln Lys Leu
385                 390                 395                 400

Met Gln Asn Met Asn Met Asn Ala Asn Met Asn Thr Arg Pro Ala Gln
                405                 410                 415

Pro Gln Glu Asn Thr Leu Gln Tyr Pro Ser Ser Ser Phe Tyr Thr Met
            420                 425                 430

Gly Gln Ala Asn Gln Val Asn Gly Met Thr Pro Asn Ser Thr Gly Lys
            435                 440                 445

Pro Gln Ser Ser Ser Ala Thr Gln Pro Thr Ser Thr Pro Ser Ser
450                 455                 460

Gln Ser Gly Lys Asp Phe Asp Phe Ser Ser Leu Met Asp Gly Met Phe
465                 470                 475                 480

Thr Lys His

<210> SEQ ID NO 5
<211> LENGTH: 1452
<212> TYPE: DNA
<213> ORGANISM: Arabidopsis thaliana
<220> FEATURE:
<221> NAME/KEY: CDS
<222> LOCATION: (1)...(594)

<400> SEQUENCE: 5 atg aac gag aaa gcc aac gtc tct aag gag ctt aat gcc cgc cat aga      48
Met Asn Glu Lys Ala Asn Val Ser Lys Glu Leu Asn Ala Arg His Arg
1               5                   10                  15 aag att ctt gaa ggg ctt ctt aaa cat cca gag aac aga gaa tgt gct      96
Lys Ile Leu Glu Gly Leu Leu Lys His Pro Glu Asn Arg Glu Cys Ala
            20                  25                  30 gac tgc aaa aca aaa ggt cca aga tgg gct agt gtt aat tta ggt atc     144
Asp Cys Lys Thr Lys Gly Pro Arg Trp Ala Ser Val Asn Leu Gly Ile
        35                  40                  45 ttt atc tgc atg caa tgt tct ggg att cac agg agt ctc ggg gta cac     192
Phe Ile Cys Met Gln Cys Ser Gly Ile His Arg Ser Leu Gly Val His
    50                  55                  60 ata tcg aag gtt cga tct gcc act ctg gac aca tgg ctc ccc gag cag     240
```

```
Ile Ser Lys Val Arg Ser Ala Thr Leu Asp Thr Trp Leu Pro Glu Gln
 65                  70                  75                  80 gtt gca ttt ata cag tca atg gga aat gat aaa gca aat agt tac tgg      288
Val Ala Phe Ile Gln Ser Met Gly Asn Asp Lys Ala Asn Ser Tyr Trp
                 85                  90                  95 gaa gca gag cta ccc cca aac tat gat aga gtt gga att gag aat ttt      336
Glu Ala Glu Leu Pro Pro Asn Tyr Asp Arg Val Gly Ile Glu Asn Phe
            100                 105                 110 ata cgt gca aag tat gaa gag aag aga tgg gtt tct aga ggg gaa aag      384
Ile Arg Ala Lys Tyr Glu Glu Lys Arg Trp Val Ser Arg Gly Glu Lys
        115                 120                 125 gct aga tca cct cct aga gtc gag cag gaa cgg cgg aaa tct gtg gag      432
Ala Arg Ser Pro Pro Arg Val Glu Gln Glu Arg Arg Lys Ser Val Glu
    130                 135                 140 aga agt ggg ccg gga tat gag cat gga cat agt agt agt cct gta aat      480
Arg Ser Gly Pro Gly Tyr Glu His Gly His Ser Ser Ser Pro Val Asn
145                 150                 155                 160 ttg ttt gag gag agg aaa act att cca gca tct aga aca aga aat aat      528
Leu Phe Glu Glu Arg Lys Thr Ile Pro Ala Ser Arg Thr Arg Asn Asn
                165                 170                 175 gtt gct gca acg aga ata aat ctt ccc gtg cct ccc caa gga ccc agt      576
Val Ala Ala Thr Arg Ile Asn Leu Pro Val Pro Pro Gln Gly Pro Ser
            180                 185                 190 cag gtt ata aag cca tag cagaaaatgg agtctgcagc tactccagta             624
Gln Val Ile Lys Pro *
        195 gagagggaga acaagcagt aaatgttgca ccagcatcag atcctccaaa ggtggatttt     684 gctactgatc tgtttaacat gctatcaatg gatgattcga ctacaaatac ctcagaggca    744 actcctggcg atactcctgc cgatgataac tcatgggctg gctttcagtc tgctggaagt    804 ggtcaaacgg cagagaaaat tgtcacagcc aagcctgctg agagcagttc tcctccagct    864 tcatcttctg actttgagga tttgtttaag gacacaccta atttaacaac tcaacaagca    924 ccaaaagatg tgaaaggcga tatcatgagc ctgtttgaga agacgaatat agtatcgcct    984 tttgccatgc atcagcaaca ggttgctatg ctcgctcagc agcaagccct ttacatggct   1044 gcagcgaaag ctgctggagg cactccaaac ggcgtgaatc aacaagctat tgctaatgct   1104 cttaacgtag cttctgcaaa ttggtcaaac cccggcggct accagatccc cggaatgact   1164 aaccccgtag gtggtcaagc tgatctccag aaacttatgc aaaacatgaa tatgaacgca   1224 aacatgaaca cgagacccgc acaaccgcaa gagaacactc tacaataccc atcatccagt   1284 ttctacacaa tgggtcaagc taatcaagtg aacggtatga ccccaaactc aaccggtaaa   1344 cctcagtcat catccgcaac ccaaccaaca agcaccacac catcttcaca atcaggcaaa   1404 gactttgatt tctcttcctt gatggatgga atgttcacaa acattga                 1452
```

<210> SEQ ID NO 6
<211> LENGTH: 197
<212> TYPE: PRT
<213> ORGANISM: Arabidopsis thaliana

<400> SEQUENCE: 6

```
Met Asn Glu Lys Ala Asn Val Ser Lys Glu Leu Asn Ala Arg His Arg
 1               5                  10                  15

Lys Ile Leu Glu Gly Leu Leu Lys His Pro Glu Asn Arg Glu Cys Ala
            20                  25                  30

Asp Cys Lys Thr Lys Gly Pro Arg Trp Ala Ser Val Asn Leu Gly Ile
        35                  40                  45
```

```
Phe Ile Cys Met Gln Cys Ser Gly Ile His Arg Ser Leu Gly Val His
 50                  55                  60
Ile Ser Lys Val Arg Ser Ala Thr Leu Asp Thr Trp Leu Pro Glu Gln
 65                  70                  75                  80
Val Ala Phe Ile Gln Ser Met Gly Asn Asp Lys Ala Asn Ser Tyr Trp
                 85                  90                  95
Glu Ala Glu Leu Pro Pro Asn Tyr Asp Arg Val Gly Ile Glu Asn Phe
            100                 105                 110
Ile Arg Ala Lys Tyr Glu Glu Lys Arg Trp Val Ser Arg Gly Glu Lys
        115                 120                 125
Ala Arg Ser Pro Pro Arg Val Glu Gln Glu Arg Arg Lys Ser Val Glu
130                 135                 140
Arg Ser Gly Pro Gly Tyr Glu His Gly His Ser Ser Ser Pro Val Asn
145                 150                 155                 160
Leu Phe Glu Glu Arg Lys Thr Ile Pro Ala Ser Arg Thr Arg Asn Asn
                165                 170                 175
Val Ala Ala Thr Arg Ile Asn Leu Pro Val Pro Pro Gln Gly Pro Ser
            180                 185                 190
Gln Val Ile Lys Pro
        195
```

<210> SEQ ID NO 7
<211> LENGTH: 1739
<212> TYPE: DNA
<213> ORGANISM: Arabidopsis thaliana

<400> SEQUENCE: 7

```
ttgataagaa gtgttttagg ggaaagcgag gctgcaagag aatcaaataa gaaagagtaa     60
acaaaacaaa accctagttg ttgagatgtt cacataaata accaccaaga tccgatacaa    120
tcttaattgg atatcatttt aattaaccac gttcaaacct tattatatga agtttgtttc    180
ttcgaatata ttttccatat acttgattta attataaata cttatttaca taacaataca    240
tactccagaa tcaatatcct caaattttag aaaaacaatg tgagatgtac atgattgaga    300
taaagcttga agctaagtct gattaagaag aaattaaagt ttgcaaaatg tggggaagtc    360
tctatacgtg tcagagggtt tgagatctga gaatacttga agagaggcta tggagagtaa    420
ttcgagaagc aaaaataagc agtcgtctat ttactatatg agaaaaatct tccttctaga    480
tgtgcaaata tcctcctgaa aagttggtcc tcgcactgat aacaaagaga gatggctatg    540
atgatcatat atttccaagc tcatcccatc ataatcgcga cgtcacatcc cctaaaaagc    600
atattaattg ccaaagttgg tagcataact ctcttctaat ggcgacttaa aatgaaata     660
tactaagtgg atctatatat tttcaaaatt ggaaagtata tatatgtgga tgaagttaga    720
gaagttagaa atttcaaaag ctttgggat tatatttgtg ataactcccg atgatattcc     780
acatacagat aagtaaaggt gctacttaga ccaaaccgat tatgaggttt agagccagcg    840
agagaccact tctcattaga ctacaaaact ttttaggtt tattcacaca caatgtatta     900
tagttcctaa tgtataccta ttaaattaga gtttgtcgaa tgttaggatt atagttcgta    960
ttgacaaaca aatatcagtt tgaaaaatta ggaatctaag agataataat ataattattt   1020
ttttgggttt aaattgaaat ttgtgttggt tggaacattc gttgactcat cgtcacatca   1080
aataaaaatc ttagcaaata aaatatgtcc cataaacatc acataaataa acaaagaaat   1140
tggaatcaat acaacaacca ctccaaagtg gatacagaca taacaggtga tgagatggcc   1200
```

-continued

```
atgtgattta ttttccaccc gcaacactct aatgcttata tatgaccaat caaaaaaacc    1260
acttaaaccg ccaaataaac cgaccttatt tttgataaat caaaacccac ttagtcacaa    1320
attaaccaat tttatatgat tacactttca caaatattca tgtgtagatt tctttgaaaa    1380
ttttcaggtg ctgcaatcac gagtgaccga attattttg aaaatttaaa ccgaaatgaa     1440
attaaaccga accatattca attttgaaaa tgaaatctaa aaccggatta ataaaccagt    1500
accataatct gaacggtcca aaaagtattg acccatctct ctctcttggt cgctcgttct    1560
caaagggcaa agaaaaaagg attttaatt tcggagagg aagaagaaga gagagatatt     1620
gaagagcgct gaaggcggaa aagactattt tgacctcgtc gtctccgtag atcatttttc    1680
ttcagctctt cttcttcctc tttctccgat tctccttctt ttgattttat ctatccgcc     1739

<210> SEQ ID NO 8
<211> LENGTH: 5580
<212> TYPE: DNA
<213> ORGANISM: Arabidopsis thaliana

<400> SEQUENCE: 8
cagaaaaagt ctctctctct tgatcaatgt tttgtgaaca ttccatccat caaggaagag      60
aaatcaaagt ctttgcctga ttgtgaagat ggtgtggtgc ttgttggttg ggttgcggat     120
gatgactgag gttaccggt tgagtttggg gtcataccgt tcacttgatt agcttgaccc      180
attgtgtaga aactgcatta ttaataacaa ccaaagatca tatgagagtt agttaggtta     240 agcactttg ataacgttat gatgttttca gaagaaacaa acaagatgca gttttgtgtg      300
catacctgga tgatgggtat tgtagagtgt tctcttgcgg ttgtgcgggt ctcgtgttca     360
tgtttgcgtt catattcatg ttctaaaatt atggcgatgt aacagagagc aagaattagt     420
gagaattttg caagaacttt ggtcaatggt aatattgatc ttgcttaaaa aaagtaaagg     480
ggagatctta cttgcataag tttctggaga tcagcttgac cacctacggg gttagtcatt     540
ccggggatct ggtagccgcc ggggtttgac caatttgcag aagctacgtt aagagcatta    600
gcaatagctt gttgattcac gccgtttgga gtgcctccag cagctttcgc tgcagccatg    660
taaagggctt gctgctgagc gagcatagca acctgttgct gatgcatggc aaaaggcgat    720
actatattcg tctgtaatca aatagaaacac acagagttat atcacttgaa ctgctctgg    780 tgttccaaat gtcccgtgtt gaagaaatca tagtaagtga taacaaaaca caaatcatat     840
cattcgctat atttgtaaat gtaagttaaa taatgataca aaaacgaaac ttggaaagct    900
gaatatcaac aaagcagtga atctgagaa gcgtatataa ttaactaata atttaccttc     960
tcaaacaggc tcatgatatc gcctttcaca tcttttggtg cttgttgagt tgttaaatta    1020
ggtgtgtcct aaacaaatc ctcaaagtca gaagatgaag ctggaggaga actgctctca     1080
gcaggcttgg ctgtgacaat tttctctgcc gtttgaccac ttccagcagc tacagttta    1140 ggattcagaa attaatctat tactccaaag cattttcaaa agaagaacaa ttgacataaa    1200
gttaacaagg ataggaaaaa tgtgccacga tgttagatta tcacatgcta gatagataca    1260
tacactgaaa gccagcccat gagttatcat cggcaggagt atcgccagga gttgcctctg    1320
aggtatttgt agtcgaatca tccattgata gcatgttaaa cagatcagta gcaaaatcca    1380
cctttggagg atctgatgct ggtgcaacat ttactgcttg tttctccctc tctactggag    1440
tagctgcaga ctccatttc tgctgtggct ttataacctg tcattttag catcatgtat      1500 cagaaaaacc agggtttgga tactgtaaga aagacacgtt gacagattat gaggctctaa    1560
aaacacagtg agtaaaataa tgatctgaca gctacagcat atgcattgac aaaaataatg    1620
```

```
atctcatagc tgatatccta agattattaa ataagatcaa ggaatacgga tccttaatac    1680
tgatgagtaa ctaaaggtat ggctctttag ttatacagat cttctgagaa gtatgtttgg    1740
tacctgactg ggtccttggg gaggcacggg aagatttatt ctcgttgcag caacattatt    1800
tcttgttcta gatgctggaa tagttttcct ctcctcaaac aaatttacag gactactact    1860
atgtccatgc tcatatcccg gcccacttct ctccacagat ttccgccgtt cctgctcgac    1920
tctaggaggt gatctagcct tttcccctct agaaacccat ctcttctctt catacctaga    1980
aaagtcatat gtcataagaa tgatttcaac gtccatatga atagcaagat agacaattca    2040
atgaggtgga actaactgaa aagtttgtat aatgaaaaag agagatacat actttgcacg    2100
tataaaattc tcaattccaa ctctatcata gtttgggggt agctctgctt cccagtaact    2160
atttgcttta tcatttccca ttgctgcatg caaataaaag attatatact ttacattgcg    2220
taacaaccca tgaatcagcc atagagcatt tagtttaaaa gacacttaca ctgtataaat    2280
gcaacctgct cggggagcca tgtgtccaga gtggcagatc gaacctgcac tcattagccc    2340
agtcaggtgt tttggtagaa aataaagtag cttatgctgc taaggttaac atctacttga    2400
caaaaggaca cggctcatac aaaaatcaga gggcgaaatc aaatcatgta cttttgcaca    2460
gagttgcttg aagttcgtgt gtaaactgta tcgacgacaa tgggagtaca agaaggtggg    2520
gagatttaat gcattcatgt caaactttcc agctcttgtg atggaaaata caaaatgaaa    2580
ttgctaatac aaaaaccaaa ttgaaaattt gtgcagagaa tttgagccaa atggaatgag    2640
ttattcatcg aattaatatc tgagctttcg taaaaaaatg cagcatcaag aaaacaaatg    2700
tagaaaggaa agtgagagac taccttcgat atgtgtaccc cgagactcct gtgaatccca    2760
gaacattgca tgcagataaa gatacctaaa ttaacactag cccatcttgg acctctgcaa    2820
agcaaatgga acagtattag caaatacata catgaaccag cataataatg ctgaaaattc    2880
acatcaggta gaaaactata ctttgttttg cagtcagcac attctctgtt ctctggatgt    2940
ttaagaagcc cttcaagaat ctgcagataa gtagcaccaa atcaaatga atattcaagc    3000 aatagactac ataaacgaaa aaatcatacg tcgcaaaaca taagaagaa tctacacata    3060 caaaatatag agtatctcaa gaaaacttca aaattatcag aattgacatg tttaactaac    3120
caaaatgaat caaagttctc attgcagtat gagataagtt tcgtcaatga atgaacacca    3180
aagttctcga agactcgaca tacaacatca ttcctaatat cctatacatg tatgcatcac    3240
caatcccaca aagctatccc aactacaact aatagtttca acatggcaaa taactcaaag    3300
actaccaagc acaaatgaaa atccctatgg gacgctaagc tccttggatc cctgtgttcg    3360
attctttcca aaatcaaaca attgaatacg aatttctata ggaaaacact agaattcaag    3420
ctccatgaaa ctgtaacatt caataagccg acgttgaata taaaacaatt caaaaacccg    3480
atcgtgatca actattgtcc tagacaacaa atcgaaatag agaaactgat tttcattgct    3540
gatgaataat aattctagct caatcgatcg aagaagataa ggatcgacga tacaaatcct    3600
ctcctaacta gaggaaaccg aagaaaatga aggaaggata gctgctaatg cacagatcca    3660
atcgaattaa gatcgatcat atattgttgg caaccaaatt caaatatatg acgacaaatc    3720
cacaaagctc ggagaaaata aaataagaga atctgagatt cgagattaga gagagacctt    3780
tctatggcgg gcattaagct ccttagagac gttggctttc tcgttcatgg cggatagata    3840
aaatcaaaag aaggagaatc ggagaaagag gaagaagaag agctgaagaa aaatgatcta    3900
cggagacgac gaggtcaaaa tagtcttttc cgccttcagc gctcttcaat atctctctct    3960
```

```
tcttcttcct ctccgaaaat taaaaatcct tttttctttg ccctttgaga acgagcgacc    4020
aagagagaga gatgggtcaa tacttttttgg accgttcaga ttatggtact ggtttattaa    4080
tccggtttta gatttcattt tcaaaattga atatggttcg gtttaatttc atttcggttt    4140
aaattttcaa aaataattcg gtcactcgtg attgcagcac ctgaaaattt tcaaagaaat    4200
ctacacatga atatttgtga aagtgtaatc atataaaatt ggttaatttg tgactaagtg    4260
ggttttgatt tatcaaaaat aaggtcggtt tatttggcgg tttaagtggt ttttttgatt    4320
ggtcatatat aagcattaga gtgttgcggg tggaaaataa atcacatggc catctcatca    4380
cctgttatgt ctgtatccac tttggagtgg ttgttgtatt gattccaatt tctttgttta    4440
tttatgtgat gtttatggga catattttat ttgctaagat ttttatttga tgtgacgatg    4500
agtcaacgaa tgttccaacc aacacaaatt tcaatttaaa cccaaaaaaa taattatatt    4560
attatctctt agattcctaa tttttcaaac tgatatttgt ttgtcaatac gaactataat    4620
cctaacattc gacaaactct aatttaatag gtatacatta ggaactataa tacattgtgt    4680
gtgaataaac ctaaaaaagt tttgtagtct aatgagaagt ggtctctcgc tggctctaaa    4740
cctcataatc ggtttggtct aagtagcacc tttacttatc tgtatgtgga atatcatcgg    4800
gagttatcac aaatataatc ccaaagcctt ttgaaatttc taacttctct aacttcatcc    4860
acatatatat actttccaat tttgaaaata tatagatcca cttagtatat ttccatttta    4920
agtcgccatt agaagagagt tatgctacca actttggcaa ttaatatgct ttttagggga    4980
tgtgacgtcg cgattatgat gggatgagct tggaaatata tgatcatcat agccatctct    5040
ctttgttatc agtgcgagga ccaacttttc aggaggatat ttgcacatct agaaggaaga    5100
tttttctcat atagtaaata gacgactgct tatttttgct tctcgaatta ctctccatag    5160
cctctcttca gtattctca gatctcaaac cctctgacac gtatagagac ttccccacat    5220
tttgcaaact ttaatttctt cttaatcaga cttagcttca agctttatct caatcatgta    5280
catctcacat tgttttttcta aaatttgagg atattgattc tggagtatgt attgttatgt    5340
aaataagtat ttataattaa atcaagtata tggaaaatat attcgaagaa acaaacttca    5400
tataataagg tttgaacgtg gttaattaaa atgatatcca attaagattg tatcggatct    5460
tggtggttat ttatgtgaac atctcaacaa ctagggtttt gttttgttta ctctttctta    5520
tttgattctc ttgcagcctc gctttcccct aaaacacttc ttatcaatgg cgctgcttct    5580
```

<210> SEQ ID NO 9
<211> LENGTH: 2160
<212> TYPE: DNA
<213> ORGANISM: Arabidopsis thaliana

<400> SEQUENCE: 9

```
tctgcaacca attcaaaggt cgacaacttc ctgaaaggat ccatttaaaa ctcaaataag      60
taacaacatc tcaaccatgt gaaagtgtaa tgatgcttca attgttcttt taccattatg     120
acgattttga atgtaactcg tatataaaga tcttagatat gaaagggctc tgattgatga     180
ttgtcaaaac agtttaaaac cgcagactta cgtggggtaa gaacacaaaa atagattttt     240
gctgtaaccc tttaggctca gacgagagaa gatgctaacc tgagctgagg aaaatgaagg     300
taaaggaggg gttttggtg attgccgat tgtgacgccg gtgataggag cgattagcac      360
cgagaaggga tgaaaaaacg attctttcaa ttgggttatc gaaggaatct tcgtatgagc     420
atagtgatca agtcgggttt tcgagagcta gggatttgaa tttattgctt tgctttgact     480
ccatgttgga ttaaaaatag agagatgatg tgtcgcagtg acagatataa aagggtacga     540
```

-continued

```
gaaaccgtca tttctttcct ctcctctcct tcaaatccgt tcttccttga aaccattttg    600
gctctctgtt tacaaacttg gtttgatttt tcaattgcct ctgtttctct ctcattctct    660
gattcatctt catcagaatg aacaggaagg cctctgtttc caaggagctc aacgccaagc    720
attcaaaggt cccatctttt tttctcctcc ttttcgattt ttcaccattg gttttgcgtc    780
tggaaagttg aaaggttaga gattttgtgt gggttataga tattggaagc acttttgaag    840
catccagaca atcgagaatg tgcagattgt agatcaaagt aagcatcttg ataacattat    900
ctctttcatg atcatgtaag aaaaacgatt taggagcatt gtgttgtttg gatctatcta    960
ttttacaggg caccaagatg ggcaagtgtg aaccttggga tattcatttg tatgcaatgt   1020
tctggaatcc atcgtagcct ggcgtccac atctctcagg tccctaaata atctctcttt    1080
taattgattg tgttgtaaat ggatcataca aattagggat actgatgaat tttggacaca   1140
ggtaaggtct ataactctgg atacatggct tccagatcag gttgctttca tgaaatgtaa   1200
gctcctcttt tgtatataat gaacacattc agtagttgaa ttttgtatca atcccatagc   1260
ttgatcatct tattctcggt ctagctaccg gtaatgctaa gggaaatgag tattgggaat   1320
cagaattgcc tcaacatttc gagagaagtt caagcgacac gtttataaga gccaagtatt   1380
gattcttttc tatgttcgct tttgcttcct catctgctac aacacaactt tagcttgaat   1440 cttttttct tctgttcgtg tgtgttttag atacagtgag aagagatggg tttcaccggg    1500
agcgattcaa ccggctccta tagttagcca gctaagctgc aaagttagtc acttggtaga   1560
gagtggatat aaacctgaaa ctccaaagaa agctagaact ctttcacttg acgaagagat   1620
ccttcttcat catgttcttc aagtaacacc tccagaaacg agaactcgtg cggtatgaca   1680
acaaatctat atcttttgg gttctggtat gatcactaga ttggaaattc attcagtttc    1740
cttgtttgtc ctgtggcaag aattaacaaa gcttttgtag aaggattttg aatcatttcc   1800
ataaactgtt gtgcaatgca gggttcggta gatatgaagg agaatgtata tgttgtacct   1860
ctaccagaat tcaagaaacc aaatcaaaag aatgagaatt tctccagtga agtaaaccag   1920
aatagaagaa ccaccatagc accaccgtcg agctgggcta ctttcgactg taaggccatg   1980
attcaggctt tctttttttt tatcttctgt tagttttgag gttttgattc taaatctcta   2040
atgtgaaaca ggaagagaaa agactctatg aagacgaaga agatggaggt tttgaaaaaa   2100
caagaatcat catgtgggct ttaattttag tcaaaaggtt ggcaaagatg ggatgatgaa   2160
```

<210> SEQ ID NO 10
<211> LENGTH: 247
<212> TYPE: PRT
<213> ORGANISM: Arabidopsis thaliana

<400> SEQUENCE: 10

```
Met Asn Arg Lys Ala Ser Val Ser Lys Glu Leu Asn Ala Lys His Ser
 1               5                  10                  15

Lys Ile Leu Glu Ala Leu Leu Lys His Pro Asp Asn Arg Glu Cys Ala
            20                  25                  30

Asp Cys Arg Ser Lys Ala Pro Arg Trp Ala Ser Val Asn Leu Gly Ile
        35                  40                  45

Phe Ile Cys Met Gln Cys Ser Gly Ile His Arg Ser Leu Gly Val His
    50                  55                  60

Ile Ser Gln Val Arg Ser Ile Thr Leu Asp Thr Trp Leu Pro Asp Gln
65                  70                  75                  80

Val Ala Phe Met Lys Ser Thr Gly Asn Ala Lys Gly Asn Glu Tyr Trp
```

-continued

```
                    85                   90                   95
Glu Ser Glu Leu Pro Gln His Phe Glu Arg Ser Ser Asp Thr Phe
                100                 105                 110
Ile Arg Ala Lys Tyr Ser Glu Lys Arg Trp Val Ser Pro Gly Ala Ile
            115                 120                 125
Gln Pro Ala Pro Ile Val Ser Gln Leu Ser Cys Lys Val Ser His Leu
    130                 135                 140
Val Glu Ser Gly Tyr Lys Pro Glu Thr Pro Lys Lys Ala Arg Thr Leu
145                 150                 155                 160
Ser Leu Asp Glu Glu Ile Leu Leu His His Val Leu Gln Val Thr Pro
                165                 170                 175
Pro Glu Thr Arg Thr Arg Ala Gly Ser Val Asp Met Lys Glu Asn Val
            180                 185                 190
Tyr Val Val Pro Leu Pro Glu Phe Lys Lys Pro Asn Gln Lys Asn Glu
        195                 200                 205
Asn Phe Ser Ser Glu Glu Lys Arg Leu Tyr Glu Asp Glu Glu Asp
    210                 215                 220
Gly Gly Phe Gly Lys Thr Arg Ile Ile Met Trp Ala Leu Ile Leu Val
225                 230                 235                 240
Lys Arg Leu Ala Lys Met Gly
                245
```

<210> SEQ ID NO 11
<211> LENGTH: 3180
<212> TYPE: DNA
<213> ORGANISM: Arabidopsis thaliana

<400> SEQUENCE: 11

```
gctgagacta ttaaacccca acatatgaa tcagattcca aaaatagag aatccctacg      60
atgattaaga tgcagtctct caattttccc gcgcgttttt cttcgtcttt cccggttaac     120
aactttacgt cgtcgtttca caatcataaa aattaaacgg ttccgatgtg atgatacgga     180
tgacaacaga tccaacggtc tatatgtgat gttcacaaaa tcacatggct gtgacagaaa     240
gactgtgacg gctatggcct attgagattt gttaattggg ggagttgaga tttctcagct     300
gttgttaggg atttgtatga atgttctaa ttgtttgaat gaatgaatca aatgttataa     360
tttgtgcatt ggaaaataat atataactag agttgaaaag cttctaatga gcattattgt     420
tctaaaaaga tagtcaacag ggagataaca aggatttgag ttcaaaagaa aagaaagaaa     480
aagatacaac aattcagaat gaaagagtaa attctggtaa ctgtgacttt gctgggattt     540
ggctactcta ccgtaccaga cacgtggacc ggaataatgt gaagctgaac aattcctcaa     600
gtccatgctt catgaagtgt tctgccgctt tttggccttt agttatgtta ataagactct     660
acattaggtt cacctgttgg acaattccag taccaatctt tttttatctg cttattagtg     720
aaaaataaaa gaatatcatc aaagactat ggtttaaaac agtgcaatgc ataacaatca     780
atgaacaaga acaaaccctt gacactcaga atctgtccct gcttcatcac ttcagttaat     840
tccttcttca gacccccatc agttgttctc ccgttcatat tcacagcaag gacatttggt     900
gtcttaatgc tcacctggac tttaaactga cttccacaag ttagggttga gcggaagaag     960
aaaacgagag tagttttagt ttttttggtt gttccttcca gacccggccc gatatcgaag    1020
cgaccaaagc ccatgctttt tgagcaaaca cgttttagc agagaccttg gaaatattga    1080
gtgaagctct cacgtgacaa aaacacgcac aaaattattc aagttaccac gtttattaag    1140
caaaacgatt gagccaaaaa aaacgcatca gaatctggaa cctggatcag atctagtcag    1200
```

-continued

```
gggtcagatc ggagagccgg caatataatg gcagcggcga gacgattacg gacgctccaa    1260
tctcagccgg agaacaaggt ctgtgtcgat tgctcccaga gaatccaca atgggcatcg     1320 atttcatatg gaatcttcat gtgcttggaa tgctccggta agcaccgtgg tttaggtgtt    1380
cacatctcat tcgtcagatc cgtcaccatg gattcatggt ccgagatcca gatcaagaaa    1440
atggacgctg gaggcaacga gcgtctcaac aattttctcg ctcagtacgg gatctcgaaa    1500
gagactgata tcatctccaa gtacaattcc aacgccgcgt ctgtgtatcg agatcggatc    1560
caagctttag ctgagggaag acaatggaga gatccgccga ttgttaagga atcggttggt    1620
ggtggattga tgaataagaa gcctccgttg tctcaaggcg gtggtagaga ttctggtaat    1680
ggtggatggg ataattggga taacgatgat tcgtttagat ctacggatat gaggaggaat    1740
caatcggcgg gtgatttag gtcatcggga ggtcgtggtg ctccggcgaa gtcgaaatcg     1800
tctgaggata tatattcacg gtctcagctg gaggcgtcgg cggcgaataa ggagagtttc    1860
tttgcgaaaa ggatggctga gaatgagtct aagcctgagg gacttcctcc ttcacaaggt    1920
ggtaagtatg ttgggtttgg atctagtcca ggtccagctc cgagaagcaa tcaacagagt    1980
ggtggtggtg atgttttctc tgttatgtct gaggtaaatt tggaagcttt ttgagagtga    2040
tttggttaga tgcgacatgc gagtgacttc tctgtttatc ctgtaaatga atgtgtttgt    2100
tttacgcgta tatgcttata gggttttgga agattgtctc ttgttgctgc atcagctgca    2160
aatgttgttc agactggaac catggagttt acttccaagg tacttctttt atcatttctg    2220
cttcgatgtt gtggttgatt cgtttgcatc gtgatcagta agctcactcc ttggtaacat    2280
tctgtagtct agttgttaag tttatattga gatcgtgact attcgcttgg tgtctgtcta    2340
attgccgcta tgctcattgc tctgtttgtt agattatccc attttgaca ttgttatgta     2400 acacaaaatt agagtctttt ctagctgcat aatcttctta ctttaattgc agtgttaaag    2460
ctcttttttt tttttttgt ctttatgccc ctgcaaaatc tctagggaga tcctctaaaa     2520
cgctgaactg agcataatgc cggatgctcg tccttctttt caaatactgc taacattaga    2580
aattatagaa ttttgaagac aagtgagata agaaaccttt gttcattgtg caggtcaaag    2640
aaggtggctt agatcagacg gtcagtgaga ctgttaatgt tgttgcgagt aagacaacag    2700
agataggaca gaggacatgg gggatcatga aaggagtgat ggcaattgcc tcacaaaagg    2760
ttgaagagtt cactaaagaa gaagcatcaa cttggaatca acagaataaa actgagggca    2820
acggttacta ccagaactct gggattggaa acaaaacagc aaattcatct tttggaggat    2880
cacaatcatc atcaagtggt cacaacaaca gttatcgtaa ctcgaattct tgggatgact    2940
ggggagaaga gaacaatagc aaaaaggaag cagcaccaaa ggtgtcgact tctaatgatg    3000
atgacgacgg cggttgggct ggttgggatg ataatgatgc taaagatgat gatttctatt    3060
atcagcctgc aagcgataag aaatctgtag gtcacaatgg gaaatcagac actgcttgga    3120
ccggtggagg ttttctctaa cggtaagcac caaatcaagt taaacgaatc gaatatgtaa    3180
```

```
<210> SEQ ID NO 12
<211> LENGTH: 456
<212> TYPE: PRT
<213> ORGANISM: Arabidopsis thaliana

<400> SEQUENCE: 12
```

Met Ala Ala Ala Arg Arg Leu Arg Thr Leu Gln Ser Gln Pro Glu Asn
1             5               10              15

Lys Val Cys Val Asp Cys Ser Gln Lys Asn Pro Gln Trp Ala Ser Ile

```
                  20                  25                  30
Ser Tyr Gly Ile Phe Met Cys Leu Glu Cys Ser Gly Lys His Arg Gly
                35                  40                  45
Leu Gly Val His Ile Ser Phe Val Arg Ser Val Thr Met Asp Ser Trp
 50                  55                  60
Ser Glu Ile Gln Ile Lys Lys Met Asp Ala Gly Asn Glu Arg Leu
 65                  70                  75                  80
Asn Asn Phe Leu Ala Gln Tyr Gly Ile Ser Lys Glu Thr Asp Ile Ile
                85                  90                  95
Ser Lys Tyr Asn Ser Asn Ala Ala Ser Val Tyr Arg Asp Arg Ile Gln
                100                 105                 110
Ala Leu Ala Glu Gly Arg Gln Trp Arg Asp Pro Pro Ile Val Lys Glu
                115                 120                 125
Ser Val Gly Gly Gly Leu Met Asn Lys Lys Pro Pro Leu Ser Gln Gly
                130                 135                 140
Gly Gly Arg Asp Ser Gly Asn Gly Gly Trp Asp Asn Trp Asp Asn Asp
145                 150                 155                 160
Asp Ser Phe Arg Ser Thr Asp Met Arg Arg Asn Gln Ser Ala Gly Asp
                165                 170                 175
Phe Arg Ser Ser Gly Gly Arg Gly Ala Pro Ala Lys Ser Lys Ser Ser
                180                 185                 190
Glu Asp Ile Tyr Ser Arg Ser Gln Leu Glu Ala Ser Ala Ala Asn Lys
                195                 200                 205
Glu Ser Phe Phe Ala Lys Arg Met Ala Glu Asn Glu Ser Lys Pro Glu
                210                 215                 220
Gly Leu Pro Pro Ser Gln Gly Gly Lys Tyr Val Gly Phe Gly Ser Ser
225                 230                 235                 240
Pro Gly Pro Ala Pro Arg Ser Asn Gln Gln Ser Gly Gly Asp Val
                245                 250                 255
Phe Ser Val Met Ser Glu Gly Phe Gly Arg Leu Ser Leu Val Ala Ala
                260                 265                 270
Ser Ala Ala Asn Val Val Gln Thr Gly Thr Met Glu Phe Thr Ser Lys
                275                 280                 285
Val Lys Glu Gly Gly Leu Asp Gln Thr Val Ser Glu Thr Val Asn Val
                290                 295                 300
Val Ala Ser Lys Thr Thr Glu Ile Gly Gln Arg Thr Trp Gly Ile Met
305                 310                 315                 320
Lys Gly Val Met Ala Ile Ala Ser Gln Lys Val Glu Glu Phe Thr Lys
                325                 330                 335
Glu Glu Ala Ser Thr Trp Asn Gln Gln Asn Lys Thr Glu Gly Asn Gly
                340                 345                 350
Tyr Tyr Gln Asn Ser Gly Ile Gly Asn Lys Thr Ala Asn Ser Ser Phe
                355                 360                 365
Gly Gly Ser Gln Ser Ser Ser Gly His Asn Asn Ser Tyr Arg Asn
                370                 375                 380
Ser Asn Ser Trp Asp Asp Trp Gly Glu Glu Asn Asn Ser Lys Lys Glu
385                 390                 395                 400
Ala Ala Pro Lys Val Ser Thr Ser Asn Asp Asp Asp Gly Gly Trp
                405                 410                 415
Ala Gly Trp Asp Asp Asn Asp Ala Lys Asp Asp Phe Tyr Tyr Gln
                420                 425                 430
Pro Ala Ser Asp Lys Lys Ser Val Gly His Asn Gly Lys Ser Asp Thr
                435                 440                 445
```

Ala Trp Thr Gly Gly Gly Phe Leu
    450             455

<210> SEQ ID NO 13
<211> LENGTH: 3000
<212> TYPE: DNA
<213> ORGANISM: Arabidopsis thaliana

<400> SEQUENCE: 13

| | | | | |
|---|---|---|---|---|
| ttatgaatga gaaggtacaa gtatatattt gtcctaattt gctctgtttt ttgttgttgt | 60 |
| caatgtgtaa aagttgtaaa tgaaaatctt gtcttatact agtttgttat atcatatatt | 120 |
| ggaatgtgtt ttggtatcat ctatggggtt ttctgtgttt aatattgtcg aacacctaag | 180 |
| atggggcatg attgttgata tgaaaagct atgcgacttc ctcaggttct ttttctgtat | 240 |
| taaaaattaa gttagttctt tgttagatta ggcaccaact atataataat tcaaagaatg | 300 |
| acaatgatga ggcaactact tctatgagcc aaatccaaaa gtaaaaactc tttaaaataa | 360 |
| cgtcaatatt taataatggt aaaaccaaac acaacctaat gcattttatt gatttatttg | 420 |
| tacagccaat cacaactta gtttctaaat taagagattt ttataaggct gttttgtaa | 480 |
| aaaaagaag taattaaatg ttgtgataat tgttttaatg acgtgtcaac tacaatatt | 540 |
| gcacgaaatt gaaaatcaca aaatcgaaaa tccactttt tgttttgttt ctctctttgg | 600 |
| ccgacaaata aaaaaaaaac aaaaaacaca actaatcata ggcttctcca tcttcttgtc | 660 |
| tgcaggatga tgcaattttt cagacaattt tcttccaaaa tcttttcgta attctgtttt | 720 |
| attttcaac gttttaggtt tttaccaatc cgccgtagtt atatccaaca ttaattttt | 780 |
| tccctcttct cagaaaaaaa taaaattcaa ctcatctcta gagttttag gttcttccaa | 840 |
| gaaattgaat ttggaaggag gctttgatgg gtttgaattt tccataatcg tcccttgttt | 900 |
| acggtatttt tctcaaggaa tccctgaaaa actatttctt ggtctttgtg taattgtctg | 960 |
| gtgcaaatca agttattgtt tttatcttgt gttgttgatt cagactcttg ttgtttgaaa | 1020 |
| atgctatggc tcgtgagggg atgttgtttt gattttggga aagtcttgtt tgaatggtca | 1080 |
| cggctttct gaacattcgc gtgttctttc ttgtctcggc tctgcttcga aatgtctctc | 1140 |
| ggccaagaaa atgttgatcc tgttgaagtt tcaggtaaaa tcctacacaa tcctttaata | 1200 |
| attattatcc accaagtttt taaacttgta aaggtttcaa attttttgcct ttttgtttta | 1260 |
| tagggtcgca tgcttgctta tatgaacttt tatgttctga acacccaaa tggactcctc | 1320 |
| ttagggttga agatttgcaa acatcttctt ctggtaatta ttacttaatg atggagataa | 1380 |
| acattcttaa gatatgtttt aagtgttagt tggagacaat ctcatgtcct gtttgttttg | 1440 |
| ttttagatcc cagagatcgg ttggagaagt tgctgaagca acctgggaat aaatattgtg | 1500 |
| ctgactgtgg ctctcctgaa ccaaaatggg tgtaagttga ttaatacttc tgtgttgttt | 1560 |
| gtacatttct tttgatgaac tggattgatt catttcattt cgttttagat cgttgagtct | 1620 |
| tggtgtattt atctgcatta agtgttctgg tgtacacaga agtcttggag ttcatatatc | 1680 |
| aaaggtactt tctttttcata gacaatcttg attttttctct gcttctgtgt gtttctagag | 1740 |
| tcttttatcg ataaatttga ttgaatgatg atcgcaggtt ctatcagtaa agctagacga | 1800 |
| gtggacagat gatcaggttg acatgcttgt aggttacggt ggaaacacgg cagtgaacga | 1860 |
| aagattcgaa gcttgcaaca tcgaccagtc aaagaaacca aaaccagatt ctactaatga | 1920 |
| ggaacgaaat gatttcatta ggtgacattt tttacttaac aatttgttat aatggtattg | 1980 |
| tatgtataat catcttgtcc ctaaatctttt aaatctttca gaaaaaaata tgagcagcac | 2040 |

-continued

```
cagtttatgg atccaaagga tggtgctttg tgcacttatc agcagcctag cagaacaaac    2100
acttcaccac cgtctttatg ttctgcaagc caccgttcta caaaaaaccg tattggtcat    2160
gcatttagga atagctgggg aagaagagaa tctgatcaca aaggaccaaa gaagagcaat    2220
tccatggtaa caatcactat acatacatac atacatgttt gggtagttac tgttgccaac    2280
gttagttaat ttttgtgggt gttttatagg caggtatggt tgagtttgtg gggttgatta    2340
aggttaacgt ggtaaaagga accaaccttg cggttcgaga cgtgatgacc agcgatcctt    2400
atgttatcct tgctcttggc caacaagtga gctctctacc aaatctctct agacttgtat    2460
gatttgaagt taacctcggt ctttttcaat gtttgtttgt tgtagtcggt aaaaacacgg    2520
gtgataaaga acaacttgaa tcctgtgtgg aatgagacgc taatgctttc gatacccgag    2580
cccatgcctc ctctcaaagt ggtaagaaca gagagctttt ccaaactcgg ataaacacta    2640
ctactgaacc gagcttgata tgtaaatttt ttgcagctag tgtacgacaa ggatacattc    2700
tcgacagatg atttcatggg agaggcagag atagacatac aaccattggt gagtgcagca    2760
aaagcatacg agacatcgag cataaaggaa ccgatgcagc tgggaagttg ggtggcgagc    2820
aaagagaaca cattggtgag tgatggcata atcttacttg aagacgggaa agtgaaacaa    2880
gacatttcac ttaggctaca aaatgttgaa agaggtgttc ttgagatcca gcttgaatgt    2940
cttcctctca ctcaatgatg atactttctt cttcatccct cttctttttt tttttcttta    3000
```

<210> SEQ ID NO 14
<211> LENGTH: 373
<212> TYPE: PRT
<213> ORGANISM: Arabidopsis thaliana

<400> SEQUENCE: 14

```
Met Ala Arg Ser His Ala Cys Leu Tyr Glu Leu Leu Cys Ser Glu Thr
 1               5                  10                  15

Pro Lys Trp Thr Pro Leu Arg Val Glu Asp Leu Gln Thr Ser Ser Ser
            20                  25                  30

Asp Pro Arg Asp Arg Leu Glu Lys Leu Leu Lys Gln Pro Gly Asn Lys
        35                  40                  45

Tyr Cys Ala Asp Cys Gly Ser Pro Glu Pro Lys Trp Val Ser Leu Ser
    50                  55                  60

Leu Gly Val Phe Ile Cys Ile Lys Cys Ser Gly Val His Arg Ser Leu
65                  70                  75                  80

Gly Val His Ile Ser Lys Val Leu Ser Val Lys Leu Asp Glu Trp Thr
                85                  90                  95

Asp Asp Gln Val Asp Met Leu Val Gly Tyr Gly Gly Asn Thr Ala Val
            100                 105                 110

Asn Glu Arg Phe Glu Ala Cys Asn Ile Asp Gln Ser Lys Lys Pro Lys
        115                 120                 125

Pro Asp Ser Thr Asn Glu Glu Arg Asn Asp Phe Ile Arg Lys Lys Tyr
    130                 135                 140

Glu Gln His Gln Phe Met Asp Pro Lys Asp Gly Ala Leu Cys Thr Tyr
145                 150                 155                 160

Gln Gln Pro Ser Arg Thr Asn Thr Ser Pro Ser Leu Cys Ser Ala
                165                 170                 175

Ser His Arg Ser Thr Lys Asn Arg Ile Gly His Ala Phe Arg Asn Ser
            180                 185                 190

Trp Gly Arg Arg Glu Ser Asp His Lys Gly Pro Lys Lys Ser Asn Ser
        195                 200                 205
```

-continued

```
Met Ala Gly Met Val Glu Phe Val Gly Leu Ile Lys Val Asn Val Val
    210                 215                 220
Lys Gly Thr Asn Leu Ala Val Arg Asp Val Met Thr Ser Asp Pro Tyr
225                 230                 235                 240
Val Ile Leu Ala Leu Gly Gln Gln Ser Val Lys Thr Arg Val Ile Lys
                245                 250                 255
Asn Asn Leu Asn Pro Val Trp Asn Glu Thr Leu Met Leu Ser Ile Pro
            260                 265                 270
Glu Pro Met Pro Pro Leu Lys Val Leu Val Tyr Asp Lys Asp Thr Phe
        275                 280                 285
Ser Thr Asp Asp Phe Met Gly Glu Ala Glu Ile Asp Ile Gln Pro Leu
    290                 295                 300
Val Ser Ala Ala Lys Ala Tyr Glu Thr Ser Ser Ile Lys Glu Pro Met
305                 310                 315                 320
Gln Leu Gly Ser Trp Val Ala Ser Lys Glu Asn Thr Leu Val Ser Asp
                325                 330                 335
Gly Ile Ile Leu Leu Glu Asp Gly Lys Val Lys Gln Asp Ile Ser Leu
            340                 345                 350
Arg Leu Gln Asn Val Glu Arg Gly Val Leu Glu Ile Gln Leu Glu Cys
        355                 360                 365
Leu Pro Leu Thr Gln
    370

<210> SEQ ID NO 15
<211> LENGTH: 5640
<212> TYPE: DNA
<213> ORGANISM: Arabidopsis thaliana

<400> SEQUENCE: 15
tgtcgtacgt taaaaattac actctaaccc cacacacact aactatttac aattttacca        60
taataatctt cttaatttac aattctgcca tcgtcttctt cttcagggag ggattttgtt       120
aggaccatcg gctttaggta gaaacatggc gtacatggac cgtatatttc cgaaatggag       180
tatgccgata ctcgaatccg tcgcgagcat aggacttctc ttcttcctct tcctcgtcgg       240
tctagaactc gatttatcat cgatccgacg aagcggcaaa cgcgctttcg gaatcgcagt       300
cgctggaatt acactaccgt ttatcgccgg cgtcggagtc gcgtttgtga tccgtaacac       360
tctctacacc gccgcggata aaccaggtta cgccgagttt ctcgttttca tgggagtcgc       420
actctcgatc acagcttttc cggtacttgc gcgtatttta gcagagctca gcttttaac        480 gactcagata ggagaaaccg cgatggctgc agccgctttt aacgatgtag ccgcgtggat       540
tttactcgct ttagcggttg cgttagcggg taatggcggt gagggaggtg gagagaaaaa       600
gagtccgtta gtgtcgttgt gggttttgtt atcgggcgct gggtttgtgg tttttatgtt       660
ggttgtgatc cgacccggaa tgaaatgggt cgcgaaacgt ggatctcctg aaaacgacgt       720
cgtacgcgag tcttacgtgt gttttgacgtt agccggtgtt atggttttccg gtttcgcgac       780 ggatttaatt gggattcatt cgattttttgg agcgtttgtt ttcggtttga ctataccgaa       840
agatggagag tttggtcagc gattgattga acgaattgag gatttttgttt ccggtttact       900 cttaccgctt tatttcgcta cgagtggttt gaagactgac gtggctaaga ttagaggagc       960
tgagtcgtgg gggatgttgg gtcttgttgt tgttacggct tgtgccggga agatagtcgg      1020
aacttttgtt gtggcggtga tggttaaagt tccggcgaga gaggcgttga cacttggttt      1080
cttgatgaat actaaaggtt tagtggagct cattgtactc aacataggca aggagaaaaa      1140
```

-continued

```
ggttagtttt gtcttccttt tttctgattt tttaaggttc ttgtttacgc ttttagttat    1200
ctgatgaata ttataaatat aaaaaaccta gtaacactaa agttatttga tcatgtttag    1260
tggataaagc atataaaaca aaatacgatt attatattga tttaatcgca tctataccat    1320
tattttaggg tgtttagata tatttaaaaa tttaggttct agttggatcc atgtgtatat    1380
gcgtccggtc cgctcaatat tggtaggctg gtcggggatc cggaatagta aaattgctta    1440
tgttttattt gaacattaac caaccgttgt ataaattcaa attgatagct aggcaggccc    1500
ggctctaggg gagtgccaga ggtgctagta cacagggtcc tcattttttt ttcttaattt    1560
taagtcttct agtttgcagt ttttttttttt ttaagggggaa aactacaaaa aaaacaacca   1620
ccaaaataaa agataataag tttaaaataa aaatacagta aacacatgtc acataaagtt    1680
attttgttta gatttaaggg ctattttgt ttgtagcaca gggcccaata aaatattgag    1740
ccgggctgct aggtttacta tcactataat agacacggtt gcaatttgat agctaggttt    1800
gctctcaacc gttgtatagt aatattagtc accataatac aaatctgcag ttcattaatc    1860
atagactgat ggacacggtt gcaatttgat agctaagttt actatgtgca tcgaagatga    1920
tgcagttagc aatggtagct tcaaaacatt agtccgtgat tcttttgtca cctccgaaat    1980 aaacatttttt atcttaaata tatgtgcaag attatactat aatgcttctg gaaatatgta    2040
gtatataaaa ttttttgttt aaacgtgtct tcccaacaaa gattatagtt atatactaca    2100
cttttattat aaaggcgttt cttattgttt tggggtaata agaaaaaact gatcaattaa    2160
ggactagtca tatatatgca tgcatgaaaa cttttatttt atttttttttt ctgcatgaaa    2220 actttatacg aatataccat ttcgaatggg ccaatgttta cgtaatcgtc acttactgat    2280
ccacttgcag atttatgatc ttcttcataa tgcaacaata aagtgaaata atgattaccc    2340
attaatgtag taagtgtggt tatttttaat taaactgttt gtacgcgggg ttgactttaa    2400
ccaggtacta aacgacgaga cgtttgcaat actagtgcta atggcactct tcacaacgtt    2460
cataacgacg cctactgtaa tggccatttta caagccggca cgtggcaccc accgcaaact    2520
aaaagacttg tcggcgagcc aagactccac caaggaagag cttcgcatcc tagcctgcct    2580
ccacggccca gccaatgtct cctccctcat ctctctcgtc gagtccatcc gaaccaccaa    2640 ggtaaaattac cttctcttta tatttttacg ttacaataat ctatatttaa atttgtaaat    2700
ctatgataag agttatatca gaaaattaag atatcattga aatgctcaat gaaaatgtat    2760
cctacgtata attacacaca ttttgtatag ttaaaattaa aaatcagctg ggtaataatt    2820
tataatcttg gttaataatt taaaaagtcg tatttgtttt ggcagatact acggctaaag    2880
ctgtttgtga tgcatctgat ggaactaacg gaacggtctt cgtcaatcat aatggtgcaa    2940
agagcccgta aaaacggact tcctttcgtt caccgttacc gtcatggtga gcgtcacagc    3000
aacgtcatag gaggcttcga agcctatcgt caactaggcc gggtcgcagt ccggcccatc    3060
accgcagtct ctccattacc cacaatgcac gaagacattt gccacatggc agataccaag    3120
agggtcacaa tgatcatttt acctttccac aaacgatgga acgctgatca tggtcatagc    3180
caccaccacc aagacggagg aggagatgga aacgtaccgg aaaacgttgg tcatggttgg    3240
cgattggtta accaaagggt tttgaagaat gcgccgtgtt cggtggcggt tcttgtagac    3300
cgtggacttg ggtccattga ggcccaaact ttgagcttag atgggtcgaa tgtggttgaa    3360
agggtttgtg tgattttctt tggtgggcct gatgaccgtg agtctataga gctcggcggg    3420
agaatggctg agcatccggc cgttaaagtt accgttatta ggttttttggt aagagaaacg    3480
```

-continued

```
ttgaggagta ccgccgtcac tttacgaccg gcaccgtcta aaggcaagga gaagaactat    3540 gccttttaa caaccaacgt ggatccagaa aaagaaaagg taaatctctt ttgatcccct     3600
atgtttatat accagttatg acaaatataa ctatagcttt cttcttgga aaaataatta    3660 taggaattag acgaaggggc attggaagac ttcaagagca aatggaaaga aatggtggag    3720
tacaaagaaa aggaaccaaa caacatcatt gaagaaatac tgtcaatagg acagagtaaa    3780
gactttgatc taatagtggt tggaagaggg aggataccgt cggccgaggt ggcggcatta    3840
gctgagcgtc aagctgaaca tcctgagtta ggtcctatcg gagacgtgct cgcctcttcg    3900
atcaaccaca tcattccatc aatccttgtg gttcaacaac acaacaaagc tcatgtagag    3960
gatattacgg tttccaaaat tgttagtgag tcttctctaa gtattaacgg agacacaaat    4020
gtatgataac aataaataaa ttgatctagt acttaaactt cggcttaatg catggttaaa    4080
gtggttagtt gaagatgtag tttatctaca atatatagat agctcttgag taagaattgt    4140
aagatcgtct acatataaat aaccatgatt gggcatcttg ggcatcgtct acatataatt    4200
tcatatttgg actaaatagt aaatacaatt atcatttggg ccatttgaga aactaccgga    4260
aacctctcac gtgccagaga cacgtaccaa aaaaaccccc gaacatttat taggaagaag    4320
agaaaaaacg gaaaagaaaa aaaaacgcat caatctgagc agcacaagtc tgcgagattt    4380
ggattagatc tgattcaggt tggattgatc atcgttcgga gctccgggaa acatggcggc    4440
gacgagacaa ttacgaactc tccaatctca gcctgaaaac aaggtatgtg tcgattgcgc    4500
tcagaagaat cctcaatggg cgtcggtttc gtacggaatc ttcatgtgtt tggaatgctc    4560
cgggaaacac cgaggcttag gcgttacat atccttcgtc agatccgtaa ccatggattc    4620
atggtctgcg atccagatta agaaaatgga agctggtggt aacgaacggc tcaacaaatt    4680
cttcgcgcaa tacggaatcg ctaaggagac agatattatc tccaagtaca attcgaacgc    4740
tgcttctgtg tatcgtgacc ggatccaagc tttagctgaa ggtagaccat ggaatgatcc    4800
gccagttgtt aaggaagcga ataagaagcc tccgttggct cagggcggtt acggaaacaa    4860
caataacaat aacaatggag gatgggatag ttgggataac gatgattctt acaaatctga    4920
tatgagaagg aatcagtcag cgaatgattt cagggcatcg ggaaatagag aaggtgcaca    4980
tgtgaagtca aagtcgtcgg aggatatcta cacgcgatcg cagcttgagg cttctgccgc    5040
tgggaaagag agtttcttcg cgaggagaat ggcggagaat gagtctaagc ctgaaggtct    5100
tcctccttcg caaggtggca agtatgtagg attcggatca agctcggctc caccaccgag    5160
aaataatcaa caggatgatg ttttctccgt tgtttctcag gtgaattgaa tgaatgtttt    5220
gcaattcctt tttgaattcg gtgaattacg ttttgtgtgt tgattcgtgt ttaaaaattg    5280
ctaagggttt tggaagactg tctctggttg ctgcatctgc agctcagtca gctgctagtg    5340
ttgttcaaac aggaaccaag gagttcacat ccaaggtaac taactatctg tactctctgc    5400
ttgatttgca tagagtttgt gaaatatcta gttactgcgt tgcttgatgc ctcaacgaca    5460
cgtctagtga gaatctttaa ctctgtagaa agcacaattc ttagatgctc tctgtagaat    5520
tcttgtttac cataatactg ctggcaatag agttttggaa aagtggagtc aaaatcagat    5580
aagaaaccat tttattgcag gtgaaggaag gtgggtatga tcacaaggtg agtgaaactg    5640
```

<210> SEQ ID NO 16
<211> LENGTH: 459
<212> TYPE: PRT
<213> ORGANISM: Arabidopsis thaliana

<400> SEQUENCE: 16

-continued

```
Met Ala Ala Thr Arg Gln Leu Arg Thr Leu Gln Ser Gln Pro Glu Asn
  1               5                   10                  15

Lys Val Cys Val Asp Cys Ala Gln Lys Asn Pro Gln Trp Ala Ser Val
             20                  25                  30

Ser Tyr Gly Ile Phe Met Cys Leu Glu Cys Ser Gly Lys His Arg Gly
             35                  40                  45

Leu Gly Val His Ile Ser Phe Val Arg Ser Val Thr Met Asp Ser Trp
 50                  55                  60

Ser Ala Ile Gln Ile Lys Lys Met Glu Ala Gly Asn Glu Arg Leu
 65                  70                  75                  80

Asn Lys Phe Phe Ala Gln Tyr Gly Ile Ala Lys Glu Thr Asp Ile Ile
             85                  90                  95

Ser Lys Tyr Asn Ser Asn Ala Ala Ser Val Tyr Arg Asp Arg Ile Gln
             100                 105                 110

Ala Leu Ala Glu Gly Arg Pro Trp Asn Asp Pro Val Val Lys Glu
         115                 120                 125

Ala Asn Lys Lys Pro Pro Leu Ala Gln Gly Gly Tyr Gly Asn Asn Asn
 130                 135                 140

Asn Asn Asn Asn Gly Gly Trp Asp Ser Trp Asp Asn Asp Asp Ser Tyr
145                 150                 155                 160

Lys Ser Asp Met Arg Arg Asn Gln Ser Ala Asn Asp Phe Arg Ala Ser
             165                 170                 175

Gly Asn Arg Glu Gly Ala His Val Lys Ser Lys Ser Ser Glu Asp Ile
             180                 185                 190

Tyr Thr Arg Ser Gln Leu Glu Ala Ser Ala Ala Gly Lys Glu Ser Phe
         195                 200                 205

Phe Ala Arg Arg Met Ala Glu Asn Glu Ser Lys Pro Glu Gly Leu Pro
 210                 215                 220

Pro Ser Gln Gly Gly Lys Tyr Val Gly Phe Gly Ser Ser Ser Ala Pro
225                 230                 235                 240

Pro Pro Arg Asn Asn Gln Gln Asp Asp Val Phe Ser Val Val Ser Gln
             245                 250                 255

Gly Phe Gly Arg Leu Ser Leu Val Ala Ala Ser Ala Ala Gln Ser Ala
             260                 265                 270

Ala Ser Val Val Gln Thr Gly Thr Lys Glu Phe Thr Ser Lys Val Lys
             275                 280                 285

Glu Gly Gly Tyr Asp His Lys Val Ser Glu Thr Val Asn Val Val Ala
         290                 295                 300

Asn Lys Thr Thr Glu Ile Gly His Arg Thr Trp Gly Ile Met Lys Gly
305                 310                 315                 320

Val Met Ala Met Ala Thr Gln Lys Val Glu Glu Phe Thr Lys Glu Gly
             325                 330                 335

Ser Thr Ser Trp Asn Gln Gln Ser Glu Asn Gly Asn Gly Tyr Tyr
             340                 345                 350

Gln Asn Phe Gly Asn Gly Asn Lys Ala Ala Asn Ser Ser Val Gly Gly
         355                 360                 365

Gly Arg Pro Gln Ser Ser Thr Ser Gly His Tyr Asn Asn Ser Gln
         370                 375                 380

Asn Ser Asn Ser Trp Asp Ser Trp Gly Glu Asn Glu Asn Lys Lys Thr
385                 390                 395                 400

Glu Ala Val Ala Pro Lys Gly Ser Ser Ala Ser Asn Asp Asp Gly
             405                 410                 415
```

Trp Thr Gly Trp Asp Asp His Asp Ala Lys Asp Asp Gly Phe Asp Gly
            420                 425                 430

His Tyr Gln Ser Ala Gly Asp Lys Lys Ser Ala Gly His Asn Gly Lys
            435                 440                 445

Ser Asp Thr Ala Trp Thr Gly Gly Gly Phe Leu
            450                 455

<210> SEQ ID NO 17
<211> LENGTH: 4320
<212> TYPE: DNA
<213> ORGANISM: Arabidopsis thaliana

<400> SEQUENCE: 17

| | | | | | | |
|---|---|---|---|---|---|---|
| tgttgtgccg | ttcatgtgaa | catacgccgg | ttgaaaaggt | gatattttcc | ggtgaaaggt | 60 |
| gaagactttt | ttccggtgag | aagaagagag | aggtgacgtg | tagggaggaa | aaatcaaaag | 120 |
| agggaaaaag | ctaagcaaat | ggcgtttagt | gattgtttgg | agaagatgat | tctctctaca | 180 |
| atactatatt | ttatttttat | tgttttttcta | aaacaattgt | aaataatttt | ttcttatttt | 240 |
| cttaagtttt | tgttgagagt | tgcgacatat | tatatgacaa | aaaccaaacg | ataaataattt | 300 |
| ggttaactgt | tacgaaaacg | taaataaatt | attcatggag | tgataattct | cgtttggaca | 360 |
| ctgttttgtc | tgaaacataa | cttagatccg | tttattatca | catagccact | tattgtttta | 420 |
| tggagaaaaa | actaataaat | aatccattta | tggtgatata | gtgacttaga | gtttcgaata | 480 |
| tggaccaatg | ctataattca | aaatttcata | agttagaaat | ctaaaatata | aattttattt | 540 |
| ttcatataaa | ttaatatttt | aaactgcaaa | aaagaattgc | attttttaaaa | ggaaaaaaat | 600 |
| agattctact | caatttatat | caattaagtt | aggaatttaa | aataatattt | caactgattt | 660 |
| tatgttagtt | ataggaaaat | aaatatatat | gaaaaaacta | aaagtgtttt | ctttctccaa | 720 |
| tcatcttttt | tttttaaata | tcatttcatt | atgttcattt | tattaaaaat | cagtttgaac | 780 |
| cgttaatatg | aaatttacgt | tttcaaataa | ttatccggtg | taaatttttt | tttggtgtaa | 840 |
| tggttaacta | aatatccatt | aatacttcat | cacaccatat | atgaagtttg | attttcatag | 900 |
| attacaaatt | attgaagatt | aatggaaacg | atttctatct | agagatttta | gtgtggtgca | 960 |
| tagaaccgta | tgtcgtagta | cagtaccatc | tgtcaaactg | taaaattgta | caagcatcga | 1020 |
| tgtaaaacta | tcggttgtgg | agttgactac | gaaaaccata | aaaagaaaac | tcaaaaaatg | 1080 |
| atttgctagt | cctaaaaatt | atttgtaata | tatattcaaa | taataatgta | tccaacaaca | 1140 |
| tagcaacttc | cgttcaattt | ttgaaagagg | aagaaattaa | cgtataaaat | ttgtattttc | 1200 |
| tctataaaat | tcatattcga | atttattttt | tcttagacat | tttaaattgt | ttttttcttt | 1260 |
| ttttaaatat | tggaattatg | ttgtgtagcc | cactttaatt | gtttgggtcc | tctgtctagg | 1320 |
| catcgtctgt | ctgctttcca | tgtttctgtc | accataattg | acatatctat | ttattaacaa | 1380 |
| tcttcatatt | tttgtcacgg | tatactgtaa | gttttctta | accacatttt | tttcatcaaa | 1440 |
| ttttttatcg | tttggctaaa | actataatga | ccaaccaaag | tatataatttt | tttaaaacgt | 1500 |
| tacatatgat | ttttttgtca | agttacaca | tgattattga | caagaactta | cacatgataa | 1560 |
| tgccaaccat | tacttataaa | caaaatatcc | agaaaaaaaa | agaagaaga | agaaaagtag | 1620 |
| tcagtgaaaa | ggacaacatg | tacaataata | ttcaatggtt | aatcacgatg | gctaaaatga | 1680 |
| tccagctcac | gtgattctcg | tggatgatgt | aattacaaaa | cgactttaga | cccactaatc | 1740 |
| gtacactaac | atatgattat | tgacattaca | taataaaata | tctctacttc | ttgccagttt | 1800 |
| tcttacaaga | cattgataaa | catgttacat | gtcacagaaa | cattgtatca | agtaaaaagt | 1860 |

-continued

```
tttactttat caaaaaagaa agaaagtaaa aggttcgaga ggaattagtg aagataacct   1920
aatttaatac cttaatgtac ttccataaca agtcgatttt ttggatttaa caattatttt   1980
ggttttcaat ttttcacaat tctgtcttca tctttcaagc gatcctcttt gcgctaataa   2040
caagatggag aaaatcatga taaaatttag cgatgaggtt ttatccttt tcattttctg    2100 ttttatggtt aagttttgtg attaaagaat tagaagtttt ttacaggatt tagactatgg   2160
ttagagttta catttgattt agaattgtgt gactttcata taaaaataat gacatctacg   2220
aaattacgaa atacaaatat gggcttattc attattgggc catacaagcc catcgagttt   2280
agtattgatc ctctaatcaa aaaacgtaaa caataagat aacagaaaaa caaaacaaa     2340 aatttctgct ttgaagaaga agagtcgatc cataatcgcc actttcagat ttccagattc   2400
tggggaaaca tctctaaact cttcaacgat ggcgactgag aatctcaccg ataagaatgt   2460
tgttttcaga aagctgaaat caaaatccga gaacaaggtt agggttactc aattttcgat   2520
tttgaatttc gttcagatct ggagcttata cgacctaaat cttccgaatt gatttatgat   2580
tttgcttcgg ttttaggtt tgctttgatt gtagtgcgaa gaatccaaca tgggcttctg    2640
ttccttatgg gatcttccta tgcatcgatt gttctgctgt tcatcgaagt ctaggtgttc   2700
atatcagctt cgtcaggtaa aactttgaat cttgaggaac acaaatttga actctttagg   2760 cttaatttt agcttcatgg acttgtagca atgtttcacc ttctggctag ggtttaagct    2820
gtgattagga agatgttgac ttatttttc ctgttgacca ctctatttat agcatttcat    2880
gttgttgtag atctattata agatcatatt gtttttgtgc aggtcaacga acttagactc    2940
gtggagtcct gagcagctaa gaacaatgat gtttggaggg aacaatcgag ctcaggtgtt   3000
ttttaagcaa catggatgga atgatggtgg taagattgag gctaagtata cttcaagagc   3060
tgctgatatg tatagacaga ctcttgctaa agaagttgct aaagccatgg ctgaagaaac   3120
tgttttaccg tcgttatcct ctgttgctac ttctcagcca gtggaatcat ctgaaaatgg   3180
gtttacttct gaatctccga aagagagttc tttgaagcaa gaagcagctg ttgtctcttc   3240
accaaaagct tctcagaaag ttgttgctag tacgtttaag aaacctcttg tttcgcgaaa   3300
gtctgggaag actggtggtc ttggtgctcg taagcttact actaaggtaa cgttttcgt    3360 ttttataaag aattatagct tagcttctcg gttcttggtt ttgattagat tagtatttgt    3420
tgtatatgta gtcaaaggat aacctctatg agcagaagcc tgaagaacct gtacctgtga   3480
ttcctgctgc ttctccaacc aatgacacat cagcagctgg atcatcattt gcctctcgat   3540
ttgagtactt tgatgatgag caatctggtg ggcaaagtgg cacacgggtg cttagccatg   3600
ttgctccacc aaagtcatca aatttcttta atgaatttgg aatggacagt gctttccca    3660 agaagtcaag ctcaagctca tccaaagctc aggtaaagaa aagtttcatt tttaacagaa   3720
ctgaagaaag agatagaaat caattctcga ttcctctttg tttacctgtt ttcttttac    3780 ttaggttgaa gaaacagatg aagcaagaaa gaagttttca aacgccaaat cgatttcctc   3840
tgcccaattt ttcggaaatc agaacagaga tgccgatctt gactcaaaag ctacccttca   3900
gaagttctcg gtatgtcctt aaccgatcaa actctatact agttttcttt agtctcgttg   3960
ttcatacatg cctaatgcga ttacaaatct atcagggttc agcagctatt tcaagttctg   4020 atcttttgg ccacggacca gatgattcca acatcgatat cactgcaagc gatctcatca    4080
accgaatttc tttccaggta aagttctgaa gtagaatcaa attcttcagc ttttcttaac   4140
tctgcttata aggttttttt atttgacttt gtttattatt gggcacaggc gcagcaagat   4200
atgtcatcta ttgctaactt agctgaggaa acaaagaata agctgggaac atttgcctct   4260
```

-continued agtatattca gtgatcttca ggatagaatg ctgtaagaaa catacaaagg atcttgtctt    4320

<210> SEQ ID NO 18
<211> LENGTH: 402
<212> TYPE: PRT
<213> ORGANISM: Arabidopsis thaliana

<400> SEQUENCE: 18

```
Met Ala Thr Glu Asn Leu Thr Asp Lys Asn Val Val Phe Arg Lys Leu
 1               5                  10                  15

Lys Ser Lys Ser Glu Asn Lys Val Cys Phe Asp Cys Ser Ala Lys Asn
            20                  25                  30

Pro Thr Trp Ala Ser Val Pro Tyr Gly Ile Phe Leu Cys Ile Asp Cys
        35                  40                  45

Ser Ala Val His Arg Ser Leu Gly Val His Ile Ser Phe Val Arg Ser
    50                  55                  60

Thr Asn Leu Asp Ser Trp Ser Pro Glu Gln Leu Arg Thr Met Met Phe
65                  70                  75                  80

Gly Gly Asn Asn Arg Ala Gln Val Phe Phe Lys Gln His Gly Trp Asn
                85                  90                  95

Asp Gly Gly Lys Ile Glu Ala Lys Tyr Thr Ser Arg Ala Ala Asp Met
            100                 105                 110

Tyr Arg Gln Thr Leu Ala Lys Glu Val Ala Lys Ala Met Ala Glu Glu
        115                 120                 125

Thr Val Leu Pro Ser Leu Ser Ser Val Ala Thr Ser Gln Pro Val Glu
    130                 135                 140

Ser Ser Glu Asn Gly Phe Thr Ser Glu Ser Pro Lys Glu Ser Ser Leu
145                 150                 155                 160

Lys Gln Glu Ala Ala Val Val Ser Ser Pro Lys Ala Ser Gln Lys Val
                165                 170                 175

Val Ala Ser Thr Phe Lys Lys Pro Leu Val Ser Arg Lys Ser Gly Lys
            180                 185                 190

Thr Gly Gly Leu Gly Ala Arg Lys Leu Thr Thr Lys Ser Lys Asp Asn
        195                 200                 205

Leu Tyr Glu Gln Lys Pro Glu Glu Pro Val Pro Val Ile Pro Ala Ala
    210                 215                 220

Ser Pro Thr Asn Asp Thr Ser Ala Ala Gly Ser Ser Phe Ala Ser Arg
225                 230                 235                 240

Phe Glu Tyr Phe Asp Asp Glu Gln Ser Gly Gly Gln Ser Gly Thr Arg
                245                 250                 255

Val Leu Ser His Val Ala Pro Pro Lys Ser Ser Asn Phe Phe Asn Glu
            260                 265                 270

Phe Gly Met Asp Ser Ala Phe Pro Lys Lys Ser Ser Ser Ser Ser Ser
        275                 280                 285

Lys Ala Gln Val Glu Glu Thr Asp Glu Ala Arg Lys Lys Phe Ser Asn
    290                 295                 300

Ala Lys Ser Ile Ser Ser Ala Gln Phe Gly Asn Gln Asn Arg Asp
305                 310                 315                 320

Ala Asp Leu Asp Ser Lys Ala Thr Leu Gln Lys Phe Ser Gly Ser Ala
                325                 330                 335

Ala Ile Ser Ser Ser Asp Leu Phe Gly His Gly Pro Asp Asp Ser Asn
            340                 345                 350

Ile Asp Ile Thr Ala Ser Asp Leu Ile Asn Arg Ile Ser Phe Gln Ala
        355                 360                 365
```

```
Gln Gln Asp Met Ser Ser Ile Ala Asn Leu Ala Glu Glu Thr Lys Asn
        370                 375                 380

Lys Leu Gly Thr Phe Ala Ser Ser Ile Phe Ser Asp Leu Gln Asp Arg
385                 390                 395                 400

Met Leu

<210> SEQ ID NO 19
<211> LENGTH: 3180
<212> TYPE: DNA
<213> ORGANISM: Arabidopsis thaliana

<400> SEQUENCE: 19
```

| | | | | | |
|---|---|---|---|---|---|
| ttacatattc | gattcgttta | acttgatttg | gtgcttaccg | ttagagaaaa | cctccaccgg | 60 |
| tccaagcagt | gtctgatttc | ccattgtgac | ctacagattt | cttatcgctt | gcaggctgat | 120 |
| aatagaaatc | atcatcttta | gcatcattat | catcccaacc | agcccaaccg | ccgtcgtcat | 180 |
| catcattaga | agtcgacacc | tttggtgctg | cttcctttt | gctattgttc | tcttctcccc | 240 |
| agtcatccca | agaattcgag | ttacgataac | tgttgttgtg | accacttgat | gatgattgtg | 300 |
| atcctccaaa | agatgaattt | gctgttttgt | ttccaatccc | agagttctgg | tagtaaccgt | 360 |
| tgccctcagt | tttattctgt | tgattccaag | ttgatgcttc | ttctttagtg | aactcttcaa | 420 |
| ccttttgtga | ggcaattgcc | atcactcctt | tcatgatccc | ccatgtcctc | tgtcctatct | 480 |
| ctgttgtctt | actcgcaaca | acattaacag | tctcactgac | cgtctgatct | aagccacctt | 540 |
| ctttgacctg | cacaatgaac | aaaggtttct | tatctcactt | gtcttcaaaa | ttctataatt | 600 |
| tctaatgtta | gcagtatttg | aaaagaagga | cgagcatccg | gcattatgct | cagttcagcg | 660 |
| ttttagagga | tctccctaga | gattttgcag | gggcataaag | acaaaaaaaa | aaaaaagag | 720 |
| ctttaacact | gcaattaaag | taagaagatt | atgcagctag | aaaagactct | aattttgtgt | 780 |
| tacataacaa | tgtcaaaaat | gggataatct | aacaaacaga | gcaatgagca | tagcggcaat | 840 |
| tagacagaca | ccaagcgaat | agtcacgatc | tcaatataaa | cttaacaact | agactacaga | 900 |
| atgttaccaa | ggagtgagct | tactgatcac | gatgcaaacg | aatcaaccac | aacatcgaag | 960 |
| cagaaatgat | aaaagaagta | ccttggaagt | aaactccatg | gttccagtct | gaacaacatt | 1020 |
| tgcagctgat | gcagcaacaa | gagacaatct | tccaaaaccc | tataagcata | tacgcgtaaa | 1080 |
| acaaacacat | tcatttacag | gataaacaga | gaagtcactc | gcatgtcgca | tctaaccaaa | 1140 |
| tcactctcaa | aaagcttcca | aatttacctc | agacataaca | gagaaaacat | caccaccacc | 1200 |
| actctgttga | ttgcttctcg | gagctggacc | tggactagat | ccaaacccaa | catacttacc | 1260 |
| accttgtgaa | ggaggaagtc | cctcaggctt | agactcattc | tcagccatcc | ttttcgcaaa | 1320 |
| gaaactctcc | ttattcgccg | ccgacgcctc | cagctgagac | cgtgaatata | tatcctcaga | 1380 |
| cgatttcgac | ttcgcggag | caccacgacc | tcccgatgac | ctaaaatcac | ccgccgattg | 1440 |
| attcctcctc | atatccgtag | atctaaacga | atcatcgtta | tcccaattat | cccatccacc | 1500 |
| attaccagaa | tctctaccac | cgccttgaga | caacggaggc | ttcttattca | tcaatccacc | 1560 |
| accaaccgat | tccttaacaa | tcggcggatc | tctccattgt | cttccctcag | ctaaagcttg | 1620 |
| gatccgatct | cgatacacag | acgcggcgtt | ggaattgtac | ttggagatga | tatcagtctc | 1680 |
| tttcgagatc | ccgtactgag | cgagaaaatt | gttgagacgc | tcgttgcctc | cagcgtccat | 1740 |
| tttcttgatc | tggatctcgg | accatgaatc | catggtgacg | gatctgacga | atgagatgtg | 1800 |
| aacacctaaa | ccacggtgct | taccggagca | ttccaagcac | atgaagattc | catatgaaat | 1860 |

```
cgatgcccat tgtggattct tctgggagca atcgacacag accttgttct ccggctgaga    1920
ttggagcgtc cgtaatcgtc tcgccgctgc cattatattg ccggctctcc gatctgaccc    1980
ctgactagat ctgatccagg ttccagattc tgatgcgttt tttttggctc aatcgttttg    2040
cttaataaac gtggtaactt gaataatttt gtgcgtgttt ttgtcacgtg agagcttcac    2100
tcaatatttc caaggtctct gctaaaaacg tgtttgctca aaaagcatgg gctttggtcg    2160
cttcgatatc gggccgggtc tggaaggaac aaccaaaaaa actaaaacta ctctcgtttt    2220
cttcttccgc tcaaccctaa cttgtggaag tcagtttaaa gtccaggtga gcattaagac    2280
accaaatgtc cttgctgtga atatgaacgg agaacaact gatggggtc tgaagaagga     2340 attaactgaa gtgatgaagc agggacagat tctgagtgtc aaggtttgtt tcttgttcat    2400
tgattgttat gcattgcact gttttaaacc ataagtcttt gatgatattc ttttattttt    2460
cactaataag cagataaaaa aagattggta ctggaattgt ccaacaggtg aacctaatgt    2520
agagtcttat taacataact aaaggccaaa agcggcaga acacttcatg aagcatggac     2580
ttgaggaatt gttcagcttc acattattcc ggtccacgtg tctggtacgg tagagtagcc    2640
aaatcccagc aaagtcacag ttaccagaat ttactctttc attctgaatt gttgtatctt    2700
tttctttctt ttcttttgaa ctcaaatcct tgttatctcc ctgttgacta tcttttttaga   2760 acaataatgc tcattagaag cttttcaact ctagttatat attattttcc aatgcacaaa    2820
ttataacatt tgattcattc attcaaacaa ttagaacatt tcatacaaat ccctaacaac    2880
agctgagaaa tctcaactcc cccaattaac aaatctcaat aggccatagc cgtcacagtc    2940
tttctgtcac agccatgtga ttttgtgaac atcacatata gaccgttgga tctgttgtca    3000
tccgtatcat cacatcggaa ccgtttaatt tttatgattg tgaaacgacg acgtaaagtt    3060
gttaaccggg aaagacgaag aaaaacgcgc gggaaaattg agagactgca tcttaatcat    3120
cgtagggatt ctctattttt tggaatctga ttcatatgtt tggggtttaa tagtctcagc    3180

<210> SEQ ID NO 20
<211> LENGTH: 5640
<212> TYPE: DNA
<213> ORGANISM: Arabidopsis thaliana

<400> SEQUENCE: 20
cagtttcact caccttgtga tcatacccac cttccttcac ctgcaataaa atggtttctt     60
atctgatttt gactccactt ttccaaaact ctattgccag cagtattatg gtaaacaaga    120
attctacaga gagcatctaa gaattgtgct ttctacagag ttaaagattc tcactagacg    180
tgtcgttgag gcatcaagca acgcagtaac tagatatttc acaaactcta tgcaaatcaa    240
gcagagagta cagatagtta gttaccttgg atgtgaactc cttggttcct gtttgaacaa    300
cactagcagc tgactgagct gcagatgcag caaccagaga cagtcttcca aaacccttag    360 caattttta acacgaatca acacacaaaa cgtaattcac cgaattcaaa aaggaattgc    420
aaaacattca ttcaattcac ctgagaaaca acggagaaaa catcatcctg ttgattattt    480
ctcggtggtg gagccgagct tgatccgaat cctacatact tgccaccttg cgaaggagga    540
agaccttcag gcttagactc attctccgcc attctcctcg cgaagaaact ctctttccca    600
gcggcagaag cctcaagctg cgatcgcgtg tagatatcct ccgacgactt tgacttcaca    660
tgtgcacctt ctctatttcc cgatgccctg aaatcattcg ctgactgatt ccttctcata    720
tcagatttgt aagaatcatc gttatcccaa ctatcccatc ctccattgtt attgttattg    780
ttgtttccgt aaccgccctg agccaacgga ggcttcttat tcgcttcctt aacaactggc    840
```

-continued

| | |
|---|---|
| ggatcattcc atggtctacc ttcagctaaa gcttggatcc ggtcacgata cacagaagca | 900 |
| gcgttcgaat tgtacttgga gataatatct gtctccttag cgattccgta ttgcgcgaag | 960 |
| aatttgttga gccgttcgtt accaccagct tccattttct taatctggat cgcagaccat | 1020 |
| gaatccatgg ttacggatct gacgaaggat atgtgaacgc taagcctcg gtgtttcccg | 1080 |
| gagcattcca acacatgaa gattccgtac gaaaccgacg cccattgagg attcttctga | 1140 |
| gcgcaatcga cacatacctt gttttcaggc tgagattgga gagttcgtaa ttgtctcgtc | 1200 |
| gccgccatgt ttcccggagc tccgaacgat gatcaatcca acctgaatca gatctaatcc | 1260 |
| aaatctcgca gacttgtgct gctcagattg atgcgttttt ttttcttttc cgttttttct | 1320 |
| cttcttccta ataaatgttc ggggtttttt tggtacgtg tctctggcac gtgagaggtt | 1380 |
| tccggtagtt tctcaaatgg cccaaatgat aattgtattt actatttagt ccaaatatga | 1440 |
| aattatatgt agacgatgcc caagatgccc aatcatggtt atttatatgt agacgatctt | 1500 |
| acaattctta ctcaagagct atctatatat tgtagataaa ctacatcttc aactaaccac | 1560 |
| tttaaccatg cattaagccg aagtttaagt actagatcaa tttatttatt gttatcatac | 1620 |
| atttgtgtct ccgttaatac ttagagaaga ctcactaaca attttggaaa ccgtaatatc | 1680 |
| ctctacatga gctttgttgt gttgttgaac cacaaggatt gatggaatga tgtggttgat | 1740 |
| cgaagaggcg agcacgtctc cgataggacc taactcagga tgttcagctt gacgctcagc | 1800 |
| taatgccgcc acctcggccg acggtatcct ccctcttcca accactatta gatcaaagtc | 1860 |
| tttactctgt cctattgaca gtatttcttc aatgatgttg tttggttcct tttctttgta | 1920 |
| ctccaccatt tctttccatt tgctcttgaa gtcttccaat gccccttcgt ctaattccta | 1980 |
| taattatttt tccaagaaag aaagctatag ttatatttgt cataactggt atataaacat | 2040 |
| agggatcaa aagagattta ccttttcttt ttctggatcc acgttggttg ttaaaaaggc | 2100 |
| atagttcttc tccttgcctt tagacggtgc cggtcgtaaa gtgacggcgg tactcctcaa | 2160 |
| cgtttctctt accaaaaacc taataacggt aactttaacg gccggatgct cagccattct | 2220 |
| cccgccgagc tctatagact cacggtcatc aggcccacca agaaaatca cacaaaccct | 2280 |
| ttcaaccaca ttcgacccat ctaagctcaa agtttgggcc tcaatggacc caagtccacg | 2340 |
| gtctacaaga accgccaccg aacacggcgc attcttcaaa acccttggt taaccaatcg | 2400 |
| ccaaccatga ccaacgtttt ccggtacgtt tccatctcct cctccgtctt ggtggtggtg | 2460 |
| gctatgacca tgatcagcgt tccatcgttt gtggaaaggt aaaatgatca ttgtgaccct | 2520 |
| cttggtatct gccatgtggc aaatgtcttc gtgcattgtg ggtaatggag agactgcggt | 2580 |
| gatgggccgg actgcgaccc ggcctagttg acgataggct tcgaagcctc ctatgacgtt | 2640 |
| gctgtgacgc tcaccatgac ggtaacggtg aacgaaagga agtccgtttt tacgggctct | 2700 |
| ttgcaccatt atgattgacg aagaccgttc cgttagttcc atcagatgca tcacaaacag | 2760 |
| ctttagccgt agtatctgcc aaaacaaata cgactttta aattattaac caagattata | 2820 |
| aattattacc cagctgattt ttaattttaa ctatacaaaa tgtgtgtaat tatacgtagg | 2880 |
| atacattttc attgagcatt tcaatgatat cttaattttc tgatataact cttatcatag | 2940 |
| atttacaaat ttaaatatag attattgtaa cgtaaaaata taaagaaag gtaatttacc | 3000 |
| ttggtggttc ggatggactc gacgagagag atgagggagg agacattggc tgggccgtgg | 3060 |
| aggcaggcta ggatgcgaag ctcttccttg gtggagtctt ggctcgccga caagtctttt | 3120 |
| agtttgcggt gggtgccacg tgccggcttg taaatggcca ttacagtagg cgtcgttatg | 3180 |

```
aacgttgtga agagtgccat tagcactagt attgcaaacg tctcgtcgtt tagtacctgg   3240
ttaaagtcaa ccccgcgtac aaacagttta attaaaaata accacactta ctacattaat   3300
gggtaatcat tatttcactt tattgttgca ttatgaagaa gatcataaat ctgcaagtgg   3360
atcagtaagt gacgattacg taaacattgg cccattcgaa aaggtatatt cgtataaagt   3420
tttcatgcag aaaaaaaaat aaaaataaag ttttcatgca tgcatatata tgactagtcc   3480
ttaattgatc agtttttctt tattacccca aaacaataag aaacgccttt ataataaaag   3540
tgtagtatat aactataatc tttgttggga agacacgttt aaacaaaaaa ttttatatac   3600
tacatatttc cagaagcatt atagtataat cttgcacata tatttaagat aaaaatgttt   3660
atttcggagg tgacaaaaga atcacggact aatgttttga agctaccatt gctaactgca   3720
tcatcttcga tgcacatagt aaacttagct atcaaattgc aaccgtgtcc atcagtctat   3780
gattaatgaa ctgcagattt gtattatggt gactaatatt actatacaac ggttgagagc   3840
aaacctagct atcaaattgc aaccgtgtct attatagtga tagtaaacct agcagcccgg   3900
ctcaatattt tattgggccc tgtgctacaa acaaaaatag cccttaaatc taaacaaaat   3960
aactttatgt gacatgtgtt tactgtattt ttattttaaa cttattatct tttattttgg   4020
tggttgtttt ttttgtagtt ttccccttaa aaaaaaaaa actgcaaact agaagactta   4080
aaattaagaa aaaaaaatga ggaccctgtg tactagcacc tctggcactc ccctagagcc   4140
gggcctgcct agctatcaat ttgaatttat acaacggttg gttaatgttc aaataaaaca   4200
taagcaattt tactattccg gatccccgac cagcctacca atattgagcg gaccggacgc   4260
atatacacat ggatccaact agaacctaaa ttttaaaata tatctaaaca ccctaaaata   4320
aaggtataga tgcgattaaa tcaatataat aatcgtattt tgtttttatat gctttatcca   4380 ctaaacatga tcaaataact ttagtgttac taggttttt atatttataa tattcatcag   4440
ataactaaaa gcgtaaacaa gaaccttaaa aaatcagaaa aaaggaagac aaaactaacc   4500
tttttctcct tgcctatgtt gagtacaatg agctccacta aacctttagt attcatcaag   4560
aaaccaagtg tcaacgcctc tctcgccgga actttaacca tcaccgccac aacaaaagtt   4620
ccgactatct tcccggcaca agccgtaaca acaacaagac ccaacatccc ccacgactca   4680
gctcctctaa tcttagccac gtcagtcttc aaaccactcg tagcgaaata aagcggtaag   4740
agtaaaccgg aaacaaaatc ctcaattcgt tcaatcaatc gctgaccaaa ctctccatct   4800
ttcggtatag tcaaaccgaa aacaaacgct ccaaaaatcg aatgaatccc aattaaatcc   4860
gtcgcgaaac cggaaaccat aacaccggct aacgtcaaac acacgtaaga ctcgcgtacg   4920
acgtcgtttt caggagatcc acgtttcgcg acccatttca ttccgggtcg gatcacaacc   4980
aacataaaaa ccacaaaccc agcgcccgat aacaaaaccc acaacgacac taacggactc   5040 ttttctctc cacctccctc accgccatta cccgctaacg caaccgctaa agcgagtaaa   5100
atccacgcgg ctacatcgtt aaaagcggct gcagccatcg cggtttctcc tatctgagtc   5160
gttaaaagct tgagctctgc taaaatacgc gcaagtaccg gaaaagctgt gatcgagagt   5220
gcgactccca tgaaaacgag aaactcggcg taacctggtt tatccgcggc ggtgtagaga   5280
gtgttacgga tcacaaacgc gactccgacg ccggcgataa acggtagtgt aattccagcg   5340
actgcgattc cgaaagcgcg tttgccgctt cgtcggatcg atgataaatc gagttctaga   5400
ccgacgagga agaggaagaa gagaagtcct atgctcgcga cggattcgag tatcggcata   5460
ctccatttcg gaaatatacg gtccatgtac gccatgtttc tacctaaagc cgatggtcct   5520
aacaaaatcc ctccctgaag aagaagacga tggcagaatt gtaaattaag aagattatta   5580
```

-continued

| | |
|---|---|
| tggtaaaatt gtaaatagtt agtgtgtgtg gggttagagt gtaattttta acgtacgaca | 5640 |

<210> SEQ ID NO 21
<211> LENGTH: 4320
<212> TYPE: DNA
<213> ORGANISM: Arabidopsis thaliana

<400> SEQUENCE: 21

| | |
|---|---|
| aagacaagat cctttgtatg tttcttacag cattctatcc tgaagatcac tgaatatact | 60 |
| agaggcaaat gttcccagct tattctttgt ttcctcagct aagttagcaa tagatgacat | 120 |
| atcttgctgc gcctgtgccc aataataaac aaagtcaaat aaaaaaacct tataagcaga | 180 |
| gttaagaaaa gctgaagaat ttgattctac ttcagaactt tacctggaaa gaaattcggt | 240 |
| tgatgagatc gcttgcagtg atatcgatgt tggaatcatc tggtccgtgg ccaaaaagat | 300 |
| cagaacttga aatagctgct gaaccctgat agatttgtaa tcgcattagg catgtatgaa | 360 |
| caacgagact aaagaaaact agtatagagt ttgatcggtt aaggacatac cgagaacttc | 420 |
| tgaaggtag cttttgagtc aagatcggca tctctgttct gatttccgaa aaattgggca | 480 |
| gaggaaatcg atttggcgtt tgaaaacttc tttcttgctt catctgtttc ttcaacctaa | 540 |
| gtaaaagaa aacaggtaaa caagaggaa tcgagaattg atttctatct ctttcttcag | 600 |
| ttctgttaaa aatgaaactt ttctttacct gagctttgga tgagcttgag cttgacttct | 660 |
| tggggaaagc actgtccatt ccaaattcat taaagaaatt tgatgacttt ggtggagcaa | 720 |
| catggctaag cacccgtgtg ccactttgcc caccagattg ctcatcatca aagtactcaa | 780 |
| atcgagaggc aaatgatgat ccagctgctg atgtgtcatt ggttggagaa gcagcaggaa | 840 |
| tcacaggtac aggttcttca ggcttctgct catagaggtt atcctttgac tacatataca | 900 |
| acaaatacta atctaatcaa aaccaagaac cgagaagcta agctataatt ctttataaaa | 960 |
| acgaaaaacg ttaccttagt agtaagctta cgagcaccaa gaccaccagt cttcccagac | 1020 |
| tttcgcgaaa caagaggttt cttaaacgta ctagcaacaa cttctgaga agcttttggt | 1080 |
| gaagagacaa cagctgcttc ttgcttcaaa gaactctctt tcggagattc agaagtaaac | 1140 |
| ccatttcag atgattccac tggctgagaa gtagcaacag aggataacga cggtaaaaca | 1200 |
| gtttcttcag ccatggcttt agcaacttct ttagcaagag tctgtctata catatcagca | 1260 |
| gctcttgaag tatacttagc ctcaatctta ccaccatcat tccatccatg ttgcttaaaa | 1320 |
| aacacctgag ctcgattgtt ccctccaaac atcattgttc ttagctgctc aggactccac | 1380 |
| gagtctaagt tcgttgacct gcacaaaaac aatatgatct tataatagat ctacaacaac | 1440 |
| atgaaatgct ataaatagag tggtcaacag gaaaaaataa gtcaacatct tcctaatcac | 1500 |
| agcttaaacc ctagccagaa ggtgaaacat tgctacaagt ccatgaagct aaaaattaag | 1560 |
| cctaaagagt tcaaatttgt gttcctcaag attcaaagtt ttacctgacg aagctgatat | 1620 |
| gaacacctag acttcgatga acagcagaac aatcgatgca taggaagatc ccataaggaa | 1680 |
| cagaagccca tgttggattc ttcgcactac aatcaaagca aacctaaaaa ccgaagcaaa | 1740 |
| atcataaatc aattcggaag atttaggtcg tataagctcc agatctgaac gaaattcaaa | 1800 |
| atcgaaaatt gagtaaccct aaccttgttc tcggattttg atttcagctt tctgaaaaca | 1860 |
| acattcttat cggtgagatt ctcagtcgcc atcgttgaag agtttagaga tgtttcccca | 1920 |
| gaatctggaa atctgaaagt ggcgattatg gatcgactct tcttcttcaa agcagaaatt | 1980 |
| tttgtttttg tttttctgtt atcttatttg tttacgtttt ttgattagag gatcaatact | 2040 |

```
aaactcgatg ggcttgtatg gcccaataat gaataagccc atatttgtat ttcgtaattt    2100
cgtagatgtc attattttta tatgaaagtc acacaattct aaatcaaatg taaactctaa    2160
ccatagtcta aatcctgtaa aaaacttcta attctttaat cacaaaactt aaccataaaa    2220
cagaaaatga aaaggataa aacctcatcg ctaaatttta tcatgatttt ctccatcttg     2280
ttattagcgc aaagaggatc gcttgaaaga tgaagacaga attgtgaaaa attgaaaacc    2340
aaaataattg ttaaatccaa aaaatcgact tgttatggaa gtacattaag gtattaaatt    2400
aggttatctt cactaattcc tctcgaacct tttactttct ttcttttttg ataaagtaaa    2460 acttttact tgatacaatg tttctgtgac atgtaacatg tttatcaatg tcttgtaaga    2520
aaactggcaa gaagtagaga tattttatta tgtaatgtca ataatcatat gttagtgtac    2580
gattagtggg tctaaagtcg ttttgtaatt acatcatcca cgagaatcac gtgagctgga    2640 tcatttagc catcgtgatt aaccattgaa tattattgta catgttgtcc ttttcactga     2700
ctacttttct tcttctttct tttttttttct ggatattttg tttataagta atggttggca    2760
ttatcatgtg tagttctttg tcaataatca tgtgtaactt tgacaaaaaa atcatatgta    2820
acgttttaaa aaattatata ctttggttgg tcattatagt tttagccaaa cgataaaaaa    2880
tttgatgaaa aaaatgtggt taaagaaaac ttacagtata ccgtgacaaa aatatgaaga    2940
ttgttaataa atagatatgt caattatggt gacagaaaca tggaaagcag acagacgatg    3000
cctagacaga ggacccaaac aattaaagtg ggctacacaa cataattcca atatttaaaa    3060
aaagaaaaaa acaatttaaa atgtctaaga aaaataaat tcgaatatga attttataga    3120
gaaaatacaa attttatacg ttaatttctt cctctttcaa aaattgaacg gaagttgcta    3180
tgttgttgga tacattatta tttgaatata tattacaaat aattttttagg actagcaaat    3240 catttttttga gttttctttt tatggttttc gtagtcaact ccacaaccga tagttttaca   3300
tcgatgcttg tacaatttta cagtttgaca gatggtactg tactacgaca tacgttcta    3360 tgcaccacac taaaatctct agatagaaat cgtttccatt aatcttcaat aatttgtaat    3420
ctatgaaaat caaacttcat atatggtgtg atgaagtatt aatggatatt tagttaacca    3480
ttacaccaaa aaaaaattta caccggataa ttatttgaaa acgtaaattt catattaacg    3540
gttcaaactg atttttaata aaatgaacat aatgaaatga tatttaaaaa aaaaagatga    3600
ttggagaaag aaaacacttt tagttttttc atatatattt attttcctat aactaacata    3660
aaatcagttg aaatattatt ttaaattcct aacttaattg atataaattg agtagaatct    3720 attttttttcc ttttaaaaat gcaattcttt tttgcagttt aaaatattaa tttatatgaa   3780
aaataaaatt tatattttag atttctaact tatgaaattt tgaattatag cattggtcca    3840
tattcgaaac tctaagtcac tatatcacca taaatggatt atttattagt tttttctcca    3900
taaaacaata agtggctatg tgataataaa cggatctaag ttatgtttca gacaaaacag    3960
tgtccaaacg agaattatca ctccatgaat aatttattta cgttttcgta acagttaacc    4020
aaattattat cgtttggttt ttgtcatata atatgtcgca actctcaaca aaaacttaag    4080
aaaataagaa aaaattattt acaattgttt tagaaaaaca ataaaaataa aatatagtat    4140
tgtagagaga atcatcttct ccaaacaatc actaaacgcc atttgcttag ctttttccct    4200
cttttgattt ttcctcccta cacgtcacct ctctcttctt ctcaccggaa aaagtcttc    4260 acctttcacc ggaaaatatc acctttttcaa ccggcgtatg ttcacatgaa cggcacaaca    4320
```

GENETIC CONTROL OF ORGAN ABSCISSION

RELATED APPLICATIONS

This Application is a continuation of International Application PCTUS02/01938, filed Jan. 22, 2002, which claims the benefit of priority under 35 U.S.C. 119(e) to U.S. Provisional Application Ser. No. 60/264,974, filed Jan. 29, 2001, the disclosures of which are incorporated by reference herein in their entireties.

GOVERNMENT INTEREST IN THE INVENTION

Certain aspects of the invention disclosed herein were made with United States Government support under National Science Foundation Grant No. MCB-004-9003 and Department of Energy Grant No. DE-FG03-00ER-15113. The United States Government may have certain rights in the invention.

FIELD OF THE INVENTION

The invention relates to genetic control of organ abscission in plants. In particular, the invention relates to regulation of floral abscission in plants by the NEVERSHED gene, and homologs, variants, and fragments thereof. The invention further relates to the use of NEVERSHED, homologs, variants, and fragments thereof, to manipulate floral abscission in a variety of plant species.

BACKGROUND OF THE INVENTION

Specialized cell types allow plants to shed entire organ systems, such as leaves, flowers, and fruits. The ability to shed organs that have fulfilled their purpose enables plants to make efficient use of nutrients and energy sources. Abscission can also act as a plant defense mechanism: plants can protect themselves from disease by shedding infected organs. Organ shedding sometimes serves a propagative function, as in the seed dispersal promoted by fruit abscission.

Abscission zones are thought to differentiate as organs form, and can consist of a few to several cell layers of small, densely cytoplasmic cells. Prior to abscission, these cells have been shown to enlarge, and to secrete cell wall hydrolyzing enzymes such as cellulases and polygalacturonases. Secretion of polygalacturonase causes breakdown of the pectin-rich middle lamella between neighboring cells, thus allowing for cell separation to occur between abscission zone cells. After the organ has been shed, abscission zone cells left behind enlarge and form protective scar tissue (Bleecker and Patterson, 1997, *Plant Cell* 9: 1169–1179, which is incorporated by reference herein in its entirety).

Studies using abscission zone explants have demonstrated that ethylene promotes abscission (reviewed in Sexton and Roberts, 1982, *Ann Rev Plant Physiol* 33: 133–162; Osborne, 1989, *Crit Rev Plant Sci* 8:103–129, both of which are incorporated by reference herein in their entireties), and ethylene has been linked to abscission zone cell enlargement and zone-specific expression of hydrolytic enzymes (Jensen and Valdovinos, 1968, *Planta* 83: 303–313; Valdovinos and Jensen, 1968, *Planta* 83: 295–302; Wright and Osborne, 1974, *Planta* 120: 163; Koehler et al., 1996, *Plant Mol Biol* 31: 595–606; van Doom and Stead, 1997, *J Exp Bot* 48: 821–837, all of which are incorporated by reference herein in their entireties). A genetically defined role for ethylene response in the temporal regulation of abscission has been demonstrated by the discovery of ethylene-insensitive mutants such as etr1 and ein2 (Bleecker et al., 1988, *Science* 241: 1086–1089; Guzman and Ecker, 1990, *Plant Cell* 2: 513–523, both of which are incorporated by reference herein in their entireties). Studies of these *Arabidopsis* mutants have shown that ethylene insensitivity causes a delay in floral abscission, indicating that ethylene response mediates the timing of programmed cell separation (Bleecker and Patterson, 1997, *Plant Cell* 9: 1169–1179, which is incorporated by reference herein in its entirety). However, abscission does eventually occur in ethylene-insensitive mutants, albeit delayed, indicating that additional pathways must also regulate this process.

Although numerous studies have addressed hormonal regulation of the abscission process and physiological aspects of abscission zone cell separation, very few studies have focused on regulation of abscission zone development, with the result that the genes whose function is necessary for abscission to occur have not been identified in any plant system. Studies of genetic control of abscission zone development is being carried out using two tomato mutants known as jointless and jointless2 in which formation of pedicel abscission zones in tomato flowers is prevented; molecular characterization of the jointless locus is currently in progress (Butler, 1936, *J Hered* 27: 25–26; Wing et al., 1994, *Mol Gen Genet* 242: 681–688; Zhang et al., 1994, *Mol Gen Genet* 244: 613–621; Szymkowiak and Irish, 1999, *Plant Cell* 11: 159–176, all of which are incorporated by reference herein in their entireties).

Screens for abscission (abs) mutants in the model plant *Arabidopsis* have been carried out and several abs mutants have been isolated in which floral abscission is delayed. The lack of mutants for which organ abscission is specifically and completely blocked has limited the progress of studies of abscission zone development in *Arabidopsis*.

The small GTP-binding protein ARF plays an established role in the control of vesicular traffic and in the regulation of phospholipase D (PLD) activity. GTPase activating proteins (GAPs) are associated with all families of small GTP binding proteins, acting as signal terminators and possibly also in some cases as effectors downstream of the GTP binding protein. The fact that ARF has undetectable intrinsic GTPase activity suggests that the ARF GAP is an essential terminator of ARF-regulated processes.

ARF has important roles in the control of vesicular traffic and in the regulation of phospholipase D activity. Replacement of bound GDP with GTP produces active ARF-GTP, which can associate with membranes. Both forms are important in vesicular transport, which requires that the ARF molecule cycle between active and inactive states. Like the many other GTP-binding proteins or GTPases that are molecular switches for the selection, amplification, timing, and delivery of signals from diverse sources, ARF finctions via differences in conformation that depend on whether GTP or GDP is bound. Vectorial signaling results from the necessary sequence of GTP binding, hydrolysis of bound GTP, and release of the GDP product (Moss & Vaughn, 1998 *Jnl Biol Chem* 273: 21431–21434, which is incorporated by reference herein in its entirety).

ARF proteins in their GTP-bound form are required for coatomer binding to Golgi stacks and for the binding of clathrin adaptor particles to the trans-Golgi network. GTP hydrolysis is required for the dissociation of these proteins from Golgi-derived membranes and vesicles, a process in which an ARF GAP is most likely involved, indicating that ARF GAPs are involved in vesicle coat disassembly as an uncoating factor.

Vesicular transport has been extensively studied in the Golgi and ER-to-Golgi pathways (Cosson & Letourneur, 1997 Curr. Opin. Cell Biol. 9: 484–487, which is incorporated by reference herein in its entirety). The mechanisms, including the molecules and their functions, are likely very similar in other pathways. Formation of a transport vesicle begins when activated ARF with GTP bound to it associates with the cytoplasmic surface of a donor membrane. Activated ARF interacts with a coat protein, one of seven in the coatomer complex. Recruitment of multiple ARF molecules followed by coatomers causes membrane deformation and budding. Bilayer fusion at the base of a bud induced by fatty acyl-CoA results in vesicle release. Roles for PLD in both vesicle formation and fusion have been suggested. Removal of the coat, which is necessary for vesicle fusion at the target membrane, requires inactivation of ARF by hydrolysis of bound GTP to GDP.

Mammalian ARFs are divided into three classes based on size, amino acid sequence, gene structure, and phylogenetic analysis; ARF1, ARF2, and ARF3 are in class I, ARF4 and ARF5 are in class II, and ARF6 is in class III. Non-mammalian class I, II, and III ARFs have also been found. A role for class I ARFs 1 and 3 in ER to Golgi and intra-Golgi transport is well established (Cosson & Letourneur, 1997, Curr. Opin. Cell Biol. 9: 484–487, which is incorporated by reference herein in its entirety). ARF6 has been implicated in a pathway involving plasma membrane and a tubulovesicular compartment that is distinct from previously characterized endosomes (Radhakrishna & Donaldson, 1997, J Cell Biol 139: 49–61; Moss & Vaughn, 1998, Jnl Biol Chem 273: 21431–21434, both of which are incorporated by reference herein in their entireties).

An ARFI GAP (purified and cloned from liver) was recruited to membranes by overexpression of ERD2, a membrane receptor that recognizes the C-terminal sequence (Lys-Asp-Glu-Leu) found on certain soluble proteins (KDEL proteins) of the endoplasmic reticulum and serves to retrieve them if they are transported to the Golgi (Aoe et al., 1997, EMBO J. 16: 7305–7316, which is incorporated by reference herein in its entirety). Oligomerized ERD2 associated with the GAP, which then inactivated membrane-bound ARF and produced in the transfected cells a phenotype like that resulting from inhibition of ARF guanine-nucleotide exchange proteins (GEPs). It was later shown that overexpression of lysozyme with a KDEL terminus, which was intended to increase engagement of the KDEL receptor in retrograde retrieval transport, increased its interaction with ARF GAP and ARF inactivation, demonstrating a way in which vesicle content/cargo can influence a transport pathway (Cosson & Letourneur, 1997, Curr. Opin. Cell Biol. 9: 484–487, which is incorporated by reference herein in its entirety).

ARF GAP activity appears to be modulated by phospholipids. GAP activity is strongly stimulated by $PIP_2$ and was inhibited by phosphatidylcholine, as indicated by Makler et al (1995, Jnl Biol Chem 270: 5232–5237, which is incorporated by reference herein in its entirety) using both crude and purified GAP preparations. The effects of phospholipids on the ARF GAP may be related to a recently discovered role of ARF in the regulation of phospholipid metabolism (Kahn et al., 1993, Cell 75: 1045–1048, which is incorporated by reference herein in its entirety), where ARF was identified as the cytosolic GTP binding protein that activates phospholipase D. Activated phospholipase D cleaves phosphatidyl-choline to produce phosphatidic acid and choline. A feedback loop mechanism has been proposed where following the activation of phospholipase D by GTP-bound ARF, an increase in local phosphatidic acid concentration (and possibly also a decrease in phosphatidylcholine concentration) brings about an increase in the activity of the ARF GAP, resulting in the hydrolysis of ARF-bound GTP and the cessation of phospholipase D activity.

In other experiments using recombinant GAP, dioleylg-lycerol dramatically increased the activity of the recombinant GAP (amino acids 1–257). Because monosaturated diacylglycerols are produced chiefly from PC via the sequential action of PLD and phosphatidate phosphohydrolase (whereas polyunsaturated diacylglycerols are derived from $PIP_2$ via phosphatidylinositol phospholipase C action), it was suggested that PLD activity could be a major regulator of ARF GAP (Antonny et al., 1997, J Biol Chem 272: 30848–30851, which is incorporated by reference herein in its entirety). GAP activity was varied 100-fold by altering relative amounts of PC and diacylglycerol (Antonny et al., 1997, supra, which is incorporated by reference herein in its entirety), and similar effects were observed on the activity of and lipid binding by Gcs1, an analogous ARF GAP from yeast.

By comparing systematically the effects of phospholipid polar head groups and hydrocarbon chains on binding to the two GAPs, it was concluded that membrane association depended chiefly on hydrophobic interaction of the protein with hydrocarbon moieties of the lipid, which is favored by small head groups, and the conformation of monounsaturated acyl chains (Antonnye et al., 1997, supra, which is incorporated by reference herein in its entirety). In this view, the activation of ARF GAP results from increasing its concentration at the membrane where ARF-GTP resides. ARF activation of PLD leading to decreased PC and increased diacylglycerol levels would promote translocation of ARF GAP to a vesicle membrane where it could inactivate ARF-GTP and thereby terminate PLD action. The ARF GAPs that are activated by $PIP_2$ or other phosphoinositides are presumably subject to different kinds of regulation.

The process of abscission in plants affects many important physiological events in the various stages of plant growth. Thus, the ability to control abscission would be beneficial for many aspects of plant biology and crop science. What is needed in the art is a method of genetically modulating the process of organ abscission in plants.

SUMMARY OF THE INVENTION

In one aspect of the invention, a plant exhibiting decreased organ abscission is provided. The plant has a nucleotide sequence with a modified ARF GAP domain. The decreased organ abscission may be include floral abscission. In some embodiments, the organ abscission may be abolished. In some embodiments, the plant may be *Arabidopsis thaliana*. In some embodiments of the invention, the nucleotide sequence can be SEQ ID NO: 3 or SEQ ID NO: 5.

Aspects of the invention also include the sequence of SEQ ID NO: 3 and SEQ ID NO:5, or isolated nucleotide sequences that hybridize to the complement of the sequence of SEQ ID NO: 3 or SEQ ID NO:5 under moderate stringency, where expression of the nucleotide sequence in a plant results in reduced or abolished abscission.

A further aspect of the invention includes a method of preventing organ loss in a plant, by mutating the ARF GAP domain of a gene in a plant and determining if the mutation results in the prevention of organ loss in the plant. In some embodiments, the organ loss can be floral organ loss. In some embodiments, the mutation is performed by exposure to ethyl methanesulphonate (EMS). In some embodiments, the gene can be the nucleotide sequence of SEQ ID NO: 1.

Additional embodiments of the invention provide an isolated polypeptide comprising the amino acid sequence of SEQ ID NO: 4 or SEQ ID NO: 6.

BRIEF DESCRIPTION OF THE DRAWINGS

FIG. 2. Alignment of putative ARF GAP domain from the NEVERSHED amino acid sequence (SEQ ID NO:22) with ARF GAP domains from rat ARFGAP1, (SEQ ID NO:23) yeast GCS1, (SEQ ID NO:24), fly CG8243 (SEQ ID NO:25) and worm W09D10.1 (SEQ ID NO:22). Identical amino acids for all sequences are indicated below the alignment. C to Y substitution caused by nev-1 mutation is indicated.

DETAILED DESCRIPTION OF THE PREFERRED EMBODIMENT

Figure 1:
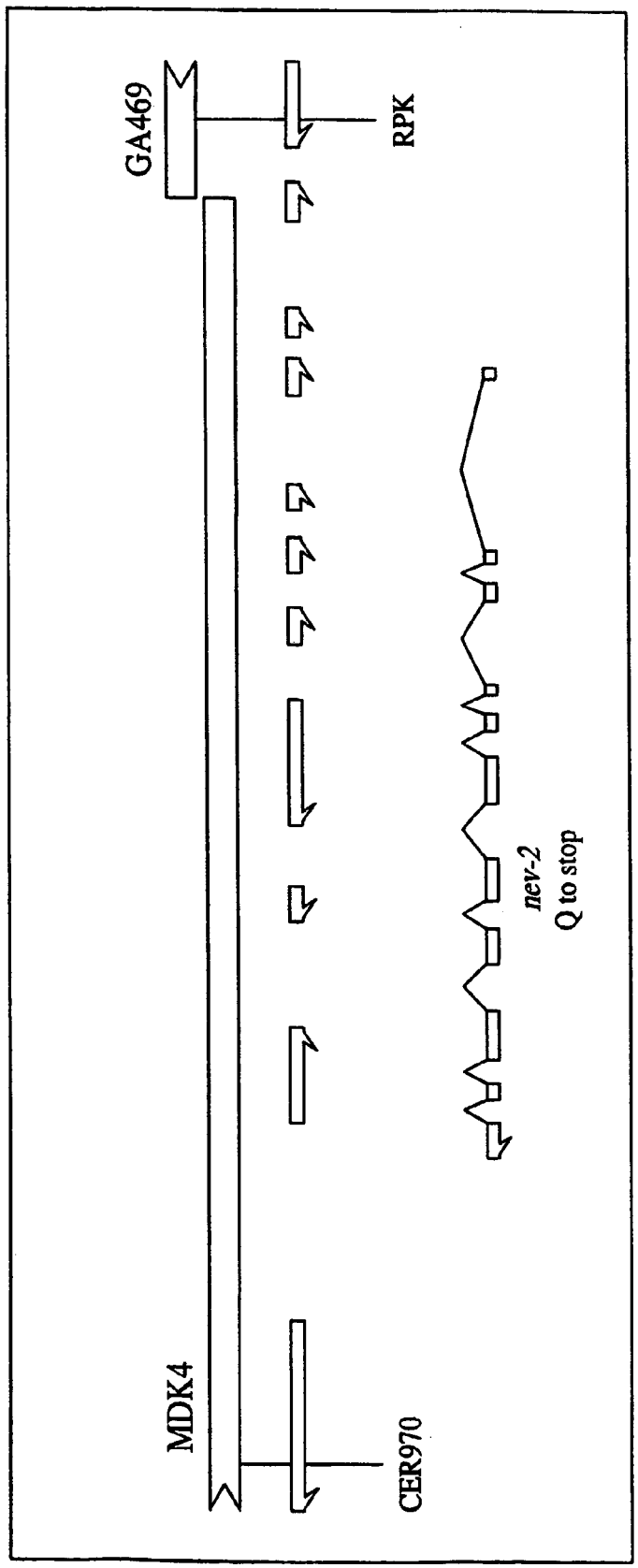
FIG. 1. Location of NEVERSHED genomic sequence on chromosome 5. The location of markers CER970 in the region corresponding to bacterial artificial chromosome (BAC) MDK4 and RPK in the region corresponding to BAC GA469 are indicated. The location of exons within the NEVERSHED genomic sequence and the nev-2 mutation are indicated.

Embodiments of the invention relate to the discovery that genetic modification of particular genes in a plant can result in prevention of organ abscission. In one embodiment, modification of the ARF GAP domain of a gene resulted in prevention of flower abscission. Accordingly, one embodiment of the invention is a method for preventing organ abscission in a plant by modifying the ARF GAP domain of gene. In another embodiment, the invention includes methods of preventing floral abscission in a plant by modifying the ARF GAP domain of a gene.

Particularly relevant genes include the family of NEVERSHED genes and mutations thereof which, as discussed below, have been discovered in *Arabidobsis*. However, these methods are not limited to any particular plant type. It is expected that similar mutations in other plants will result in similar phenotypes.

It was discovered that mutating the ARF GAP domain of genes within the NEVERSHED family resulted in plants having reduced, or abolished floral abscission. Thus, embodiments of the invention include methods of preventing floral abscission by mutating the NEVERSHED gene, and more specifically, mutating the ARF GAP domain of the NEVERSHED gene.

Other embodiments of the invention include plants that overexpress mutated forms of the NEVERSHED gene. Methods of transforming plants with the NEVERSHED gene are described below.

The present invention is based, in part, upon the identification, isolation, cloning and sequencing of a novel gene family regulating abscission in plants. By the present invention, we describe several novel family members, NEVERSHED, and homologues and mutants thereof, identified in *Arabidopsis thaliana* and other plants.

Thus, in one series of embodiments, the present invention provides isolated nucleic acids including nucleotide sequences comprising or derived from the NEVERSHED genes and/or encoding polypeptides comprising or derived from the NEVERSHED proteins. The NEVERSHED sequences of the invention include the specifically disclosed sequences, splice variants of these sequences, allelic variants of these sequences, synonymous sequences, and homologous or orthologous variants of these sequences. Thus, for example, the invention provides genomic and cDNA sequences from the NEVERSHED gene. The present invention also provides allelic variants and homologous or orthologous sequences by providing methods by which such variants may be routinely obtained. The present invention also specifically provides for mutant or variants of the NEVERSHED sequences by disclosing a number of specific mutant sequences and by providing methods by which other such variants may be routinely obtained. Because the nucleic acids of the invention may be used in a variety of applications, various subsets of the NEVERSHED sequences and combinations of the NEVERSHED sequences with heterologous sequences are also provided, particularly the ARF domain. For example, for use in allele specific hybridization screening or PCR amplification techniques, subsets of the NEVERSHED sequences, including both sense and antisense sequences, and both normal and mutant sequences, as well as intronic, exonic and untranslated sequences, are provided. Such sequences may comprise a small number of consecutive nucleotides from the sequences which are disclosed or otherwise enabled herein but preferably include at least 8–10, and more preferably 9–25, consecutive nucleotides from a NEVERSHED sequence. Such sequences are particularly useful to identify modulators of NEVERSHED, including inhibitors and inducers of NEVERSHED, from, for example, crystal structures of the ARF domain. Other preferred subsets of the NEVERSHED sequences include those encoding one or more of the functional domains or antigenic determinants of the NEVERSHED proteins and, in particular, may include either normal (wild-type) or mutant sequences, particularly the ARF domain. The invention also provides for various nucleic acid constructs in which NEVERSHED sequences, either complete or subsets, are operably joined to exogenous sequences to form cloning vectors, expression vectors, fusion vectors, transgenic constructs, and the like. Thus, in accordance with another aspect of the invention, a recombinant vector for transforming a NEVERSHED sequence to cells is provided.

Embodiments of the invention also include several homologs of an *Arabidopsis thaliana* NEVERSHED gene (SEQ ID NOs 1 and 2), and mutants thereof that affect abscission. These homologs include the MKP6.22 homolog (SEQ ID NOs 9 and 10), the F13M22.5 homolog (SEQ ID NOs 11 and 12), the F17A17.28 homolog (SEQ ID NOs 13 and 14), the F5K20.10 homolog (SEQ ID NOs 15 and 16), and the MZA15.17 homolog (SEQ ID NOs 17 and 18).

Accordingly, in another series of embodiments, the present invention provides methods of screening or identifying proteins, small molecules or other compounds which are capable of inducing or inhibiting the expression of the NEVERSHED genes and proteins. The assays may be performed in vitro using transformed or non-transformed cells, immortalized cell lines, or in vivo using transformed plant models enabled herein. In particular, the assays may detect the presence of increased or decreased expression of NEVERSHED (from *Arabidopsis* or other plants) genes or proteins on the basis of increased or decreased mRNA expression, increased or decreased levels of NEVERSHED protein products, or increased or decreased levels of expression of a marker gene (e.g., beta-galactosidase, green fluorescent protein, alkaline phosphatase or luciferase) operably joined to a NEVERSHED 5' regulatory region in a recombinant construct. Cells known to express a particular NEV- ERSHED sequence, or transformed to express a particular NEVERSHED sequence, are incubated and one or more test compounds are added to the medium. After allowing a sufficient period of time (e.g., 0–72 hours) for the compound to induce or inhibit the expression of the NEVERSHED sequence, any change in levels of expression from an established baseline may be detected using any of the techniques described above.

In another series of embodiments, the present invention provides methods for identifying proteins and other compounds which bind to, or otherwise directly interact with, the NEVERSHED gene or the NEVERSHED protein. The proteins and compounds will include endogenous cellular components which interact with NEVERSHED in vivo and which, therefore, provide new targets for agricultural products, as well as recombinant, synthetic and otherwise exogenous compounds which may have NEVERSHED binding capacity and, therefore, may be candidates for defoliates. Thus, in one series of embodiments, HTS protein or DNA chips, cell lysates or tissue homogenates may be screened for proteins or other compounds which bind to one of the normal or mutant NEVERSHED genes. Alternatively, any of a variety of exogenous compounds, both naturally occurring and/or synthetic (e.g., libraries of small molecules or peptides), may be screened for NEVERSHED binding capacity.

In each of these embodiments, an assay is conducted to detect binding between NEVERSHED protein and some other moiety. The NEVERSHED in these assays may be any polypeptide comprising or derived from a normal or mutant NEVERSHED protein, including functional domains or antigenic determinants of the NEVERSHED fusion proteins, such as the ARF domain. Binding may be detected by non-specific measures (e.g., transcription modulation, altered chromatin structure, peptide production or changes in the expression of other downstream genes which can be monitored by differential display, 2D gel electrophoresis, differential hybridization, or SAGE methods) or by direct measures such as immunoprecipitation, the Biomolecular Interaction Assay (BIAcore) or alteration of protein gel electrophoresis. The preferred methods involve variations on the following techniques: (1) direct extraction by affinity chromatography; (2) co-isolation of NEVERSHED components and bound proteins or other compounds by immunoprecipitation; (3) BIAcore analysis; and (4) the yeast two-hybrid systems.

In another series of embodiments, the present invention provides for methods of identifying proteins, small molecules and other compounds capable of modulating the activity of normal or mutant NEVERSHED. In a particular aspect of the present invention, there are provided methods for identifying compounds capable of modulating specifically the ARF domain, more specifically, the ARF domain from plants and not other organisms such as mammals. Using normal cells or plants, the transformed cells and plant models of the present invention, or cells obtained from subjects bearing normal or mutant NEVERSHED genes, the present invention provides methods of identifying such compounds on the basis of their ability to affect the expression of NEVERSHED, the activity of NEVERSHED, the activity of other NEVERSHED-regulated genes, the activity of proteins that interact with normal or mutant NEVERSHED proteins, the intracellular localization of the NEVERSHED protein, changes in transcription activity, differentiation of abscission zones, metabolic measures such as the partitioning of carbon or nitrogen or nutrients, the occurrence or rate of vesicular transport, the levels or pattern of ARF-GTP, the presence or levels of membrane bound NEVERSHED, or other biochemical, histological, or physiological markers which distinguish cells bearing normal and modulated ARF activity in plants and in animals.

In accordance with another aspect of the invention, the proteins of the invention can be used as starting points for rational chemical design to provide ligands or other types of small chemical molecules. Alternatively, small molecules or other compounds identified by the above-described screening assays may serve as "lead compounds" in design of modulators of abscission in plants.

In order to understand genetic control of floral abscission, we developed mutants in which floral abscission was specifically and completely blocked. Genetic screens of EMS-mutagenized populations led to the identification and characterization of two independent alleles of a recessive *Arabidopsis* mutant in which floral organ abscission fails to occur throughout the lifetime of the plant. Because floral abscission, or organ shedding of the sepals, petals and stamens, does not take place in these mutants, the corresponding gene has been named NEVERSHED. Through characterization of an *Arabidopsis* mutant which fails to shed its floral organs, and by determining the molecular basis for these defects, abscission zone development can be examined and the cascades of gene activity that lead to the differentiation of this cell type can be determined.

As used herein, the term "substantially pure" as used herein refers to polypeptides which are substantially free of other proteins, lipids, carbohydrates or other materials with which it is naturally associated. One skilled in the art can purify a polypeptide using standard techniques for protein purification. The purity of a polypeptide can also be determined by amino-terminal amino acid sequence analysis.

Embodiments of the invention also include functional NEVERSHED polypeptides, and functional fragments thereof. As used herein, the term "functional polypeptide" refers to a polypeptide which possesses biological function or activity which is identified through a defined functional assay and which is associated with a particular biologic, morphologic, or phenotypic alteration in the cell. The term "functional fragments of NEVERSHED polypeptide", refers to all fragments of NEVERSHED that retain NEVERSHED activity, e.g., preventing organ abscission. Biologically functional fragments, for example, can vary in size from a polypeptide fragment as small as an epitope capable of binding an antibody molecule to a large polypeptide capable of participating in the characteristic induction or programming of phenotypic changes within a cell.

Many modifications of the NEVERSHED primary amino acid sequence may result in plants having reduced or abolished organ abscission. Such modifications may be deliberate, as by site-directed mutagenesis, or may be spontaneous. All of the polypeptides produced by these modifications are included herein as long as the biological activity of NEVERSHED is present. Further, deletion of one or more amino acids can also result in a modification of the structure of the resultant molecule without significantly altering its activity. This can lead to the development of a smaller active molecule which could have broader utility. For example, it may be possible to remove amino or carboxy terminal amino acids required for NEVERSHED activity.

NEVERSHED polypeptides includes amino acid sequences substantially the same as the sequence set forth in SEQ ID NO:2, including mutants that result in plants having decreased organ abscission. The term "substantially the same" refers to amino acid sequences that retain the activity of NEVERSHED as described herein. The NEVERSHED polypeptides of the invention include conservative variations of the polypeptide sequence.

The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

NEVERSHED proteins can be analyzed by standard SDS-PAGE and/or immunoprecipitation analysis and/or Western blot analysis, for example. In addition, the in vitro synthesized (IVS) protein assay as described in the present examples can be used to analyze NEVERSHED protein product.

Embodiments of the invention also provide an isolated polynucleotide sequence encoding a polypeptide having the amino acid sequence of SEQ ID NO:2. The term "isolated" as used herein includes polynucleotides substantially free of other nucleic acids, proteins, lipids, carbohydrates or other materials with which it is naturally associated. Polynucleotide sequences of the invention include DNA, cDNA and RNA sequences which encode NEVERSHED. It is understood that polynucleotides encoding all or varying portions of NEVERSHED are included herein, as long as they encode a polypeptide with NEVERSHED activity. Such polynucleotides include naturally occurring, synthetic, and intentionally manipulated polynucleotides as well as splice variants. For example, portions of the mRNA sequence may be altered due to alternate RNA splicing patterns or the use of alternate promoters for RNA transcription.

Moreover, NEVERSHED polynucleotides include polynucleotides having alterations in the nucleic acid sequence which still encode a polypeptide having the ability to prevent organ abscission. Alterations in NEVERSHED nucleic acids include but are not limited to intragenic mutations (e.g., point mutation, nonsense (stop), antisense, splice site and frameshift) and heterozygous or homozygous deletions. Detection of such alterations can be done by standard methods known to those of skill in the art including sequence analysis, Southern blot analysis, PCR based analyses (e.g., multiplex PCR, sequence tagged sites (STSs)) and in situ hybridization. Embodiments of the invention also include anti-sense polynucleotide sequences.

The polynucleotides described herein include sequences that are degenerate as a result of the genetic code. There are 20 natural amino acids, most of which are specified by more than one codon. Therefore, all degenerate nucleotide sequences are included in the invention as long as the amino acid sequence of NEVERSHED polypeptide encoded by such nucleotide sequences retains NEVERSHED activity. A "functional polynucleotide" denotes a polynucleotide which encodes a functional polypeptide as described herein. In addition, embodiments of the invention also include a polynucleotide encoding a polypeptide having the biological activity of an amino acid sequence of SEQ ID NO:2 and having at least one epitope for an antibody immunoreactive with NEVERSHED polypeptide.

As used herein, the terms "polynucleotides" and "nucleic acid sequences" refer to DNA, RNA and cDNA sequences.

The polynucleotide encoding NEVERSHED includes the nucleotide sequence in SEQ ID NO:1, as well as nucleic acid sequences complementary to that sequence. A complementary sequence may include an antisense nucleotide. When the sequence is RNA, the deoxyribonucleotides A, G, C, and T of SEQ ID NO:1 are replaced by ribonucleotides A, G, C, and U, respectively. Also included in the invention are fragments ("probes") of the above-described nucleic acid sequences that are at least 15 bases in length, which is sufficient to permit the probe to selectively hybridize to DNA that encodes the protein of SEQ ID NO: 1.

"Hybridization" refers to the process by which a nucleic acid strand joins with a complementary strand through base pairing. Hybridization reactions can be sensitive and selective so that a particular sequence of interest can be identified even in samples in which it is present at low concentrations. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 n/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

"Selective hybridization" as used herein refers to hybridization under moderately stringent or highly stringent physiological conditions (See, for example, the techniques described in Maniatis et al., 1989, *Molecular Cloning: A Laboratory Manual,* Cold Spring Harbor Laboratory, N.Y., which is incorporated by reference herein in its entirety), which distinguishes related from unrelated NEVERSHED nucleotide sequences.

Another aspect of the invention is polypeptides or fragments thereof which have at least about 70%, at least about 80%, at least about 85%, at least about 90%, at least about 95%, or more than about 95% homology to one of the polypeptides of SEQ ID NO:2, and sequences substantially identical thereto, or a fragment comprising at least 5, 10, 15, 20, 25, 30, 35, 40, 50, 75, 100, or 150 consecutive amino acids thereof. Homology may be determined using any of the methods described herein which align the polypeptides or fragments being compared and determines the extent of amino acid identity or similarity between them. It will be appreciated that amino acid "homology" includes conservative amino acid substitutions such as those described above.

The polypeptides or fragments having homology to one of the polypeptides of SEQ ID NO:2, and sequences substantially identical thereto, or a fragment comprising at least about 5, 10, 15, 20, 25, 30, 35, 40, 50, 75, 100, or 150 consecutive amino acids thereof may be obtained by isolating the nucleic acids encoding them using the techniques described herein Alternatively, the homologous polypeptides or fragments may be obtained through biochemical enrichment or purification procedures. The sequence of potentially homologous polypeptides or fragments may be determined by proteolytic digestion, gel electrophoresis and/or microsequencing. The sequence of the prospective homologous polypeptide or fragment can be compared to one of the polypeptides of SEQ ID NO:2, and sequences substantially identical thereto, or a fragment comprising at least about 5, 10, 15, 20, 25, 30, 35, 40, 50, 75, 100, or 150 consecutive amino acids thereof using any of the programs described above.

Also included in embodiments of the invention are nucleotide sequences that are greater than 70% homologous with the sequence of SEQ ID NO: 1, but still retain the ability to decrease or prevent organ abscission. Other embodiments of the invention include nucleotide sequences that are greater than 75%, 80%, 85%, 90% or 95% homologous with the sequence of SEQ ID NO: 1, but still retain the ability to decrease or prevent organ or flower abscission.

Specifically disclosed herein is a genomic sequence for NEVERSHED. DNA sequences of the invention can be obtained by several methods. For example, the DNA can be isolated using hybridization or computer-based techniques which are well known in the art. Such techniques include, but are not limited to: 1) hybridization of genomic or cDNA libraries with probes to detect homologous nucleotide sequences; 2) antibody screening of expression libraries to detect cloned DNA fragments with shared structural features; 3) polymerase chain reaction (PCR) on genomic DNA or cDNA using primers capable of annealing to the DNA sequence of interest; 4) computer searches of sequence databases for similar sequences; and 5) differential screening of a subtracted DNA library.

Screening procedures which rely on nucleic acid hybridization make it possible to isolate any gene sequence from any organism, provided the appropriate probe is available. Oligonucleotide probes, which correspond to a part of the NEVERSHED sequence encoding the protein in question, can be synthesized chemically. This requires that short, oligopeptide stretches of the amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace et al., 1981, *Nucl. Acid Res.*, 9:879, which is incorporated by reference herein in its entirety). Alternatively, a subtractive library, as illustrated herein is useful for elimination of non-specific cDNA clones.

Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay et al., 1983, *Nucl. Acid Res.*, 11:2325, which is incorporated by reference herein in its entirety).

A cDNA expression library, such as lambda gt11, can be screened indirectly for NEVERSHED peptides using antibodies specific for NEVERSHED. Such antibodies can be either polyclonally or monoclonally derived and used to detect expression product indicative of the presence of NEVERSHED cDNA.

DNA sequences encoding NEVERSHED can be expressed in vitro by DNA transfer into a suitable host cell. "Host cells" are cells in which a vector can be propagated and its DNA expressed. The term also includes any progeny or graft material, for example, of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

As part of the present invention, the NEVERSHED polynucleotide sequences may be inserted into a recombinant expression vector. The terms "recombinant expression vector" or "expression vector" refer to a plasmid, virus or other vehicle known in the art that has been manipulated by insertion or incorporation of the NEVERSHED genetic sequence. Such expression vectors contain a promoter sequence which facilitates the efficient transcription of the inserted NEVERSHED sequence. The expression vector typically contains an origin of replication, a promoter, as well as specific genes which allow phenotypic selection of the transformed cells.

Methods which are well known to those skilled in the art can be used to construct expression vectors containing the NEVERSHED coding sequence and appropriate transcriptional/translational control signals. These methods include in vitro recombinant DNA techniques, synthetic techniques, and in vivo recombination/genetic techniques.

A variety of host-expression vector systems may be utilized to express the NEVERSHED coding sequence. These include but are not limited to microorganisms such as bacteria transformed with recombinant bacteriophage DNA, plasmid DNA or cosmid DNA expression vectors containing the NEVERSHED coding sequence; yeast transformed with recombinant yeast expression vectors containing the NEVERSHED coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the NEVERSHED coding sequence; insect cell systems infected with recombinant virus expression vectors (e.g., baculovirus) containing the NEVERSHED coding sequence; or animal cell systems infected with recombinant virus expression vectors (e.g., retroviruses, adenovirus, vaccinia virus) containing the NEVERSHED coding sequence, or transformed animal cell systems engineered for stable expression.

Depending on the host/vector system utilized, any of a number of suitable transcription and translation elements, including constitutive and inducible promoters, transcription enhancer elements, transcription terminators, etc. may be used in the expression vector (see e.g., Bitter et al., 1987, *Methods in Enzymol* 153:516–544, which is incorporated by reference herein in its entirety). For example, when cloning in bacterial systems, inducible promoters such as pL of bacteriophage gamma, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted NEVERSHED coding sequence.

Isolation and purification of recombinantly expressed polypeptide, or fragments thereof, may be carried out by conventional means including preparative chromatography and immunological separations involving monoclonal or polyclonal antibodies.

Aspects of the invention also include antibodies immunoreactive with NEVERSHED polypeptide or antigenic fragments thereof. Antibody which consists essentially of pooled monoclonal antibodies with different epitopic specificities, as well as distinct monoclonal antibody preparations are provided. Monoclonal antibodies are made from antigen containing fragments of the protein by methods well known to those skilled in the art (Kohler, et al., 1975, *Nature* 256:495, which is incorporated by reference herein in its entirety).

The term "antibody" as used in this invention includes intact molecules as well as fragments thereof, such as Fab, F(ab')2, and Fv which are capable of binding to an epitopic determinant present in NEVERSHED polypeptide. Such antibody fragments retain some ability to selectively bind with its antigen or receptor.

Methods of making these fragments are known in the art. (See for example, Harlow and Lane, 1988, *Antibodies: A Laboratory Manual,* Cold Spring Harbor Laboratory, N.Y., which is incorporated by reference herein in its entirety).

As used in this invention, the term "epitope" refers to an antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to the NEVERSHED polypeptide of the invention can be prepared using an intact polypeptide or fragments containing small peptides of interest as the immunizing antigen. For example, it may be desirable to produce antibodies that specifically bind to the N- or C-terminal domains of NEVERSHED. The polypeptide or peptide used to immunize an animal which is derived from translated cDNA or chemically synthesized which can be conjugated to a carrier protein, if desired. Such commonly used carriers which are chemically coupled to the immunizing peptide include keyhole limpet hemocyanin (KLH), thyroglobulin, bovine serum albumin (BSA), and tetanus toxoid.

Polyclonal or monoclonal antibodies can be further purified, for example, by binding to and eluting from a matrix to which the polypeptide or a peptide to which the antibodies were raised is bound. Those of skill in the art will know of various techniques common in the immunology arts for purification and/or concentration of polyclonal antibodies, as well as monoclonal antibodies. (See for example, Coligan et al., 1994, *Unit 9, Current Protocols in Immunology,* Wiley Interscience, which is incorporated by reference herein in its entirety).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

In another embodiment, the embodiments of the invention provide a method for producing a genetically modified plant characterized as having decreased or abolished abscission as compared to a plant which has not been genetically modified (e.g., a wild-type plant). The method includes the steps of contacting a plant cell with at least one vector containing at least one nucleic acid sequence encoding a NEVERSHED mutant gene, wherein the nucleic acid sequence is operably associated with a promoter, to obtain a transformed plant cell; producing a plant from the transformed plant cell; and thereafter selecting a plant exhibiting reduced abscission. The resulting mutant phenotype will be known as the nevershed mutant.

The term "genetic modification" as used herein refers to the introduction of one or more heterologous nucleic acid sequences, e.g., a NEVERSHED mutant gene, into one or more plant cells, which can generate whole, sexually competent, viable plants having the nevershed mutant phenotype. The term "genetically modified" as used herein refers to a plant which has been generated through the aforementioned process. Genetically modified plants of the invention are capable of self-pollinating or cross-pollinating with other plants of the same species so that the foreign gene, carried in the germ line, can be inserted into or bred into agriculturally useful plant varieties. The term "plant cell" as used herein refers to protoplasts, gamete producing cells, and cells which regenerate into whole plants. Accordingly, a seed comprising multiple plant cells capable of regenerating into a whole plant, is included in the definition of "plant cell".

As used herein, the term "plant" refers to either a whole plant, a plant part, a plant cell, or a group of plant cells, such as plant tissue, for example. Plantlets are also included within the meaning of "plant". Plants included in the invention are any plants amenable to transformation techniques, including angiosperms, gymnosperms, monocotyledons and dicotyledons.

Examples of monocotyledonous plants include, but are not limited to, asparagus, field and sweet corn, barley, wheat, rice, sorghum, onion, pearl millet, rye and oats. Examples of dicotyledonous plants include, but are not limited to tomato, tobacco, cotton, rapeseed, field beans, soybeans, peppers, lettuce, peas, alfalfa, clover, cole crops or *Brassica oleracea* (e.g., cabbage, broccoli, cauliflower, brussel sprouts), radish, carrot, beets, eggplant, spinach, cucumber, squash, melons, cantaloupe, sunflowers and various ornamentals. Woody species include poplar, pine, sequoia, cedar, oak, etc.

The term "heterologous nucleic acid sequence" as used herein refers to a nucleic acid foreign to the recipient plant host or, native to the host if the native nucleic acid is substantially modified from its original form. For example, the term includes a nucleic acid originating in the host species, where such sequence is operably linked to a promoter that differs from the natural or wild-type promoter. In one embodiment, at least one nucleic acid sequence encoding a NEVERSHED mutant is operably linked with a promoter. In another embodiment, a different gene having a mutated ARF GAP domain is operably linked with a promoter. It may be desirable to introduce more than one copy of a NEVERSHED mutant polynucleotide into a plant for enhanced expression. For example, multiple copies of the gene would have the effect of increasing production of the NEVERSHED mutant gene in the plant.

Genetically modified plants of the present invention are produced by contacting a plant cell with a vector including at least one nucleic acid sequence encoding a NEVERSHED mutant. To be effective once introduced into plant cells, the mutant NEVERSHED nucleic acid sequence must be operably associated with a promoter which is effective in the plant cells to cause transcription of NEVERSHED mutant. Additionally, a polyadenylation sequence or transcription control sequence, also recognized in plant cells may also be employed. It is preferred that the vector harboring the nucleic acid sequence to be inserted also contain one or more selectable marker genes so that the transformed cells can be selected from non-transformed cells in culture, as described herein.

The term "operably associated" refers to finctional linkage between a promoter sequence and a nucleic acid sequence regulated by the promoter. The operably linked promoter controls the expression of the nucleic acid sequence.

The expression of structural genes may be driven by a number of promoters. Although the endogenous, or native promoter of a structural gene of interest may be utilized for transcriptional regulation of the gene, preferably, the promoter is a foreign regulatory sequence. For plant expression vectors, suitable viral promoters include the 35S RNA and 19S RNA promoters of CaMV (Brisson, et al., 1984, *Nature* 310:511; Odell, et al., 1985, *Nature* 313:810, both of which are incorporated by reference herein in their entireties); the full-length transcript promoter from Figwort Mosaic Virus (FMV) (Gowda, et al., 1989, *J. Cell Biochem.,* 13D: 301, which is incorporated by reference herein in its entirety) and the coat protein promoter to TMV (Takamatsu, et al., 1987, *EMBO J.* 6:307, which is incorporated by reference herein in its entirety). Alternatively, plant promoters such as the light-inducible promoter from the small subunit of ribulose bis-phosphate carboxylase (ssRUBISCO) (Coruzzi, et al., 1984, *EMBO J.,* 3:1671; Broglie, et al., 1984, *Science* 224:838, both of which are incorporated by reference herein in their entireties); mannopine synthase promoter (Velten, et al., 1984, *EMBO J.,* 3:2723, which is incorporated by reference herein in its entirety) nopaline synthase (NOS) and octopine synthase (OCS) promoters (carried on tumor-inducing plasmids of *Agrobacterium tumefaciens*) or heat shock promoters, e.g, soybean hsp17.5-E or hsp17.3-B (Gurley, et al., 1986, *Mol. Cell. Biol.* 6:559; Severin, et al., 1990, *Plant Mol. Biol.* 15:827, both of which are incorporated by reference herein in their entireties) may be used.

Promoters useful in the invention include both natural constitutive and inducible promoters as well as engineered promoters. One embodiment of a promoter can be found in SEQ ID NO: 7, which includes the sequences upstream from SEQ ID NO:1. The CaMV promoters are examples of constitutive promoters. To be most useful, an inducible promoter should 1) provide low expression in the absence of the inducer; 2) provide high expression in the presence of the inducer; 3) use an induction scheme that does not interfere with the normal physiology of the plant; and 4) have no effect on the expression of other genes. Examples of inducible promoters useful in plants include those induced by chemical means, such as the yeast metallothionein promoter which is activated by copper ions (Mett, et al., 1993, *Proc. Natl. Acad. Sci.* U.S.A. 90:4567, which is incorporated by reference herein in its entirety); In2-1 and In2-2 regulator sequences which are activated by substituted benzenesulfonamides, e.g., herbicide safeners (Hershey, et al., 1991, *Plant Mol. Biol.* 17:679, which is incorporated by reference herein in its entirety); and the GRE regulatory sequences which are induced by glucocorticoids (Schena, et al., 1991, *Proc. Natl. Acad Sci.* U.S.A 88:10421, which is incorporated by reference herein in its entirety). Other promoters, both constitutive and inducible will be known to those of skill in the art.

The particular promoter selected should be capable of causing sufficient expression to result in the production of an effective amount of structural gene product, e.g., a NEVERSHED mutant, to cause increased yield and/or increased biomass. The promoters used in the vector constructs of the present invention may be modified, if desired, to affect their control characteristics.

Tissue specific promoters may also be utilized in the present invention. An example of a tissue specific promoter is the promoter active in shoot meristems (Atanassova, et al., 1992, *Plant J.* 2:291, which is incorporated by reference herein in its entirety). Other tissue specific promoters useful in transgenic plants, including the cdc2a promoter and cyc07 promoter, will be known to those of skill in the art. (See for example, Ito, et al., 1994, *Plant Mol. Biol.* 24:863; Martinez, et al., 1992, *Proc. Natl. Acad. Sci. USA* 89:7360; Medford, et al., 1991, *Plant Cell* 3:359; Terada, et al., 1993, *Plant Journal* 3:241; Wissenbach, et al., 1993, *Plant Journal* 4:411, all of which are incorporated by reference herein in their entireties).

Optionally, a selectable marker may be associated with the nucleic acid sequence to be inserted. As used herein, the term "marker" refers to a gene encoding a trait or a phenotype which permits the selection of, or the screening for, a plant or plant cell containing the marker. Preferably, the marker gene is an antibiotic resistance gene whereby the appropriate antibiotic can be used to select for transformed cells from among cells that are not transformed. Examples of suitable selectable markers include adenosine deaminase, dihydrofolate reductase, hygromycin-B-phospho-transferase, thymidine kinase, xanthineguanine phospho-ribosyl-transferase and amino-glycoside 3'-O-phospho-transferase II (kanamycin, neomycin and G418 resistance). Other suitable markers will be known to those of skill in the art.

Vector(s) employed in the present invention for transformation of a plant cell include a nucleic acid sequence encoding a NEVERSHED mutant, operably associated with a promoter. To commence a transformation process in accordance with the present invention, it is first necessary to construct a suitable vector and properly introduce it into the plant cell. Details of the construction of vectors utilized herein are known to those skilled in the art of plant genetic engineering.

NEVERSHED nucleic acid sequences utilized in the present invention can be introduced into plant cells using Ti plasmids of *Agrobacterium tumefaciens,* root-inducing (Ri) plasmids, and plant virus vectors. (For reviews of such techniques see, for example, Weissbach & Weissbach, 1988, *Methods for Plant Molecular Biology,* Academic Press, NY, Section VIII, pp. 421–463; and Grierson & Corey, 1988, *Plant Molecular Biology,* 2d Ed., Blackie, London, Ch. 7–9, and Horsch, et al., 1985, *Science* 227:1229, all of which are incorporated by reference herein in their entireties). In addition to plant transformation vectors derived from the Ti or root-inducing (Ri) plasmids of *Agrobacterium,* alternative methods may involve, for example, the use of liposomes, electroporation, chemicals that increase free DNA uptake, transformation using viruses or pollen and the use of microprojection.

One of skill in the art will be able to select an appropriate vector for introducing the NEVERSHED-encoding nucleic acid sequence in a relatively intact state. Thus, any vector which will produce a plant carrying the introduced DNA sequence should be sufficient. Even use of a naked piece of DNA would be expected to confer the properties of this invention, though at low efficiency. The selection of the vector, or whether to use a vector, is typically guided by the method of transformation selected.

The transformation of plants in accordance with the invention may be carried out in essentially any of the various ways known to those skilled in the art of plant molecular biology. (See, for example, *Methods of Enzymology*, Vol. 153, 1987, Wu and Grossman, Eds., Academic Press, which is incorporated by reference herein in its entirety). As used herein, the term "transformation" means alteration of the genotype of a host plant by the introduction of a NEVERSHED nucleic acid sequence or a NEVERSHED mutant nucleic acid sequence.

For example, a NEVERSHED nucleic acid sequence can be introduced into a plant cell utilizing *Agrobacterium tumefaciens* containing the Ti plasmid, as mentioned briefly above. In using an *A. tumefaciens* culture as a transformation vehicle, it is most advantageous to use a non-oncogenic strain of *Agrobacterium* as the vector carrier so that normal non-oncogenic differentiation of the transformed tissues is possible. It is also preferred that the *Agrobacterium* harbor a binary Ti plasmid system. Such a binary system comprises 1) a first Ti plasmid having a virulence region essential for the introduction of transfer DNA (T-DNA) into plants, and 2) a chimeric plasmid. The latter contains at least one border region of the T-DNA region of a wild-type Ti plasmid flanking the nucleic acid to be transferred. Binary Ti plasmid systems have been shown effective to transform plant cells (De Framond, 1983, *Biotechnology* 1: 262; Hoekema, et al., 1983, *Nature* 303:179, both of which are incorporated by reference herein in their entireties). Such a binary system is preferred because it does not require integration into the Ti plasmid of *Agrobacterium*, which is an older methodology.

Methods involving the use of *Agrobacterium* in transformation according to the present invention include, but are not limited to: 1) co-cultivation of *Agrobacterium* with cultured isolated protoplasts; 2) transformation of plant cells or tissues with *Agrobacterium*; or 3) transformation of seeds, apices or meristems with *Agrobacterium*. In addition, gene transfer can be accomplished by in planta transformation by *Agrobacteriuin*, as described by Bechtold, et al., (C. R. Acad. Sci. Paris, 316:1194, 1993, which is incorporated by reference herein in its entirety) and exemplified in the Examples herein. This approach is based on the vacuum infiltration of a suspension of *Agrobacterium* cells.

One method of introducing NEVERSHED-encoding nucleic acid into plant cells is to infect such plant cells, an explant, a meristem or a seed, with transformed *Agrobacterium tumefaciens* as described above. Under appropriate conditions known in the art, the transformed plant cells are grown to form shoots, roots, and develop further into plants.

Alternatively, NEVERSHED encoding nucleic acid sequences can be introduced into a plant cell using mechanical or chemical means. For example, the nucleic acid can be mechanically transferred into the plant cell by microinjection using a micropipette. Alternatively, the nucleic acid may be transferred into the plant cell by using polyethylene glycol which forms a precipitation complex with genetic material that is taken up by the cell.

One or more NEVERSHED nucleic acid sequences can also be introduced into plant cells by electroporation (Fromm et al., 1985, *Proc. Natl. Acad. Sci.* U.S.A. 82:5824, which is incorporated by reference herein in its entirety). In this technique, plant protoplasts are electroporated in the presence of vectors or nucleic acids containing the relevant nucleic acid sequences. Electrical impulses of high field strength reversibly permeabilize membranes allowing the introduction of nucleic acids. Electroporated plant protoplasts reform the cell wall, divide and form a plant callus. Selection of the transformed plant cells with the transformed gene can be accomplished using phenotypic markers as described herein.

Another method for introducing one or more NEVERSHED nucleic acid sequences into a plant cell is high velocity ballistic penetration by small particles with the nucleic acid to be introduced contained either within the matrix of such particles, or on the surface thereof (Klein, et al., 1987, *Nature* 327:70, which is incorporated by reference herein in its entirety). Bombardment transformation methods are also described in Sanford et al. (1991, *BioTechniques* 3:3–16) and Klein et al. (1992, *Bio/Techniques* 10:286), both of which are incorporated by reference herein in their entireties. Although typically only a single introduction of a new nucleic acid sequence is required, this method particularly provides for multiple introductions.

Cauliflower mosaic virus (CaMV) may also be used as a vector for introducing nucleic acid into plant cells (U.S. Pat. No. 4,407,956, which is incorporated by reference herein in its entirety). CaMV viral DNA genome is inserted into a parent bacterial plasmid creating a recombinant DNA molecule which can be propagated in bacteria. After cloning, the recombinant plasmid again may be cloned and further modified by introduction of the desired nucleic acid sequence. The modified viral portion of the recombinant plasmid is then excised from the parent bacterial plasmid, and used to inoculate the plant cells or plants.

As used herein, the term "contacting" refers to any means of introducing NEVERSHED into the plant cell, including chemical and physical means as described above. Preferably, contacting refers to introducing the nucleic acid or vector into plant cells (including an explant, a meristem or a seed), via *Agrobacterium tumefaciens* transformed with the NEVERSHED-encoding nucleic acid as described above.

Normally, a plant cell is regenerated to obtain a whole plant from the transformation process. The immediate product of the transformation is referred to as a "transgenote". The term "growing" or "regeneration" as used herein means growing a whole plant from a plant cell, a group of plant cells, a plant part (including seeds), or a plant piece (e.g., from a protoplast, callus, or tissue part).

Regeneration from protoplasts varies from species to species of plants, but generally a suspension of protoplasts is first made. In certain species, embryo formation can then be induced from the protoplast suspension, to the stage of ripening and germination as natural embryos. The culture media will generally contain various amino acids and hormones, necessary for growth and regeneration. Examples of hormones utilized include auxins and cytokinins. It is sometimes advantageous to add glutamic acid and proline to the medium, especially for plant species such as corn and alfalfa. Efficient regeneration will depend on the medium, on the genotype, and on the history of the culture. If these variables are controlled, regeneration is reproducible.

Regeneration also occurs from plant callus, explants, organs or parts. Transformation can be performed in the context of organ or plant part regeneration. (See *Methods in Enzymology*, Vol. 118 and Klee, et al., 1987, *Annual Review of Plant Physiology*, 38:467, which is incorporated by reference herein in its entirety). Utilizing the leaf disk-transformation-regeneration method of Horsch, et al. (1985, *Science* 227:1229, which is incorporated by reference herein in its entirety), disks are cultured on selective media, followed by shoot formation in about 2–4 weeks. Shoots that develop are excised from calli and transplanted to appropriate root-inducing selective medium. Rooted plantlets are transplanted to soil as soon as possible after roots appear. The plantlets can be repotted as required, until reaching maturity.

In vegetatively propagated crops, the mature transgenic plants are propagated by utilizing cuttings or tissue culture techniques to produce multiple identical plants. Selection of desirable transgenotes is made and new varieties are obtained and propagated vegetatively for commercial use.

In seed propagated crops, the mature transgenic plants can be self crossed to produce a homozygous inbred plant. The resulting inbred plant produces seed containing the newly introduced foreign gene(s). These seeds can be grown to produce plants that would produce the selected phenotype, e.g increased yield.

Parts obtained from regenerated plant, such as flowers, seeds, leaves, branches, roots, fruit, and the like are included in the invention, provided that these parts comprise cells that have been transformed as described. Progeny and variants, and mutants of the regenerated plants are also included within the scope of the invention, provided that these parts comprise the introduced nucleic acid sequences.

Plants exhibiting decreased or abolished abscission as compared with wild-type plants can be selected by visual observation. The invention includes plants produced by the method of the invention, as well as plant tissue and seeds.

In yet another embodiment, the invention provides a method for producing a genetically modified plant cell such that a plant produced from said cell has decreased or abolished abscission as compared with a wild-type plant. The method includes contacting the plant cell with a NEVERSHED nucleic acid sequence to obtain a transformed plant cell; growing the transformed plant cell under plant forming conditions to obtain a plant having increased yield. Conditions such as environmental and promoter inducing conditions vary from species to species, but should be the same within a species.

In another embodiment, the invention provides a method of producing a plant having decreased abscission by contacting a susceptible plant with a NEVERSHED promoter-inducing amount of an agent which induces NEVERSHED gene expression, wherein induction of NEVERSHED gene expression results in production of a plant having decreased abscission as compared to a plant not contacted with the agent.

A "susceptible plant" refers to a plant that can be induced to utilize its endogenous NEVERSHED gene to achieve decreased abscission. The term "promoter inducing amount" refers to that amount of an agent necessary to elevate NEVERSHED gene expression above NEVERSHED expression in a plant cell not contacted with the agent. For example, a transcription factor or a chemical agent may be used to elevate gene expression from NEVERSHED native promoter, thus inducing the promoter and NEVERSHED gene expression.

The above disclosure generally describes the present invention. A more complete understanding can be obtained by reference to the following specific examples which are provided herein for purposes of illustration only and are not intended to limit the scope of the invention.

EXAMPLES

Example 1

Isolation and Identification of the Nevershed Mutant in *Arabidopsis*

Seeds of *Arabidopsis thaliana* ecotype Landsberg erecta (Ler) were mutagenized by exposure to ethyl methane-sulphonate (EMS) using standard techniques, for example as described in Lilgejren et al. (2000, *Nature* 404: 766–770, which is incorporated by reference herein in its entirety). EMS-exposed seeds were germinated, and plants were screened for unusual phenotypes. As a result of two unrelated EMS screens, two *Arabidopsis* mutants were identified having a phenotype in which floral organ abscission, more particularly organ shedding of the sepals, petals and stamens, failed to occur throughout the lifetime of the plant. This mutant phenotype was called nevershed because floral abscission, or organ shedding of sepals, petals and stamens, did not take place in this mutant. The two EMS mutants were called nev-1 and nev-2.

It was then determined that these mutants having the same phenotype were independent alleles the same locus, termed herein "nev", and represented a recessive *Arabidopsis* mutant termed herein "nevershed". The corresponding gene has been called NEVERSHED.

Example 2

Cloning of the NEVERSHED Gene and Mutant Alleles

Using a standard map-based cloning approach (Konieczny and Ausubel, 1993, *Plant J* 4: 403–410, which is incorporated by reference herein in its entirety), the nev locus was mapped to chromosome 5 as follows. nev-1 (SEQ ID NO: 3) and nev-2 (SEQ ID NO: 5) mutants, in the Landsberg erecta (Ler) ecotype, were crossed to wild-type plants of the Columbia (Col) ecotype. After scoring the nevershed phenotype in the F2 generation, CAPS markers were used to map the mutation to chromosome 5 (Konieczny and Ausubel, 1993, supra, which is incorporated by reference herein in its entirety). By using additional CAPS markers on chromosome 5, the nev locus was mapped to an interval of ~37.5 kb between the CER970 and RPK markers the on bacterial artificial chromosomes (BACs) MDK4 (GenBank Accession No. AB010695) and GA469 (GenBank Accession No. AP000380), respectively. FIG. 1 shows the structure of the relevant region of chromosome 5. The genomic sequence can be found in SEQ ID NO: 8.

The open reading frames of 8 of the 11 annotated genes in this interval were sequenced. It was discovered that the nev-2 mutant contained a single nucleotide mutation (G to A) in the 7th exon of the gene annotated as MDK4.13. Analysis of this DNA sequence indicates that the nev-2 mutation would result in a truncated protein of 197 amino acids (SEQ ID NO: 6), as the nucleotide substitution from C to T present at position 592 of SEQ ID NO: 5 (the nev-2 coding sequence) caused a glutamine codon (CAG) to be altered to a stop codon (TAG). The nev-2 mutation fell within the ARF GAP domain of the NEVERSHED gene (FIG. 1).

Upon sequencing the MDK4.13 open reading frame from the nev-1 mutant, a single nucleotide mutation (C to T) was found in the 3rd exon of the gene annotated as MDK4.13. This resulted in a G to A modification at position 152 of SEQ ID NO. 3 (the nev-1 coding sequence), altering a cysteine codon to a tyrosine codon. The resulting protein sequence (SEQ ID NO. 4) therefore has the amino acid tyrosine at position 51 rather than the amino acid cysteine. This particular cysteine is one of 4 cysteines that constitute a conserved zinc finger motif in the predicted ADP-Ribosylation Factor GTPase Activating Protein (ARF GAP) domain of the protein corresponding to MDK4.13. The nev-1 mutation fell within the ARF GAP domain of the NEVERSHED gene (FIG. 2).

The gene annotated as MDK4.13 is a predicted gene found in the Arabidopsis BAC known as MDK4 (GenBank Accession No. AB010695), and the 11 predicted exons of MDK4.13 located between positions 60024 and 63828 on BAC MDK4 can be joined to produce a protein annotated as BAB10754.1 (SEQ ID NO: 2) The identification of two independent mutations in this gene in both of the two nevershed mutants strongly suggests that the gene annotated as MDK4.13 is responsible for the discovered phenotypes. It follows, therefore, that the protein encoded by coding sequences of MKD4.13 is the NEVERSHED protein, and mutations of this protein result in a decrease or loss of organ/floral abscission.

Comparing the amino acid sequence of the NEVERSHED gene with other protein sequences indicates a predicted ADP-Ribosylation Factor GTPase Activating Protein (ARF GAP) domain having homology to ARF GAP proteins from a wide taxonomic distribution (FIG. 2). Structurally diverse GAPs are associated with all families of small GTP binding proteins, acting as signal terminators and possibly also in some cases as effectors downstream of the GTP binding protein (Boguski & McCormick 1993 *Nature* 366: 643–653, which is incorporated by reference herein in its entirety). ADP-ribosylation factors (ARFs) are 20-kDa guanine nucleotide-binding proteins, members of the Ras GTPase superfamily that were initially recognized and purified because of their ability to stimulate the ADP-ribosyltransferase activity of the cholera toxin A subunit. Like other GTP binding proteins, ARF becomes activated upon the binding of GTP, whereas GTP hydrolysis acts as a turn-off signal. The fact that purified ARF proteins have negligible GTPase activity has suggested that GTP hydrolysis by ARFs is dependent on a GTPase-activating protein (GAP). ARFs are critical components of several different vesicular trafficking pathways in all eukaryotic cells and activators of specific phospholipase Ds (PLDs).

Example 3

Expression of NEVERSHED and NEVERSHED-regulated Genes

In one embodiment, RNA blot and in situ hybridization analyses using standard procedures, are carried out to determine the temporal and spatial expression profile of NEVERSHED, preferably using *Arabidopsis* plants transformed with an expression vector containing the NEVERSHED promoter fused to the β-glucuronidase reporter gene. In other embodiments, expression of NEVERSHED and/or NEVERSHED-regulated genes are carried out under a variety of conditions to characterize the function of the NEVERSHED gene and the NEVERSHED protein. One of skill of the art can design further studies of NEVERSHED and/or NEVERSHED-regulated genes tailored according to sequence-based homology predictions and results from other studies of NEVERSHED function.

NEVERSHED and various nevershed mutants provide tools for studying the genetic pathways involved in *Arabidopsis* abscission zone development. These tools can be used to determine the genes involved in abscission zone development in other plant species. In particular, the identification of genes that act upstream and downstream of NEVERSHED may indicate the genes and pathways involved in regulating the development of abscicssion zones in plants. The discovery that NEVERSHED has a domain with strong homology to ARF GAP indicates a potential mechanism by which NEVERSHED exerts control over the development of abscission zones.

Example 4

Expression of NEVERSHED: Microarray Analysis and Expression Profiling

Both microarray analyses and the existence of numerous enhancer-trap lines with abscission zone expression profiles will allow extensive investigations of genes involved in abscission development. Collections of T-DNA tagged lines generated over the last few years, with some having more than 150,000 individual lines, permit the rapid mutation of known genes. Accordingly, studying abscission zone development in *Arabidopsis* permits a rapid translation of gene discoveries into agricultural application.

Microarray approaches using DNA chips to monitor global changes in RNA expression provide the ability to detect numerous genes affected by a particular mutation (Schena et al., 1995, *Science* 270: 467–469, which is incorporated by reference herein in its entirety), such as the nevershed mutation. In one embodiment, expression profiling is carried out using high-density chips developed through a consortium of plant scientists and Affymetrix Corporation to develop high-density chips containing most, or all, *Arabidopsis* genes. The Affymetrix chip design differs from the glass slide microarray systems currently available to the *Arabidopsis* community, in that gene coding regions on the Affymetrix chip are represented on average by about 20 oligonucleotides each, instead of being represented by cDNAs.

Because the oligonucleotides on the chip are short (25 mers), they represent an improvement for monitoring the expression levels of genes which have close family members. In one embodiment, the low variability and high chip to chip reproducibility allows use of a single probe for hybridization rather than the two-color fluorescence system used with glass microarrays, further allowing direct comparisons of hybridization results between different experiments and different labs.

In one embodiment, probes for chip hybridization are prepared as follows: poly $A^+$-RNAs is isolated from the floral abscission zone regions of nevershed mutants and of wildtype plants using standard procedures (Carninci et al., 1996, *Plant J* 17: 699–707; Theologis et al., 1985, *J Mol Biol* 183: 53–68, both of which are incorporated by reference herein in their entireties) at a range of affected stages determined through the mutant characterization described above. RNA probes are biotinylated, the probes are incubated with chips under conditons favorable for hybridization, and the array is stained with a phycoerythrin-streptavadin conjugate (Winzler et al., 1998, *Science* 281: 1191–1197, which is incorporated by reference herein in its entirety). Arrays are then scanned with a laser confocal scanning device that detects and records the amount of fluorescence (Wodicka et al., 1997, *Nature Biotechnology* 15: 1359–1367, which is incorporated by reference herein in its entirety).

Current software tools and database support available for expression data analysis include data files containing a list of array locations and associated intensities are generated first. These files are then entered into a relational database (Sybase), which allows reporting of experimental conditions and mapping of the array locations to those described by the chip manufacturer. Another relational database (RAD) is used to store expression data. RAD has tables organized in three categories 1) an array-specific set of tables specifying what is located where in the array, 2) tables containing experimental details, and 3) tables representing RNA abundance data. Data analysis using RAD tables is being improved through links to DOTS (database of transcribed sequences), as DOT allows transcribed sequences to be compared and likely sequence functions described. DOT links are the primary tools for gene discovery, as clones represented in arrays have little associated information other than sequence and its cDNA library/tissue source.

Based on the high frequency of abscission zone markers observed among enhancer trap lines (Campisi et al., 1999, *Plant J* 17 699–707, which is incorporated by reference herein in its entirety), it is predicted that many genes—as many as 4000 or more—are expressed in abscission zones. Preferably, the Affymetrix chip is used for analysis of abscission zone markers, as this chip permits expression analysis of sufficiently large numbers of genes, is highly reproducible, and has hybridization conditions that allow for greatly increased sensitivity to detect relative RNA levels.

In other embodiments, a filtering strategy is used to characterize abscission zone markers of potential importance. Preferably, poly A⁺-RNA is isolated from the abscission zone regions of nevershed and wild-type, respectively, and labeled for use in two separate microarrays; poly A⁺-RNA from the abscission zone regions of the ethylene-insensitive ein2 mutants is isolated and labeled for use in a third microarray. Because abscission is delayed in the ein2 mutant, but occurs eventually, the early events of abscission zone differentiation can be presumed to be unaffected in ein2.

If the same range of floral stages are reflected in the ein2 RNA probes, then identifying clones which are dramatically affected in nevershed flowers but not in ein2 flowers or wildtype, should identify the clones corresponding to genes involved in the earliest events of abscission zone differentiation. Clones in this "early" category are analyzed further by RNA blot analysis to: a) verify that expression is significantly altered; b) determine their temporal profile within floral abscission zones; and c) ascertain whether they are abscission-zone specific. Clones showing dramatic alteration in expression, which show the earliest temporal profiles, and which appear to be abscission-zone specific will be further analyzed as candidates to screen for corresponding loss-of-function mutants in T-DNA insertional collections.

In other embodiments, molecular markers from gene- and enhancer-trap collections, currently among the most informative tools available to characterize *Arabidopsis* mutants (Sundaresan et al., 1995, *Genes Dev* 9: 1979–1810, which is incorporated by reference herein in its entirety) are used in crosses with developmental mutants to detect evidence of altered molecular differentiation even before phenotypic defects become visible.

Although abscission zone molecular markers are plentiful (Campisi et al., 1999, supra, which is incorporated by reference herein in its entirety), their usefulness has not yet been exploited to study mutants in which abscission is disrupted or to uncover additional genes whose products are involved in the abscission process. In one study of over 11,300 enhancer trap lines that were stained and analyzed (Campisi et al., 1999, supra, which is incorporated by reference herein in its entirety), about 16% or 1800 lines showed staining patterns in the abscission zone. These lines represent an invaluable resource to analyze the nevershed mutant as well as other mutants which disrupt the abscission process, as markers for numerous stages of abscission zone differentiation should be represented within this collection.

In one embodiment of the invention, abscission zone markers representing different temporal profiles are crossed with nevershed mutants in order to more precisely determine the stage at which abscission zone development is first affected in these mutants. A collection of frozen, individually stained lines, will be screened for potential abscission zone markers, and seeds having potential abscission zone markers are obtained. Markers are selected from the collection to reflect as many temporal profiles as possible, including markers which are expressed specifically at the bases of developing floral organs as early as stage 6, and markers expressed as late as stage 17 in abscission zone scar tissue. Further embodiments include studies of the expression profiles of chitinase::GUS and glucanase::GUS abscission zone markers in nevershed mutant flowers.

Example 5

ARF GAP and Vesicle Transport in Plant Floral Organ Abscission

The present invention also includes wild-type and mutant ARF GAP polynucleotides and polypeptides that can be used to determine the role of vesicle transport in abscission zone differentiation and floral organ abscission. Moreover, the ability to genetically manipulate abscission zone differentiation in agronomically important plants will provide valuable opportunities to improve crop yield and to simplify harvesting.

For instance, temporarily unfavorable environmental conditions such as high temperatures, drought, and flooding cause flower bud abscission in important crops such as cotton and field beans (Lloyd, 1920, *Ann NY Acad Sci* 29:1; Osborne, 1989, *Crit Rev Plant Sci* 8: 103–129, both of which are incorporated by reference herein in their entireties). Environmental stresses including cold temperatures can cause flower bud abscission in fruit trees and other flowering plants, reducing the potential number of sites at which fruit can set and thereby reducing yield potential even if environmental conditions improve later in the season. If these crops are genetically engineered to delay abscission zone differentiation until after flower opening, crop yield will be significantly improved, particularly during periods of sudden, extreme weather conditions. Preventing development of particular abscission zones, such as the pedicel abscission zone, are anticipated to streamline mechanical harvesting of many fruit crops, as has already been demonstrated by the widespread agricultural use of jointless tomato crops (Osborne, 1989, supra; Szymkowiak and Irish, 1999, *Plant Cell* 11: 159–176, both of which are incorporated by reference herein in their entireties). Since jointless tomato fruits are "stemless" when harvested, they are highly desirable for products such as tomato juice and canned tomatoes.

Advances made in understanding floral abscission in *Arabidopsis* are applicable to crops in which it would be desirable to control abscission. Although differences exist between plant species as to which plant organs undergo abscission and the timing of abscission, many aspects of abscission zone differentiation and the abscission process itself are conserved between *Arabidopsis* and important crop species, as has already been demonstrated in numerous studies of the abscission process. Cell wall hydrolyzing enyzmes implicated in abscission such as cellulases and polygalacturonases have been identified in many plant species studied so far (del Campillo and Bennett, 1996, *Plant Physiol* 111: 813–820; Koehler et al. 1996, *Plant Mol Biol* 31: 595–606; Trainotti et al., 1997, *Plant Mol Biol* 34: 791–802; del Campillo, 1999, *Curr Top Bev Biol* 46: 39–61; Torki et al., 1999, *Mol Gen Genet* 261: 948–952, all of which are incorporated by reference herein in their entireties).

Furthermore, vital components of the ethylene response pathway, such as ethylene receptors, also show conservation in distantly-related plant species (Mita et al., 1998, *Plant Cell Physiol* 39: 1209–1217; Sato-Nara et al., 1999, *Plant Physiol* 120: 321–330, both of which are incorporated by reference herein in their entireties). For example, the never-ripe mutant of tomato corresponds to an ethylene receptor, and exhibits delayed floral abscission as well as ripening defects (Lanahan et al., 1994, *Plant Cell* 6: 521–530; Wilkinson et al., 1995, *Science* 270: 1807–1809, both of which are incorporated by reference herein in their entireties). Dominant mutant forms of an *Arabidopsis* ethylene receptor, ETR1, when introduced into other species, such as tomato and petunia, also cause delayed floral abscission just as in *Arabidopsis* (Wilkinson et al., 1997, *Nature Biotechnology* 15: 444–447, which is incorporated by reference herein in its entirety).

Tremendous potential exists for abscission-related gene discovery in Arabidopsis. The molecular genetic approaches to explore abscission zone development and the genes involved will be greatly facilitated by the advantages of studying this model plant system and then applying the knowledge gained from *Arabidopsis* to other plants.

Example 6

NEVERSHED Effects on Resource Allocation to Fruits

Preliminary analyses suggested that the fruits of nevershed mutants are somewhat shorter than wild-type fruits. In order to determine whether one of the purposes of floral organ abscission is redistribution, or allocation, of energy resources to the developing fruit, careful measurements are made of nevershed fruits from mutants backcrossed at least three times to wildtype. Measurements made include fruit length, diameter, ratio of length to diameter, cell wall thickness, seed number, seed weight, nitrogen content, carbon content, water content, and any other parameters that suggest how resources are allocated in nevershed and wild-type fruits. A difference in various parameters between wildtype fruits and nevershed fruits from near-isogenic backgrounds would indicate that floral organ abscission has a role in determining the allocation of energy resouces to developing fruits.

Example 7

Abscission Zone Development

The development of the abscission zone of nevershed and wild-type flowers is examined by tissue sectioning and by scanning electron microscopy, as described in Liljegren et al. (2000, *Nature* 404, 766–770, which is incorporated by reference herein in its entirety), and is tested for chemical composition, and physical and mechanical properties. For histological staining, tissue from wild-type and nevershed mutants is fixed, sectioned and stained with toluidine blue, as described by Mixukami & Ma (1992, *Cell* 71: 119–131, which is incorporated by reference herein in its entirety) with minor modifications. For lignin analysis, sections are stained for 2 minutes in a 2% phloroglucinol solution in 95% ethanol, then photographed in 50% hydrochloric acid. For scanning electron microscopy, tissue from wild-type and nevershed mutants is fixed for approximately 4 h at 25° C. in FAA (50% ethanol, 5% glacial acetic acid, 3.7% formaldehyde) and prepared for scanning electron microscopy. Samples are examined in a Cambridge S360 scanning electron microscope using an accelerating voltage of 10 kV. Breakstrength testing of the floral organs of the nevershed mutant and the floral organs of the wild-type is performed to test physical and mechanical properties of each type.

The abscission zones of wild-type *Arabidopsis* floral organs, like those of other plants, consist of small, densely cytoplasmic cells, and appear to be only a few cell layers thick. Abscission zone development of the nevershed mutant is blocked at an early stage. Expression analyses of abscission zone molecular markers in the nevershed mutant as described below is used to assist in pinpointing the stage at which abscission zone development is first disrupted.

Example 8

Temporal and Spatial Expression Profiling

Temporal and spatial expression profiling of the NEVERSHED gene is carried out in plants transformed with an expression vector having the NEVERSHED promoter region and the β-glucuronidase (GUS) reporter gene, and tissues were fixed, sectioned, and stained as described in Blazquez et al., (1997, *Development* 124: 3835–3844, which is incorporated by reference herein in its entirety), with minor modifications, and in Ferrandiz et al (2000, *Science* 289: 436–438, which is incorporated by reference herein in its entirety).

Example 9

Expression Profiling

Candidates for genes that act downstream of NEVERSHED, or are otherwise in a regulatory relation with NEVERSHED, are identified using high-density Affymetrix chips representing the *Arabidopsis* genome. The expression profiles wild-type, nev-1 and nev-2 *Arabidopsis* in the same genetic background are compared, and differences in expression between wild-type and nevershed mutants are used to determine genes whose expression is affected by the expression of the NEVERSHED gene.

The first experiment uses first-generation chips containing almost two-thirds of the *Arabidopsis* genome, which is about 13–16,000 out of 20–25,000 predicted total genes. Next, chips having greater coverage of the *Arabidopsis* genome are used. Results from chips that have incomplete coverage of the genome, but in combination provide complete coverage of the genome, are combined to determine the global expression profile of wildtype and nevershed mutants. In another experiment, chips containing the entire *Arabidopsis* genome are utilized to determine the effects of nevershed mutants on the expression of all genes in the *Arabidopsis genome*.

In order to make probes for chip hybridization, poly A$^+$-RNAs are isolated from the floral abscission zone regions of nevershed mutants and wildtype plants using standard procedures (Carninci et al., 1996, *Genomics* 37: 327–336; Theologis et al., 1985, *J Mol Biol* 183: 53–68, both of which are incorporated by reference herein in their entireties), from plants at a number of critical developmental stages determined through mutant characterization. RNA probe are biotinylated, and the labelled probes are incubated with the chip under conditions favorable for hybridization. The array is stained with a phycoerythrin-streptavadin conjugate and then scanned with a laser confocal scanning device that detects and records the amount of fluorescence, as described by Wodicka et al. (1997, supra, which is incorporated by reference herein in its entirety).

Example 10

Analysis of Abscission Zone Molecular Markers in the Nevershed Mutant

Molecular marker for the abscission zone are selected from the over 1800 *Arabidopsis* enhancer trap lines that show staining patterns in the abscission zone (Campisi et al., 1999, *Plant J* 17: 699–707, which is incorporated by reference herein in its entirety). Markers for numerous stages of abscission zone differentiation are represented within this collection. Molecular markers from gene- and enhancer-trap collections are crossed to nevershed mutants, to provide evidence of altered molecular differentiation can be detected even before phenotypic defects become visible. Tissues are stained as described by Campisi et al. (1999, supra, which is incorporated by reference herein in its entirety) and the lines which show activity at crucial developmental stages and/or crucial locations are selected.

Markers which are expressed specifically at the bases of developing floral organs are detected by staining as early as stage 6 and markers expressed as late as stage 17 are detected by staining in abscission zone scar tissue. Abscission zone markers representing different temporal profiles are crossed to nevershed mutants and are used to pinpoint the stage at which abscission zone development is first affected in these mutants.

Example 11

Molecular Characterization of Abscission Zone Molecular Markers

Molecular characterization of abscission zone markers affected by the nevershed mutation is carried out to uncover additional genes involved in abscission zone development. As described previously, a set of ten markers representing different temporal abscission zone profiles are crossed to the nevershed mutant. In a separate experiment, these markers are also be crossed to an ethylene-insensitive mutant, ein2, in which floral abscission is delayed. Because EIN2 is an integral member of the ethylene-response pathway abscission zone markers which are regulated by this pathway will show delayed expression profiles in ein2 mutant flowers compared to wildtype. This experiment demonstrates that most if not all markers which are regulated by the ethylene-response pathway also show altered expression profiles in the nevershed mutant.

Example 12

Screening T-DNA Populations for Additional Abscission Mutants

Loss-of-function mutants are identified by screening DNA insertional lines. Genes that act downstream of NEVERSHED, identified through microarray analyses and characterization of abscission zone markers as described above, are used in screens of a collection of T-DNA insertional lines containing 150,000 individual T-DNA tagged lines, and the estimated equivalent of 225,000 insertions. Gene-specific oligonucleotides and oligonucleotides from the T-DNA borders, DNA pools of this collection are screened as described by Krysan et al., (1996, *Proc Nat Acad Sci USA* 93: 8145–8150, which is incorporated by reference herein in its entirety). Pools that show hybridizing bands are broken down until individual lines are positively identified. Seeds from identified T-DNA tagged mutants are planted out, and the phenotypes of the resulting plants analyzed.

Example 13

ARF GAP Activity of NEVERSHED

NEVERSHED is expressed in a plant cell expression system and purified using the method of Makler et al (1995, *Jnl Biol Chem* 270: 5232–5237, which is incorporated by reference herein in its entirety) modified for extraction from plant cells. The ARF-directed GAP activity of NEVERSHED is measured by at the method of Makler et al (1995, *Jnl Biol Chem* 270: 5232–5237, which is incorporated by reference herein in its entirety), where the assay measures a single round of a GTPase reaction. ARF1 is loaded with $^{32}[\alpha\text{-P}]$GTP in the presence of dimyristoyl phosphatidylcholine (DMPC) and cholate and using a relatively high ARF concentration in order to achieve high loading efficiency. The loading reaction mixture contains ARF1 (0.5 mg/ml), $^{32}[\alpha\text{-P}]$GTP (0.2 mCi/ml, 0.25 µM), 5 mM MgCl$_2$, 1 mM DTT, 1 mM ATP plus ATP/GTP regeneration system (5 mM phosphocreatine and 50 µg/ml creatine phosphokinase), 25 mM MOPS buffer, pH 7.5, 150 mM KCl, and a mixture of DMPC and sodium cholate, added last from a 10× stock to give 3 mM and 1 mg/ml, respectively. Loading is carried out for 90 min at 30° C., and the preparation was divided into small aliquots and stored at −80° C. Filter binding assays show that between 30 and 60% of the $^{32}[\alpha\text{-P}]$GTP becomes associated with different preparations of recombinant ARF-.GAP activity was assayed in a final volume of 10 µl in the presence of 5 mM MgCl$_2$, 1 mM DTT, 1 mM ATP plus the above mentioned ATP/GTP regeneration system, 25 mM MOPS buffer, pH 7.5, 0.5 mM unlabeled GTP, 0.1 unit/ml guanylate kinase, and 1 µl of $^{32}[\alpha\text{-P}]$GTP-loaded ARF. Following incubation for 15 min at 30° C., reactions are boiled for 1 min to release the nucleotides from ARF, and the nucleotides are separated by thin layer chromatography on PEI-cellulose sheets, developed with 1.2 M Tris-Cl, pH 7.4. $^{32}[\alpha\text{-P}]$GDP formation is determined by autoradiography or by cutting the GDP and GTP areas, and determination of radioactivity is made using Cerenkov radiation.

Data are presented as the percentage of ARF-bound $^{32}[\alpha\text{-P}]$GTP that is converted to $^{32}[\alpha\text{-P}]$GDP. Background values are 4–5%, and these values do not increase during incubations in the absence of a GAP. Where appropriate, GAP activity is assessed by carrying out serial dilutions of the sample, and specific activity is calculated at the protein concentration that results in 50% hydrolysis of ARF-bound GTP.

Sequences of NEVERSHED and *Arabidopsis* Homologs

There are at least 5 other *Arabidopsis* genes containing homology to the NEVERSHED ARFGAP domain. For example, MKP6.22, is shown in SEQ ID NO: 9 (genomic sequence) and SEQ ID NO: 10 (amino acid sequence). The amino acid sequence of MKP6.22 is 76% identical to NEVERSHED at the amino acid sequence level in the ARF GAP domain. Other genes having homology to the NEVERSHED ARF GAP domain include the F13M22.5 homolog (SEQ ID NO: 11 (genomic sequence) and SEQ ID NO: 12 (amino acid sequence)), the F17A17.28 homolog (SEQ ID NO: 13 (genomic sequence) and SEQ ID NO: 14 (amino acid sequence)), the F5K20.10 homolog (SEQ ID NO: 15 (genomic sequence) and SEQ ID NO: 16 (amino acid sequence)), and the MZA15.17 homolog (SEQ ID NO: 17 (genomic sequence) and SEQ ID NO: 18 (amino acid sequence)).

The genomic sequence of wild-type NEVERSHED (MDK4.13), as displayed in the complementary direction, is shown in SEQ ID NO: 8. The exon locations (complementary direction) are as follows: 0024 . . . 0192, 0306 . . . 0382, 0492 . . . 0731, 0957 . . . 1129, 1264 . . . 1477, 1744 . . . 1975, 2093 . . . 2183, 2270 . . . 2324, 2724 . . . 2814, 2902 . . . 2960, 3778 . . . 3828. The predicted promoter region (complementary direction): occurs at approximately 3829–5567 of SEQ ID NO: 8.

The genomic sequence of MKP6.22 is shown in SEQ ID NO: 9. The exon locations are as follows: 678 . . . 728, 820 . . . 878, 969 . . . 1059, 1142 . . . 1196, 1285 . . . 1375, 1471 . . . 1672, 1822 . . . 1911, and 2052 . . . 2156. The promoter region is located at nucleic acid numbers 49 through 677. The polypeptide sequence of MKP6.22 is shown in SEQ ID NO. 10.

The genomic sequence of the F13M22.5 homolog, displayed in the forward direction, is shown in SEQ ID NO: 11. The genomic sequence, displayed in the complementary direction, is shown in SEQ ID NO: 19. The exons (complementary direction) are located at nucleic acid numbers 41 . . . 547, 982 . . . 1059, and 1168 . . . 1953 of SEQ ID NO: 19. The promoter (complementary direction) is located at approximately 1954–3138 of SEQ ID NO: 19. The polypeptide sequence of F13M22.5 is shown in SEQ ID NO: 12.

The genomic sequence of the F17A17.28 homolog is shown in SEQ ID NO: 13. The exons are located at position numbers 1026 . . . 1032, 1264 . . . 1353, 1447 . . . 1531, 1609 . . . 1684, 1778 . . . 1941, 2022 . . . 2226, 2310 . . . 24266, 2506 . . . 2601, and 2677 . . . 2958. The promoter region is located at approximately position 7 to 1025. The polypeptide sequence of the F17A17.28 homolog is shown in SEQ ID NO: 14.

The genomic sequence of the F5K20.10 homolog, displayed in the forward direction, is shown in SEQ ID NO: 15. The genomic sequence, displayed in the complementary direction, is shown in SEQ ID NO: 20. The exons (complementary direction) are located at positions 266 . . . 355, and –481 . . . 40 of SEQ ID NO: 20. The promoter region (complementary direction) is located at position 356 through approximately position 5636 of SEQ ID NO: 20. The polypeptide sequence of the F5K20.10 homolog is shown in SEQ ID NO: 16.

The genomic sequence of the MZA15.17 homolog, displayed in the forward direction, is shown in SEQ ID NO: 17. The genomic sequence, displayed in the complementary direction, is shown in SEQ ID NO: 21. The exons (complementary direction) are located at positions 25 . . . 132, 224 . . . 325, 411 . . . 536, 629 . . . 889, 975 . . . 1398, 1605 . . . 1723, and 1824 . . . 1892 of SEQ ID NO: 21. The promoter region (complementary direction) is located at position 1893 though approximately 4305 of SEQ ID NO: 21. The polypeptide sequence of the MZA15.17 homolog is shown in SEQ ID NO: 18.

What is claimed is:

1. A method of preventing floral organ loss in a plant, comprising: mutating the ARF GAP domain of a NEVERSHED gene in said plant, wherein said NEVERSHED gene comprises the nucleotide sequence of SEQ ID NO:1.

2. The method of claim 1, wherein said mutating comprises exposure said plant to ethyl methanesulphonate (EMS).

3. The method of claim 1, wherein said mutating results in said NEVERSHED gene expressing a protein that is not full-length.

4. The method of claim 1, wherein said mutating results in said NEVERSHED gene expressing an inactive protein.

5. The method of claim 1, wherein said mutating introduces a stop codon into said NEVERSHED gene.

6. The method of claim 1, further comprising determining if said mutation results in prevention of floral organ loss in said plant.

7. The method of claim 2, further comprising determining if said mutation results in prevention of floral organ loss in said plant.

8. The method of claim 3, further comprising determining if said mutation results in prevention of floral organ loss in said plant.

9. The method of claim 4, further comprising determining if said mutation results in prevention of floral organ loss in said plant.

10. The method of claim 5, further comprising determining if said mutation results in prevention of floral organ loss in said plant.

* * * * *